US011896330B2

(12) United States Patent
Castillo et al.

(10) Patent No.: US 11,896,330 B2
(45) Date of Patent: Feb. 13, 2024

(54) ROBOTIC MEDICAL SYSTEM HAVING MULTIPLE MEDICAL INSTRUMENTS

(71) Applicant: Auris Health, Inc., Redwood City, CA (US)

(72) Inventors: Andre J. Castillo, Redwood City, CA (US); Akira Bryan Ueda, San Francisco, CA (US); Adrian Tyler Hairrell, San Francisco, CA (US); Nikhil S. Joshi, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 513 days.

(21) Appl. No.: 16/994,397

(22) Filed: Aug. 14, 2020

(65) Prior Publication Data

US 2021/0045819 A1    Feb. 18, 2021

Related U.S. Application Data

(60) Provisional application No. 62/887,569, filed on Aug. 15, 2019.

(51) Int. Cl.
*A61B 34/35*    (2016.01)
*B25J 9/16*    (2006.01)
(Continued)

(52) U.S. Cl.
CPC .................. *A61B 34/35* (2016.02); *B25J 9/06* (2013.01); *B25J 9/1689* (2013.01);
(Continued)

(58) Field of Classification Search
CPC .............. A61B 34/35; A61B 2034/301; A61B 2034/302; A61B 17/221; A61B 18/20;
(Continued)

(56) References Cited

U.S. PATENT DOCUMENTS 2,556,601 A    6/1951    Schofield
2,566,183 A    8/1951    Forss
(Continued)

FOREIGN PATENT DOCUMENTS

AU    2017336790 A1    4/2019
AU    2018243364 A1    10/2019
(Continued)

OTHER PUBLICATIONS

Notice of Allowance for U.S. Appl. No. 15/948,369, dated May 10, 2022, 11 pages.
(Continued)

*Primary Examiner* — Richard G Louis
(74) *Attorney, Agent, or Firm* — Chang & Hale LLP

(57) ABSTRACT

Certain aspects relate to robotic medical instrument systems. Such a system can include first and second medical instruments. The first medical instrument can include an instrument base and an elongate shaft extending from the instrument base, and a robotic drive input. The first medical instrument may include an instrument inlet. The second medical instrument may include an instrument base and an elongate shaft that extends through the instrument inlet. The second medical instrument can include a robotic drive input that is coupled to a rotating element in the second medical instrument. The robotic medical instrument system can include a robotic arm that has first and second robotic drive outputs. The first robotic drive output can drive the robotic drive input of the first medical instrument, and the second robotic drive output can drive the robotic drive input of the second medical instrument.

29 Claims, 34 Drawing Sheets

(51) Int. Cl.
  *B25J 15/00* (2006.01)
  *B25J 9/06* (2006.01)
  *A61B 34/30* (2016.01)

(52) U.S. Cl.
  CPC ..... *B25J 15/0066* (2013.01); *A61B 2034/301* (2016.02); *A61B 2034/302* (2016.02)

(58) Field of Classification Search
  CPC .......... A61B 34/37; A61B 2017/00477; A61B 1/00149; A61B 1/0016; A61B 34/20; A61B 34/74; A61B 50/13; A61B 2034/2065; A61B 2034/305; A61B 2017/00407; B25J 9/06; B25J 9/1689; B25J 15/0066; B25J 9/0087
  See application file for complete search history.

(56) References Cited

U.S. PATENT DOCUMENTS

| | | | |
|---|---|---|---|
| 2,623,175 A | 12/1952 | Finke | |
| 2,730,699 A | 1/1956 | Gratian | |
| 2,884,808 A | 5/1959 | Mueller | |
| 3,294,183 A | 12/1966 | Riley et al. | |
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,763,860 A | 10/1973 | Clarke | |
| 3,784,031 A | 1/1974 | Nitu | |
| 3,790,002 A | 2/1974 | Guilbaud et al. | |
| 3,921,536 A | 11/1975 | Savage | |
| 3,926,386 A | 12/1975 | Stahmann | |
| 4,040,413 A | 8/1977 | Ohshiro | |
| 4,141,245 A | 2/1979 | Brandstetter | |
| 4,198,960 A | 4/1980 | Utsugi | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck et al. | |
| 4,384,493 A | 5/1983 | Grunbaum | |
| 4,470,407 A | 9/1984 | Hussein | |
| 4,507,026 A | 3/1985 | Lund | |
| 4,530,471 A | 7/1985 | Inoue | |
| 4,532,935 A | 8/1985 | Wang et al. | |
| 4,555,960 A | 12/1985 | King | |
| 4,611,594 A | 9/1986 | Grayhack et al. | |
| 4,685,458 A | 8/1987 | Leckrone | |
| 4,688,555 A | 8/1987 | Wardle | |
| 4,741,335 A | 5/1988 | Okada | |
| 4,745,908 A | 5/1988 | Wardle | |
| 4,747,405 A | 5/1988 | Leckrone | |
| 4,784,150 A | 11/1988 | Voorhies et al. | |
| 4,854,301 A | 8/1989 | Nakajima | |
| 4,857,058 A | 8/1989 | Payton | |
| 4,898,574 A | 2/1990 | Uchiyama et al. | |
| 4,899,733 A | 2/1990 | DeCastro et al. | |
| 4,907,168 A | 3/1990 | Boggs | |
| 4,945,790 A | 8/1990 | Golden | |
| 4,983,165 A | 1/1991 | Loiterman | |
| 5,029,574 A | 7/1991 | Shimamura et al. | |
| 5,085,659 A | 2/1992 | Rydell | |
| 5,150,452 A | 9/1992 | Pollack et al. | |
| 5,190,542 A | 3/1993 | Nakao et al. | |
| 5,190,557 A | 3/1993 | Borodulin et al. | |
| 5,196,023 A | 3/1993 | Martin | |
| 5,207,128 A | 5/1993 | Albright | |
| 5,217,465 A | 6/1993 | Steppe | |
| 5,234,428 A | 8/1993 | Kaufman | |
| 5,256,150 A | 10/1993 | Quiachon et al. | |
| 5,277,085 A | 1/1994 | Tanimura et al. | |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,350,101 A | 9/1994 | Godlewski | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,426,687 A | 6/1995 | Goodall et al. | |
| 5,431,649 A | 7/1995 | Muller et al. | |
| 5,441,485 A | 8/1995 | Peters | |
| 5,449,356 A | 9/1995 | Walbrink | |
| 5,450,843 A | 9/1995 | Moll et al. | |
| 5,472,426 A | 12/1995 | Bonati et al. | |
| 5,496,267 A | 3/1996 | Drasler | |
| 5,501,667 A | 3/1996 | Verduin, Jr. | |
| 5,507,725 A | 4/1996 | Savage et al. | |
| 5,520,684 A | 5/1996 | Imran | |
| 5,524,180 A | 6/1996 | Wang et al. | |
| 5,545,170 A | 8/1996 | Hart | |
| 5,559,294 A | 9/1996 | Holum et al. | |
| 5,562,239 A | 10/1996 | Bolarski et al. | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,697,949 A | 12/1997 | Giurtino et al. | |
| 5,709,661 A | 1/1998 | Van Egmond | |
| 5,710,870 A | 1/1998 | Ohm | |
| 5,716,325 A | 2/1998 | Bonutti | |
| 5,737,500 A | 4/1998 | Seraji et al. | |
| 5,767,840 A | 6/1998 | Selker | |
| 5,779,623 A | 7/1998 | Bonnell | |
| 5,788,667 A | 8/1998 | Stoller | |
| 5,788,710 A | 8/1998 | Bates et al. | |
| 5,792,135 A | 8/1998 | Madhani et al. | |
| 5,792,165 A | 8/1998 | Klieman | |
| 5,797,900 A | 8/1998 | Madhani | |
| 5,798,627 A | 8/1998 | Gilliland | |
| 5,810,770 A | 9/1998 | Chin et al. | |
| 5,842,390 A | 12/1998 | Bouligny | |
| 5,855,583 A | 1/1999 | Wang et al. | |
| 5,893,869 A | 4/1999 | Barnhart | |
| 5,897,491 A | 4/1999 | Kastenbauer et al. | |
| 5,921,968 A | 7/1999 | Lampropoulos et al. | |
| 5,924,175 A | 7/1999 | Lippitt | |
| 5,943,056 A | 8/1999 | Sato | |
| 5,967,934 A | 10/1999 | Ishida et al. | |
| 5,969,230 A | 10/1999 | Sakai et al. | |
| 5,989,230 A | 11/1999 | Frassica | |
| 6,071,281 A | 6/2000 | Burnside et al. | |
| 6,077,219 A | 6/2000 | Viebach | |
| 6,084,371 A | 7/2000 | Kress et al. | |
| 6,093,157 A | 7/2000 | Chandrasekaran | |
| 6,110,171 A | 8/2000 | Rydell | |
| 6,120,476 A | 9/2000 | Fung et al. | |
| 6,120,498 A | 9/2000 | Jani et al. | |
| 6,154,000 A | 11/2000 | Rastegar et al. | |
| 6,156,030 A | 12/2000 | Neev | |
| 6,159,220 A | 12/2000 | Gobron et al. | |
| 6,171,234 B1 | 1/2001 | White et al. | |
| 6,174,318 B1 | 1/2001 | Bates et al. | |
| 6,183,482 B1 | 2/2001 | Bates et al. | |
| 6,185,478 B1 | 2/2001 | Koakutsu et al. | |
| 6,206,903 B1 | 3/2001 | Ramans | |
| 6,236,906 B1 | 5/2001 | Muller | |
| 6,183,435 B1 | 6/2001 | Bumbalough et al. | |
| 6,272,371 B1 | 8/2001 | Shlomo | |
| 6,289,579 B1 | 9/2001 | Viza et al. | |
| 6,302,895 B1 | 10/2001 | Gobron et al. | |
| 6,322,557 B1 | 11/2001 | Nikolaevich | |
| 6,375,635 B1 | 4/2002 | Moutafis | |
| 6,394,998 B1 | 5/2002 | Wallace et al. | |
| 6,401,572 B1 | 6/2002 | Provost | |
| 6,405,078 B1 | 6/2002 | Moaddeb et al. | |

(56) References Cited

U.S. PATENT DOCUMENTS

| | | |
|---|---|---|
| 6,428,563 B1 | 8/2002 | Keller |
| 6,436,107 B1 | 8/2002 | Wang et al. |
| 6,440,061 B1 | 8/2002 | Wenner et al. |
| 6,487,940 B2 | 12/2002 | Hart et al. |
| 6,491,701 B2 | 12/2002 | Tierney et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,659,939 B2 | 12/2003 | Moll et al. |
| 6,673,080 B2 | 1/2004 | Reynolds et al. |
| 6,676,668 B2 | 1/2004 | Mercereau et al. |
| 6,685,698 B2 | 2/2004 | Morley et al. |
| 6,695,818 B2 | 2/2004 | Wollschlager |
| 6,706,050 B1 | 3/2004 | Giannadakis |
| 6,726,675 B1 | 4/2004 | Beyar |
| 6,786,896 B1 | 9/2004 | Madhani et al. |
| 6,827,712 B2 | 12/2004 | Tovey et al. |
| 6,991,602 B2 | 1/2006 | Nakazawa et al. |
| 7,044,936 B2 | 5/2006 | Harding |
| 7,172,580 B2 | 2/2007 | Hruska et al. |
| 7,248,944 B2 | 7/2007 | Green |
| 7,276,044 B2 | 10/2007 | Ferry et al. |
| 7,282,055 B2 | 10/2007 | Tsuruta |
| 7,524,284 B2 | 4/2009 | Murakami et al. |
| 7,559,934 B2 | 7/2009 | Teague et al. |
| 7,615,042 B2 | 11/2009 | Beyar et al. |
| 7,635,342 B2 | 12/2009 | Ferry et al. |
| 7,645,283 B2 | 1/2010 | Reynolds et al. |
| 7,736,356 B2 | 6/2010 | Cooper et al. |
| 7,766,856 B2 | 8/2010 | Ferry et al. |
| 7,882,841 B2 | 2/2011 | Aljuri |
| 7,914,540 B2 | 3/2011 | Schwartz et al. |
| 7,938,809 B2 | 5/2011 | Lampropoulos et al. |
| 7,963,911 B2 | 6/2011 | Turliuc |
| 7,972,298 B2 | 7/2011 | Wallace et al. |
| 7,974,674 B2 | 7/2011 | Hauck et al. |
| 7,987,046 B1 | 7/2011 | Peterman |
| 7,998,020 B2 | 8/2011 | Kidd et al. |
| 8,002,713 B2 | 8/2011 | Heske |
| 8,004,229 B2 | 8/2011 | Nowlin et al. |
| 8,016,839 B2 | 9/2011 | Wilk |
| 8,038,598 B2 | 10/2011 | Khachi |
| 8,043,303 B2 | 10/2011 | Razvi et al. |
| 8,052,636 B2 | 11/2011 | Moll et al. |
| 8,092,397 B2 | 1/2012 | Wallace et al. |
| 8,157,308 B2 | 4/2012 | Pedersen |
| 8,182,415 B2 | 5/2012 | Larkin et al. |
| 8,187,173 B2 | 5/2012 | Miyoshi |
| 8,257,303 B2 | 9/2012 | Moll et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,480,595 B2 | 7/2013 | Speeg |
| 8,523,762 B2 | 9/2013 | Miyamoto et al. |
| 8,540,748 B2 | 9/2013 | Murphy et al. |
| 8,541,970 B2 | 9/2013 | Nowlin |
| 8,602,031 B2 | 12/2013 | Reis et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,749,190 B2 | 6/2014 | Nowlin et al. |
| 8,755,124 B2 | 6/2014 | Aschwanden et al. |
| 8,786,241 B2 | 7/2014 | Nowlin et al. |
| 8,820,603 B2 | 9/2014 | Shelton et al. |
| 8,821,480 B2 | 9/2014 | Burbank |
| 8,827,948 B2 | 9/2014 | Romo et al. |
| 8,870,815 B2 | 10/2014 | Bhat et al. |
| 8,882,660 B2 | 11/2014 | Phee et al. |
| 8,894,610 B2 | 11/2014 | Macnamara et al. |
| 8,945,163 B2 | 2/2015 | Voegele et al. |
| 8,956,280 B2 | 2/2015 | Eversull et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,179,979 B2 | 11/2015 | Jinno |
| 9,204,933 B2 | 12/2015 | Reis et al. |
| 9,254,123 B2 | 2/2016 | Alvarez et al. |
| 9,259,280 B2 | 2/2016 | Au |
| 9,259,281 B2 | 2/2016 | Griffiths et al. |
| 9,259,282 B2 | 2/2016 | Azizian |
| 9,296,104 B2 | 3/2016 | Swarup et al. |
| 9,326,822 B2 | 5/2016 | Lewis et al. |
| 9,345,456 B2 | 5/2016 | Tsonton et al. |
| 9,345,544 B2 | 5/2016 | Hourtash et al. |
| 9,375,284 B2 | 6/2016 | Hourtash |
| 9,408,669 B2 | 8/2016 | Kokish et al. |
| 9,415,510 B2 | 8/2016 | Hourtash et al. |
| 9,446,177 B2 | 9/2016 | Millman et al. |
| 9,452,018 B2 | 9/2016 | Yu |
| 9,457,168 B2 | 10/2016 | Moll et al. |
| 9,460,536 B2 | 10/2016 | Hasegawa et al. |
| 9,480,534 B2 | 11/2016 | Bowling |
| 9,498,601 B2 | 11/2016 | Tanner et al. |
| 9,504,604 B2 | 11/2016 | Alvarez |
| 9,510,911 B2 | 12/2016 | Hourtash |
| 9,517,106 B2 | 12/2016 | Hourtash et al. |
| 9,561,083 B2 | 2/2017 | Yu et al. |
| 9,566,125 B2 | 2/2017 | Bowling |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,029,367 B2 | 7/2018 | Hourtash |
| 10,039,604 B2 | 8/2018 | Chia et al. |
| 10,046,140 B2 | 8/2018 | Kokish et al. |
| 10,071,479 B2 | 9/2018 | Swarup et al. |
| 10,080,576 B2 | 9/2018 | Romo et al. |
| 10,117,713 B2 | 11/2018 | Moctezuma de la Barrera |
| 10,130,429 B1 | 11/2018 | Weir |
| 10,136,949 B2 | 11/2018 | Felder et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,154,822 B2 | 12/2018 | Henderson |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,176,681 B2 | 1/2019 | Plewe et al. |
| 10,213,264 B2 | 2/2019 | Tanner et al. |
| 10,219,867 B2 | 3/2019 | Saglam et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |

(56) References Cited

U.S. PATENT DOCUMENTS

| | | |
|---|---|---|
| 10,244,926 B2 | 4/2019 | Noonan et al. |
| 10,258,285 B2 | 4/2019 | Hauck |
| 10,278,781 B2 | 5/2019 | Taylor et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling |
| 10,327,855 B2 | 6/2019 | Hourtash et al. |
| 10,350,017 B2 | 7/2019 | Bowling |
| 10,350,390 B2 | 7/2019 | Moll et al. |
| 10,363,103 B2 | 7/2019 | Alvarez et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,463,440 B2 | 11/2019 | Bowling |
| 10,464,209 B2 | 11/2019 | Ho et al. |
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,047 B2 | 1/2020 | Yu |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,569,052 B2 | 2/2020 | Kokish et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,687,903 B2 | 6/2020 | Lewis et al. |
| 10,695,536 B2 | 6/2020 | Weitzner et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,112 B2 | 10/2020 | Kokish et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,952 B2 | 11/2020 | Yu |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu |
| 10,881,280 B2 | 1/2021 | Baez |
| 10,888,386 B2 | 1/2021 | Eyre |
| 10,898,276 B2 | 1/2021 | Graetzel et al. |
| 11,083,476 B2 | 8/2021 | Cheon et al. |
| 11,382,650 B2 | 7/2022 | Noonan |
| 11,439,419 B2 | 9/2022 | Lin |
| 11,490,782 B2 | 11/2022 | Rafii-Tari et al. |
| 11,534,249 B2 | 12/2022 | Romo |
| 11,559,360 B2 | 1/2023 | Romo |
| 11,571,229 B2 | 2/2023 | Shah |
| 2001/0042643 A1 | 11/2001 | Krueger et al. |
| 2002/0019644 A1 | 2/2002 | Tastings et al. |
| 2002/0045905 A1 | 4/2002 | Gerbi et al. |
| 2002/0068954 A1 | 6/2002 | Foster |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0111608 A1 | 8/2002 | Baerveldt et al. |
| 2002/0111621 A1 | 8/2002 | Wallace et al. |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0004455 A1 | 1/2003 | Kadziauskas et al. |
| 2003/0040681 A1 | 2/2003 | Ng et al. |
| 2003/0056561 A1 | 3/2003 | Butscher et al. |
| 2003/0065358 A1 | 4/2003 | Frecker et al. |
| 2003/0088254 A1 | 5/2003 | Gregory et al. |
| 2003/0100892 A1 | 5/2003 | Morley et al. |
| 2003/0109780 A1 | 6/2003 | Coste-Maniere et al. |
| 2003/0109877 A1 | 6/2003 | Morley et al. |
| 2003/0109889 A1 | 6/2003 | Mercereau et al. |
| 2003/0158545 A1 | 8/2003 | Hovda et al. |
| 2003/0167623 A1 | 9/2003 | Lorenz |
| 2003/0208189 A1 | 11/2003 | Payman |
| 2003/0212308 A1 | 11/2003 | Bendall |
| 2003/0225419 A1 | 12/2003 | Lippitt et al. |
| 2004/0015053 A1 | 1/2004 | Bieger |
| 2004/0122444 A1 | 6/2004 | Gerard |
| 2004/0143253 A1 | 7/2004 | Vanney et al. |
| 2004/0152972 A1 | 8/2004 | Hunter |
| 2004/0153093 A1 | 8/2004 | Donovan |
| 2004/0158261 A1 | 8/2004 | Vu |
| 2004/0186349 A1 | 9/2004 | Ewers et al. |
| 2004/0193146 A1 | 9/2004 | Lee et al. |
| 2004/0210116 A1 | 10/2004 | Nakao et al. |
| 2004/0243147 A1 | 12/2004 | Lipow |
| 2004/0253079 A1 | 12/2004 | Sanchez |
| 2004/0254566 A1 | 12/2004 | Plicchi |
| 2004/0260246 A1 | 12/2004 | Desmond |
| 2005/0004579 A1 | 1/2005 | Schneider et al. |
| 2005/0033270 A1 | 2/2005 | Ramans et al. |
| 2005/0054900 A1 | 3/2005 | Mawn et al. |
| 2005/0159645 A1 | 7/2005 | Bertolero et al. |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2005/0240178 A1 | 10/2005 | Morley et al. |
| 2005/0261705 A1 | 11/2005 | Gist |
| 2005/0267488 A1 | 12/2005 | Hare et al. |
| 2006/0015133 A1 | 1/2006 | Grayzel et al. |
| 2006/0041245 A1 | 2/2006 | Ferry |
| 2006/0058813 A1 | 3/2006 | Teague et al. |
| 2006/0079884 A1* | 4/2006 | Manzo ............... A61B 18/1442 606/41 |
| 2006/0111692 A1 | 5/2006 | Hlavka et al. |
| 2006/0116693 A1 | 6/2006 | Weisenburgh et al. |
| 2006/0135963 A1 | 6/2006 | Kick et al. |
| 2006/0142657 A1 | 6/2006 | Quaid |
| 2006/0146010 A1 | 7/2006 | Schneider |
| 2006/0156875 A1 | 7/2006 | Mcrury et al. |
| 2006/0161137 A1 | 7/2006 | Orban et al. |
| 2006/0189891 A1 | 8/2006 | Waxman et al. |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0016164 A1 | 1/2007 | Dudney et al. |
| 2007/0021768 A1 | 1/2007 | Nance et al. |
| 2007/0027443 A1 | 2/2007 | Rose et al. |
| 2007/0027534 A1 | 2/2007 | Bergheim et al. |
| 2007/0032906 A1 | 2/2007 | Sutherland et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0106304 A1 | 5/2007 | Hammack et al. |

(56) References Cited

U.S. PATENT DOCUMENTS

| | | |
|---|---|---|
| 2007/0112355 A1 | 5/2007 | Salahieh |
| 2007/0119274 A1 | 5/2007 | Devengenzo et al. |
| 2007/0123855 A1 | 5/2007 | Morley et al. |
| 2007/0135803 A1 | 6/2007 | Belson |
| 2007/0149946 A1 | 6/2007 | Viswanathan |
| 2007/0185377 A1 | 8/2007 | Murakami et al. |
| 2007/0185485 A1 | 8/2007 | Hauck et al. |
| 2007/0191177 A1 | 8/2007 | Nagai et al. |
| 2007/0203475 A1 | 8/2007 | Fischer et al. |
| 2007/0208252 A1 | 9/2007 | Makower |
| 2007/0208375 A1 | 9/2007 | Nishizawa |
| 2007/0213668 A1 | 9/2007 | Spitz |
| 2007/0239028 A1 | 10/2007 | Houser |
| 2007/0239178 A1 | 10/2007 | Weitzner et al. |
| 2007/0245175 A1 | 10/2007 | Zheng et al. |
| 2007/0250111 A1 | 10/2007 | Lu et al. |
| 2007/0299427 A1 | 12/2007 | Yeung et al. |
| 2008/0009884 A1 | 1/2008 | Kennedy |
| 2008/0015566 A1 | 1/2008 | Livneh et al. |
| 2008/0021440 A1 | 1/2008 | Solomon et al. |
| 2008/0027464 A1 | 1/2008 | Moll et al. |
| 2008/0033467 A1 | 2/2008 | Miyamoto et al. |
| 2008/0039255 A1 | 2/2008 | Jinno et al. |
| 2008/0045981 A1 | 2/2008 | Margolin et al. |
| 2008/0046122 A1 | 2/2008 | Manzo et al. |
| 2008/0065103 A1 | 3/2008 | Cooper et al. |
| 2008/0065111 A1 | 3/2008 | Blumenkranz et al. |
| 2008/0065112 A1 | 3/2008 | Tovey et al. |
| 2008/0082109 A1 | 4/2008 | Moll et al. |
| 2008/0091215 A1 | 4/2008 | Saleh |
| 2008/0125698 A1 | 5/2008 | Gerg et al. |
| 2008/0147011 A1 | 6/2008 | Urmey |
| 2008/0177277 A1 | 7/2008 | Huang et al. |
| 2008/0177285 A1 | 7/2008 | Brock et al. |
| 2008/0187101 A1 | 8/2008 | Gertner |
| 2008/0188864 A1 | 8/2008 | Ducharme |
| 2008/0196533 A1 | 8/2008 | Bergamasco et al. |
| 2008/0214925 A1 | 9/2008 | Wilson et al. |
| 2008/0228104 A1 | 9/2008 | Uber et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0262480 A1 | 10/2008 | Stahler et al. |
| 2008/0262513 A1 | 10/2008 | Stahler et al. |
| 2008/0287963 A1* | 11/2008 | Rogers .................. A61B 1/009 606/130 |
| 2008/0300592 A1 | 12/2008 | Weitzner et al. |
| 2008/0302200 A1 | 12/2008 | Tobey |
| 2008/0312521 A1 | 12/2008 | Solomon |
| 2009/0005768 A1 | 1/2009 | Sharareh |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck et al. |
| 2009/0062602 A1 | 3/2009 | Rosenberg et al. |
| 2009/0082634 A1 | 3/2009 | Kathrani et al. |
| 2009/0082722 A1 | 3/2009 | Munger et al. |
| 2009/0088772 A1* | 4/2009 | Blumenkranz ........ A61B 34/37 606/130 |
| 2009/0088774 A1 | 4/2009 | Swarup et al. |
| 2009/0098971 A1 | 4/2009 | Ho et al. |
| 2009/0105645 A1 | 4/2009 | Kidd et al. |
| 2009/0105723 A1 | 4/2009 | Dillinger |
| 2009/0131885 A1 | 5/2009 | Akahoshi |
| 2009/0138025 A1 | 5/2009 | Stahler et al. |
| 2009/0161827 A1 | 6/2009 | Gertner et al. |
| 2009/0163948 A1 | 6/2009 | Sunaoshi |
| 2009/0171371 A1 | 7/2009 | Nixon |
| 2009/0192510 A1 | 7/2009 | Bahney |
| 2009/0192524 A1 | 7/2009 | Ltkowitz |
| 2009/0227506 A1 | 9/2009 | Hogenhaug et al. |
| 2009/0227998 A1 | 9/2009 | Aljuri |
| 2009/0247944 A1 | 10/2009 | Kirschenman et al. |
| 2009/0248039 A1 | 10/2009 | Cooper et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas et al. |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081965 A1 | 4/2010 | Mugan et al. |
| 2010/0082017 A1 | 4/2010 | Zickler et al. |
| 2010/0082041 A1 | 4/2010 | Prisco |
| 2010/0125284 A1 | 5/2010 | Tanner et al. |
| 2010/0130923 A1 | 5/2010 | Cleary et al. |
| 2010/0130987 A1 | 5/2010 | Wenderow et al. |
| 2010/0137846 A1 | 6/2010 | Desai et al. |
| 2010/0175701 A1 | 7/2010 | Reis et al. |
| 2010/0179632 A1 | 7/2010 | Bruszewski et al. |
| 2010/0204605 A1 | 8/2010 | Blakley et al. |
| 2010/0204646 A1 | 8/2010 | Plicchi et al. |
| 2010/0210923 A1 | 8/2010 | Li et al. |
| 2010/0217235 A1 | 8/2010 | Thorstenson et al. |
| 2010/0225209 A1 | 9/2010 | Goldberg et al. |
| 2010/0228191 A1 | 9/2010 | Alvarez et al. |
| 2010/0228249 A1 | 9/2010 | Mohr et al. |
| 2010/0248177 A1 | 9/2010 | Mangelberger et al. |
| 2010/0249506 A1 | 9/2010 | Prisco et al. |
| 2010/0268211 A1 | 10/2010 | Manwaring et al. |
| 2010/0274078 A1 | 10/2010 | Kim et al. |
| 2010/0312141 A1 | 12/2010 | Keast et al. |
| 2010/0331856 A1 | 12/2010 | Carlson et al. |
| 2010/0331858 A1 | 12/2010 | Simaan et al. |
| 2010/0332033 A1 | 12/2010 | Diolaiti |
| 2011/0009863 A1 | 1/2011 | Stanislaw |
| 2011/0015483 A1 | 1/2011 | Barbagli et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0160713 A1 | 6/2011 | Neuberger |
| 2011/0160745 A1 | 6/2011 | Fielding |
| 2011/0167611 A1 | 7/2011 | Williams |
| 2011/0184391 A1 | 7/2011 | Aljuri |
| 2011/0208211 A1 | 8/2011 | Whitfield et al. |
| 2011/0213362 A1 | 9/2011 | Cunningham et al. |
| 2011/0224660 A1 | 9/2011 | Neuberger et al. |
| 2011/0238064 A1 | 9/2011 | Williams et al. |
| 2011/0238083 A1 | 9/2011 | Moll et al. |
| 2011/0257641 A1 | 10/2011 | Hastings et al. |
| 2011/0261183 A1 | 10/2011 | Ma et al. |
| 2011/0270084 A1 | 11/2011 | Choi et al. |
| 2011/0270273 A1 | 11/2011 | Moll et al. |
| 2011/0276085 A1 | 11/2011 | Krzyzanowski |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2011/0313343 A1 | 12/2011 | Milutinovic et al. |
| 2012/0004576 A1 | 1/2012 | Govari et al. |
| 2012/0048759 A1 | 3/2012 | Disch et al. |
| 2012/0069167 A1 | 3/2012 | Liu et al. |
| 2012/0071719 A1 | 3/2012 | Shanley et al. |
| 2012/0071821 A1 | 3/2012 | Yu |
| 2012/0071894 A1 | 3/2012 | Tanner et al. |
| 2012/0071895 A1 | 3/2012 | Stahler et al. |

(56) References Cited

U.S. PATENT DOCUMENTS

| | | |
|---|---|---|
| 2012/0132018 A1 | 5/2012 | Tang |
| 2012/0136372 A1 | 5/2012 | Girbau et al. |
| 2012/0136419 A1 | 5/2012 | Zarembo et al. |
| 2012/0138586 A1 | 6/2012 | Webster et al. |
| 2012/0138660 A1 | 6/2012 | Shelton, IV et al. |
| 2012/0143226 A1 | 6/2012 | Belson et al. |
| 2012/0150154 A1 | 6/2012 | Brisson et al. |
| 2012/0182409 A1 | 7/2012 | Moriyama et al. |
| 2012/0186194 A1 | 7/2012 | Schlieper |
| 2012/0191107 A1 | 7/2012 | Tanner et al. |
| 2012/0209315 A1 | 8/2012 | Amat |
| 2012/0217457 A1 | 8/2012 | Schena et al. |
| 2012/0232342 A1 | 9/2012 | Reydel |
| 2012/0232476 A1 | 9/2012 | Bhat et al. |
| 2012/0239012 A1 | 9/2012 | Laurent et al. |
| 2012/0253277 A1 | 10/2012 | Tah et al. |
| 2012/0253332 A1 | 10/2012 | Moll |
| 2012/0259320 A1 | 10/2012 | Loesel et al. |
| 2012/0277730 A1 | 11/2012 | Salahieh |
| 2012/0283747 A1 | 11/2012 | Popovic |
| 2012/0296318 A1 | 11/2012 | Wellhoefer et al. |
| 2013/0006144 A1 | 1/2013 | Clancy et al. |
| 2013/0018400 A1 | 1/2013 | Milton et al. |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0066335 A1 | 3/2013 | Barwinkel |
| 2013/0085442 A1 | 4/2013 | Shtul et al. |
| 2013/0085486 A1 | 4/2013 | Boutoussov et al. |
| 2013/0096422 A1 | 4/2013 | Boctor et al. |
| 2013/0096574 A1 | 4/2013 | Kang et al. |
| 2013/0110042 A1 | 5/2013 | Humphreys et al. |
| 2013/0110107 A1 | 5/2013 | Smith et al. |
| 2013/0114148 A1 | 5/2013 | Aschwanden et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0172738 A1 | 7/2013 | Bencteux et al. |
| 2013/0190741 A1 | 7/2013 | Moll et al. |
| 2013/0190796 A1 | 7/2013 | Tilson et al. |
| 2013/0204124 A1 | 8/2013 | Duindam |
| 2013/0225997 A1 | 8/2013 | Dillard et al. |
| 2013/0226151 A1 | 8/2013 | Suehara |
| 2013/0226161 A1 | 8/2013 | Hickenbotham |
| 2013/0231678 A1 | 9/2013 | Wenderow |
| 2013/0233908 A1 | 9/2013 | Knodel |
| 2013/0253267 A1 | 9/2013 | Collins |
| 2013/0303876 A1 | 11/2013 | Gelfand et al. |
| 2013/0304084 A1 | 11/2013 | Beira et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345519 A1 | 12/2013 | Piskun et al. |
| 2013/0345686 A1 | 12/2013 | Brown et al. |
| 2014/0000411 A1 | 1/2014 | Shelton, IV et al. |
| 2014/0005681 A1 | 1/2014 | Gee et al. |
| 2014/0039517 A1 | 2/2014 | Bowling |
| 2014/0039681 A1 | 2/2014 | Bowling et al. |
| 2014/0046308 A1 | 2/2014 | Bischoff et al. |
| 2014/0051985 A1 | 2/2014 | Fan et al. |
| 2014/0058365 A1 | 2/2014 | Bille et al. |
| 2014/0058404 A1 | 2/2014 | Hammack et al. |
| 2014/0058428 A1 | 2/2014 | Christopher et al. |
| 2014/0066944 A1 | 3/2014 | Taylor et al. |
| 2014/0069437 A1 | 3/2014 | Reis et al. |
| 2014/0094825 A1 | 4/2014 | Flaherty et al. |
| 2014/0100445 A1 | 4/2014 | Stenzel et al. |
| 2014/0142591 A1 | 5/2014 | Alvarez et al. |
| 2014/0163318 A1 | 6/2014 | Swanstrom |
| 2014/0163736 A1 | 6/2014 | Azizian |
| 2014/0166023 A1 | 6/2014 | Kishi |
| 2014/0171778 A1 | 6/2014 | Tsusaka |
| 2014/0180063 A1 | 6/2014 | Zhao |
| 2014/0194859 A1 | 7/2014 | Ianchulev |
| 2014/0194905 A1 | 7/2014 | Kappel |
| 2014/0222019 A1 | 8/2014 | Brudnick |
| 2014/0222207 A1 | 8/2014 | Bowling et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276723 A1 | 9/2014 | Parihar et al. |
| 2014/0276935 A1 | 9/2014 | Yu |
| 2014/0276936 A1 | 9/2014 | Kokish et al. |
| 2014/0276956 A1 | 9/2014 | Crainich |
| 2014/0277334 A1 | 9/2014 | Yu et al. |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson |
| 2015/0028195 A1 | 1/2015 | King et al. |
| 2015/0051592 A1 | 2/2015 | Kintz et al. |
| 2015/0073439 A1 | 3/2015 | Dannaher |
| 2015/0080879 A1 | 3/2015 | Trees |
| 2015/0090063 A1 | 4/2015 | Lantermann et al. |
| 2015/0101442 A1 | 4/2015 | Romo et al. |
| 2015/0119634 A1 | 4/2015 | Jones |
| 2015/0119637 A1 | 4/2015 | Alvarez et al. |
| 2015/0119638 A1 | 4/2015 | Yu et al. |
| 2015/0127045 A1 | 5/2015 | Prestel |
| 2015/0133960 A1 | 5/2015 | Lohmeier |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164522 A1 | 6/2015 | Budiman |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0182250 A1 | 7/2015 | Conlon et al. |
| 2015/0190204 A1 | 7/2015 | Popovi |
| 2015/0201917 A1 | 7/2015 | Snow et al. |
| 2015/0202085 A1 | 7/2015 | Lemonis et al. |
| 2015/0231364 A1 | 8/2015 | Blanchard |
| 2015/0314110 A1 | 11/2015 | Park |
| 2015/0335480 A1 | 11/2015 | Alvarez et al. |
| 2015/0366629 A1 | 12/2015 | Bowling |
| 2015/0374445 A1 | 12/2015 | Gombert et al. |
| 2015/0374446 A1 | 12/2015 | Malackowski |
| 2016/0000512 A1 | 1/2016 | Gombert et al. |
| 2016/0001038 A1 | 1/2016 | Romo et al. |
| 2016/0022289 A1 | 1/2016 | Wan et al. |
| 2016/0022466 A1 | 1/2016 | Pedtke |
| 2016/0030014 A1 | 2/2016 | McWeeney et al. |
| 2016/0030073 A1 | 2/2016 | Isakov et al. |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0124220 A1 | 5/2016 | Bueeler et al. |
| 2016/0128781 A1 | 5/2016 | Blohm et al. |
| 2016/0151122 A1 | 6/2016 | Alvarez et al. |
| 2016/0157945 A1 | 6/2016 | Madhani |
| 2016/0158490 A1 | 6/2016 | Leeflang et al. |
| 2016/0166234 A1 | 6/2016 | Zhang |
| 2016/0183841 A1 | 6/2016 | Duindam et al. |
| 2016/0184032 A1 | 6/2016 | Romo et al. |
| 2016/0192860 A1 | 7/2016 | Allenby |
| 2016/0199984 A1 | 7/2016 | Lohmeier et al. |
| 2016/0206389 A1 | 7/2016 | Miller |
| 2016/0213435 A1 | 7/2016 | Hourtash |
| 2016/0223753 A1* | 8/2016 | Noonan ............... G02B 6/3624 |
| 2016/0235478 A1 | 8/2016 | Bonneau et al. |
| 2016/0235495 A1 | 8/2016 | Wallace et al. |
| 2016/0242858 A1 | 8/2016 | Moctezuma de la Barrera et al. |

(56) References Cited

U.S. PATENT DOCUMENTS

| | | |
|---|---|---|
| 2016/0249932 A1 | 9/2016 | Rogers et al. |
| 2016/0270865 A1 | 9/2016 | Landey et al. |
| 2016/0270866 A1 | 9/2016 | Yu et al. |
| 2016/0279394 A1 | 9/2016 | Moll et al. |
| 2016/0287279 A1 | 10/2016 | Bovay et al. |
| 2016/0287840 A1 | 10/2016 | Jiang |
| 2016/0296294 A1 | 10/2016 | Moll et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0367324 A1 | 12/2016 | Sato et al. |
| 2016/0374541 A1 | 12/2016 | Agrawal et al. |
| 2017/0000577 A1 | 1/2017 | Bowling |
| 2017/0007279 A1 | 1/2017 | Sharma |
| 2017/0007337 A1 | 1/2017 | Dan |
| 2017/0020615 A1 | 1/2017 | Koenig et al. |
| 2017/0049471 A1 | 2/2017 | Gaffney et al. |
| 2017/0055995 A1 | 3/2017 | Weier |
| 2017/0065227 A1 | 3/2017 | Marrs et al. |
| 2017/0065357 A1 | 3/2017 | Schuh |
| 2017/0065363 A1 | 3/2017 | Schuh et al. |
| 2017/0065364 A1 | 3/2017 | Schuh et al. |
| 2017/0065365 A1 | 3/2017 | Schuh |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer et al. |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo et al. |
| 2017/0119481 A1 | 5/2017 | Romo et al. |
| 2017/0127911 A1 | 5/2017 | Yamamoto et al. |
| 2017/0135706 A1 | 5/2017 | Frey |
| 2017/0151028 A1 | 6/2017 | Ogawa et al. |
| 2017/0151416 A1 | 6/2017 | Kutikov |
| 2017/0165009 A1 | 6/2017 | Chaplin et al. |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0172680 A1 | 6/2017 | Bowling |
| 2017/0202627 A1 | 7/2017 | Sramek et al. |
| 2017/0202827 A1 | 7/2017 | Genkin et al. |
| 2017/0209073 A1 | 7/2017 | Sramek et al. |
| 2017/0252096 A1 | 9/2017 | Felder |
| 2017/0258534 A1 | 9/2017 | Hourtash |
| 2017/0265923 A1 | 9/2017 | Privitera et al. |
| 2017/0265954 A1 | 9/2017 | Burbank |
| 2017/0281049 A1 | 10/2017 | Yamamoto |
| 2017/0290631 A1 | 10/2017 | Lee et al. |
| 2017/0319289 A1 | 11/2017 | Neff |
| 2017/0325932 A1 | 11/2017 | Hoelzle |
| 2017/0333147 A1 | 11/2017 | Bernstein |
| 2017/0333679 A1 | 11/2017 | Jiang et al. |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0049824 A1 | 2/2018 | Harris |
| 2018/0055583 A1 | 3/2018 | Schuh et al. |
| 2018/0056044 A1 | 3/2018 | Choi et al. |
| 2018/0079090 A1 | 3/2018 | Koenig et al. |
| 2018/0080841 A1 | 3/2018 | Cordoba |
| 2018/0104820 A1 | 4/2018 | Troy et al. |
| 2018/0116735 A1 | 5/2018 | Tierney et al. |
| 2018/0140371 A1 | 5/2018 | Hares et al. |
| 2018/0168681 A1 | 6/2018 | Kirk et al. |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0193049 A1 | 7/2018 | Heck et al. |
| 2018/0206927 A1 | 7/2018 | Prisco et al. |
| 2018/0206931 A1 | 7/2018 | Scheib |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0250083 A1 | 9/2018 | Schuh et al. |
| 2018/0250085 A1 | 9/2018 | Simi |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296285 A1 | 10/2018 | Simi et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0015166 A1 | 1/2019 | Mahoney |
| 2019/0069962 A1 | 3/2019 | Tabandeh et al. |
| 2019/0083183 A1 | 3/2019 | Moll et al. |
| 2019/0099231 A1 | 4/2019 | Bruehwiler |
| 2019/0099232 A1 | 4/2019 | Soto et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0117320 A1 | 4/2019 | Shoham et al. |
| 2019/0117324 A1 | 4/2019 | Hibner |
| 2019/0125465 A1 | 5/2019 | Evans et al. |
| 2019/0142537 A1 | 5/2019 | Covington et al. |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0191967 A1 | 6/2019 | Yamamoto et al. |
| 2019/0192249 A1 | 6/2019 | Bowling |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223967 A1 | 7/2019 | Abbott |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0231458 A1 | 8/2019 | DiMaio |
| 2019/0231460 A1 | 8/2019 | DiMaio |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |

(56) References Cited

U.S. PATENT DOCUMENTS

| | | |
|---|---|---|
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0008874 A1 | 1/2020 | Barbagli et al. |
| 2020/0022767 A1 | 1/2020 | Hill et al. |
| 2020/0030046 A1 | 1/2020 | Bowling |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez, Jr. et al. |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho et al. |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0138531 A1 | 5/2020 | Chaplin |
| 2020/0146769 A1 | 5/2020 | Eyre |
| 2020/0155245 A1 | 5/2020 | Yu |
| 2020/0155801 A1 | 5/2020 | Kokish |
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305922 A1 | 10/2020 | Yan et al. |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo et al. |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0383735 A1 | 12/2020 | Lewis et al. |
| 2020/0405317 A1 | 12/2020 | Wallace |
| 2020/0405411 A1 | 12/2020 | Draper et al. |
| 2020/0405413 A1 | 12/2020 | Kokish |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |
| 2021/0007819 A1 | 1/2021 | Schuh |
| 2021/0008341 A1 | 1/2021 | Landey et al. |
| 2021/0045819 A1 | 2/2021 | Castillo et al. |
| 2021/0045822 A1 | 2/2021 | Landey et al. |
| 2021/0045823 A1 | 2/2021 | Landey et al. |
| 2021/0045824 A1 | 2/2021 | Landey et al. |
| 2021/0059766 A1 | 3/2021 | Graetzel et al. |
| 2021/0121052 A1 | 4/2021 | Graetzel et al. |
| 2021/0169588 A1 | 6/2021 | Graetzel et al. |
| 2021/0178032 A1 | 6/2021 | Hsu et al. |
| 2021/0196293 A1 | 7/2021 | Lin et al. |
| 2021/0196312 A1 | 7/2021 | Plewe et al. |
| 2021/0196399 A1 | 7/2021 | Ayvali et al. |
| 2021/0196410 A1 | 7/2021 | Hsu et al. |

FOREIGN PATENT DOCUMENTS

| | | |
|---|---|---|
| AU | 2018290831 A1 | 12/2019 |
| AU | 2018292606 A1 | 1/2020 |
| AU | 2018347472 A1 | 4/2020 |
| AU | 2018378808 A1 | 5/2020 |
| AU | 2019347767 A1 | 4/2021 |
| AU | 2021204979 A1 | 8/2021 |
| CN | 101161426 | 4/2008 |
| CN | 101443069 | 5/2009 |
| CN | 100515347 | 7/2009 |
| CN | 101495023 A | 7/2009 |
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103298414 | 9/2013 |
| CN | 103735313 | 4/2014 |
| CN | 104619281 | 5/2015 |
| CN | 102947730 B | 7/2015 |
| CN | 105005103 A | 10/2015 |
| CN | 105147393 | 12/2015 |
| CN | 105559850 | 5/2016 |
| CN | 105559886 | 5/2016 |
| CN | 205729413 | 11/2016 |
| CN | 107257665 A | 10/2017 |
| CN | 108882837 A | 11/2018 |
| CN | 108990412 A | 12/2018 |
| CN | 109688894 A | 4/2019 |
| CN | 208974012 U | 6/2019 |
| CN | 110831653 A | 2/2020 |
| CN | 110868903 A | 3/2020 |
| CN | 110891514 A | 3/2020 |
| CN | 111386450 A | 7/2020 |
| CN | 111432856 A | 7/2020 |
| CN | 112472007 A | 3/2021 |
| CN | 108369450 B | 4/2021 |
| CN | 112770690 A | 5/2021 |
| CN | 112804946 A | 5/2021 |
| DE | 19649082 | 1/1998 |
| DE | 102004020465 | 9/2005 |
| DE | 102015016152 A1 | 6/2017 |
| EP | 1 321 106 | 6/2003 |
| EP | 1 442 720 | 8/2004 |
| EP | 1321106 B1 | 10/2005 |
| EP | 1 849 423 | 10/2007 |
| EP | 1849423 A3 | 12/2007 |
| EP | 2043501 A2 | 4/2009 |
| EP | 2046227 A2 | 4/2009 |
| EP | 2210066 A2 | 7/2010 |
| EP | 2239600 A1 | 10/2010 |
| EP | 2 567 670 | 3/2013 |
| EP | 2923669 A1 | 9/2015 |
| EP | 3 025 630 | 6/2016 |
| EP | 3387514 B1 | 6/2019 |
| EP | 3518724 A1 | 8/2019 |
| EP | 2577363 B1 | 7/2020 |
| EP | 3676587 A1 | 7/2020 |
| EP | 3752085 A1 | 12/2020 |
| EP | 3600031 A4 | 1/2021 |
| EP | 3644820 A4 | 3/2021 |
| EP | 3645100 A4 | 3/2021 |
| EP | 3820373 A1 | 5/2021 |
| EP | 3856064 A1 | 8/2021 |
| EP | 3684438 A4 | 9/2021 |

(56) References Cited

FOREIGN PATENT DOCUMENTS

| | | |
|---|---|---|
| JP | 07-136173 | 5/1995 |
| JP | 2005-270464 | 10/2005 |
| JP | 2005270464 A | 10/2005 |
| JP | 2009-139187 | 6/2009 |
| JP | 2010-046384 | 3/2010 |
| JP | 2014-159071 | 9/2014 |
| JP | 2015-181495 | 10/2015 |
| JP | 2020512102 A | 4/2020 |
| JP | 2020526252 A | 8/2020 |
| JP | 2020526254 A | 8/2020 |
| JP | 2019531807 | 11/2020 |
| JP | 2020536754 A | 12/2020 |
| JP | 2021505287 A | 2/2021 |
| JP | 2021513436 A | 5/2021 |
| KR | 1020190119541 A | 10/2019 |
| KR | 20190134968 A | 12/2019 |
| KR | 20200023640 A | 3/2020 |
| KR | 20200024873 A | 3/2020 |
| KR | 20200071744 A | 6/2020 |
| KR | 20200099127 A | 8/2020 |
| KR | 20200122337 A | 10/2020 |
| KR | 20210042134 A | 4/2021 |
| KR | 20210073542 A | 6/2021 |
| KR | 102297011 B1 | 9/2021 |
| WO | WO 94/14494 | 7/1994 |
| WO | WO 96/22591 | 7/1996 |
| WO | 9823216 A1 | 6/1998 |
| WO | WO 02/74178 | 9/2002 |
| WO | 2007005976 A1 | 1/2007 |
| WO | WO 07/088208 | 8/2007 |
| WO | 2007136984 A2 | 11/2007 |
| WO | WO 07/146987 | 12/2007 |
| WO | 2008014425 A2 | 1/2008 |
| WO | 2008031077 A2 | 3/2008 |
| WO | 2008017080 A3 | 10/2008 |
| WO | 2008157399 A1 | 12/2008 |
| WO | 2008101228 A3 | 1/2009 |
| WO | 2009023801 A1 | 2/2009 |
| WO | 2009045697 A2 | 4/2009 |
| WO | 2009064629 A2 | 5/2009 |
| WO | WO 09/092059 | 7/2009 |
| WO | WO 10/133982 | 11/2010 |
| WO | 2010133982 A3 | 1/2011 |
| WO | 2011008922 A2 | 1/2011 |
| WO | WO 11/005335 | 1/2011 |
| WO | 2011150526 A1 | 12/2011 |
| WO | WO 11/161218 | 12/2011 |
| WO | 2012040233 A2 | 3/2012 |
| WO | WO 12/037506 | 3/2012 |
| WO | 2012167043 A2 | 12/2012 |
| WO | WO 13/107468 | 7/2013 |
| WO | 2013130895 A1 | 9/2013 |
| WO | 2013154708 A1 | 10/2013 |
| WO | WO 13/179600 | 12/2013 |
| WO | WO 15/127231 | 8/2015 |
| WO | 2015141635 A1 | 9/2015 |
| WO | WO 15/153174 | 10/2015 |
| WO | 2016014414 A1 | 1/2016 |
| WO | 2016140712 A1 | 9/2016 |
| WO | WO 16/137612 | 9/2016 |
| WO | WO 17/059412 | 4/2017 |
| WO | 2017075574 A1 | 5/2017 |
| WO | 2017097399 A1 | 6/2017 |
| WO | WO 17/114855 | 7/2017 |
| WO | WO 17/151993 | 9/2017 |
| WO | WO 17/156070 | 9/2017 |
| WO | 2018064394 A1 | 4/2018 |
| WO | 2018069679 A1 | 4/2018 |
| WO | WO 18/069679 | 4/2018 |
| WO | WO 18/094191 | 5/2018 |
| WO | 2018183727 A1 | 10/2018 |
| WO | WO 18/189722 | 10/2018 |
| WO | 2019005872 A1 | 1/2019 |
| WO | 2019005992 A1 | 1/2019 |
| WO | 2019074669 A1 | 4/2019 |
| WO | 2019113389 A1 | 6/2019 |
| WO | 2019118368 A1 | 6/2019 |
| WO | 2019160865 A1 | 8/2019 |
| WO | 2020033318 A1 | 2/2020 |
| WO | 2020069430 A1 | 4/2020 |
| WO | 2021028889 A1 | 2/2021 |
| WO | 2021044297 A1 | 3/2021 |
| WO | 2021137071 A1 | 7/2021 |
| WO | 2021137106 A1 | 7/2021 |
| WO | 2021137108 A1 | 7/2021 |
| WO | 2021137109 A1 | 7/2021 |

OTHER PUBLICATIONS

Notice of Allowance for U.S. Appl. No. 16/355,437, dated Apr. 26, 2022, 10 pages.
Notice of Allowance for U.S. Appl. No. 17/121,167, dated May 4, 2022, 7 pages.
International search report and written opinion dated Dec. 18, 2020 in application No. PCT/IB2020/057704.
Notice of Allowance for U.S. Appl. No. 15/948,369, dated Dec. 14, 2021, 11 pages.
PCT Invitation to Pay Additional Fees, PCT Application No. PCT/US2016/059686, dated Dec. 8, 2016, 2 pages.
Notice of Allowance for U.S. Appl. No. 15/948,369, dated Sep. 7, 2022, 11 pages.
International Preliminary Report on Patentability and Written Opinion for Appl. No. PCT/IB2020/061905, dated Jul. 5, 2022, 7 pages.
Notice of Allowance for U.S. Appl. No. 16/355,437, dated Aug. 11, 2022, 10 pages.
Notice of Allowance for U.S. Appl. No. 16/865,904, dated Aug. 10, 2022, 8 pages.
Hernansanz et al, 2015, A multi-robot cooperation strategy for dexterous task oriented teleoperation, 2015, Elsevier, Robotics and Autonomous Systems, 68(205):156-172.
Mayo Clinic, Robotic Surgery, https://www.mayoclinic.org/tests-procedures/robotic-surgery/about/pac-20394974?p=1, downloaded from the internet on Jul. 12, 2018, 2 pp.
Ramezanifard et al, 2007, A Novel Modeling Approach for Collision Avoidance in Robotic Surgery, 2007 Science Publications, American Journal of Applied Sciences 4(9):693-699.
Advisory action for U.S. Appl. No. 15/948,351, dated Sep. 1, 2021, 3 pages.
AU Examination report for appl. No. 2016343849, dated Mar. 16, 2021, 5 pages.
Extended European Search Report for appl No. 16861031.9, dated Jun. 12, 2019, 8 pages.
International search report for PCT/IB2020/061905, dated Mar. 18, 2021, 8 pages.
Invitation to Pay Additional Fees in PCT appl No. PCT/US2016/059686, dated Dec. 8, 2016, 2 pages.
JP office action dated Dec. 1, 2020, for patent appl No. 2018-521951, 4 pages.
Notice of Acceptance for appl No. 2016343849, dated Aug. 5, 2021, 3 pages.
Notice of allowance for U.S. Appl. No. 15/948,369, dated Aug. 17, 2021, 10 pages.
Notice of allowance for U.S. Appl. No. 16/355,437, dated Oct. 28, 2021, 10 pages.
Notice of allowance for appl No. 1711167, dated Jul. 20, 2021, 7 pages.
Notice of allowance for U.S. Appl. No. 17/121,167, dated Apr. 6, 2021, 7 pages.
Notice of Allowance for U.S. Appl. No. 17/121,167, dated Nov. 10, 2021, 4 pages.
Notice of allowance for U.S. Appl. No. 17/121,167, dated Nov. 3, 2021, 7 pages.
Office action for U.S. Appl. No. 15/948,351, dated May 10, 2021, 11 pages.
Office action for U.S. Appl. No. 15/948,351, dated Nov. 16, 2020, 10 pages.
Office action for U.S. Appl. No. 15/948,351, dated Sep. 29, 2021, 17 pages.

(56) References Cited

OTHER PUBLICATIONS

Office action for U.S. Appl. No. 15/948,369, dated May 25, 2021, 14 pages.
Office action for U.S. Appl. No. 15/948,369, dated Nov. 20, 2020, 14 pages.
Office action for U.S. Appl. No. 16/865,904, dated Sep. 17, 2021, 13 pages.
Written opinion for PCT/IB2020/061905, dated Mar. 18, 2021, 6 pages.
AU Examination Report for Appl. No. 2021229251, dated Nov. 5, 2022, 3 pages.
Final Rejection for U.S. Appl. No. 16/865,904, dated Apr. 15, 2022, 14 pages.
International Preliminary Report on Patentability for PCT/US2016/059686 dated Feb. 17, 2017, 7 pages.
International Search Report for PCT/IB2020/057704 dated Feb. 18, 2021, 16 pages.
International Search Report for PCT/US2016/059686 dated Feb. 17, 2017, 4 pages.
Mayo Clinic, Robotic Surgery, https://www.mayoclinic.org/tests-procedures/robotic-surgery/about/pac- 20394974?p=1, downloaded from the internet on Jul. 12, 2018, 2 pgs.
Notice of Allowance for U.S. Appl. No. 15/948,351, dated Mar. 2, 2022, 10 pages.
Written Opinion of the International Search Authority for PCT/IB2020/057704 dated Feb. 18, 2021, 9 pages.
Written Opinion of the International Searching Authority for PCT/US2016/059686 dated Feb. 17, 2017, 6 pages.
AU Examination Report for Appl. No. 2021229251, dated May 5, 2023, 3 pages.
CN Office Action for Appl. No. 202080091164.3, dated Apr. 7, 2023, 9 pages.
Non-Final Rejection for U.S. Appl. No. 15/339,468 dated Jul. 6, 2017, 10 pages.
Non-Final Rejection for U.S. Appl. No. 15/339,468 dated Nov. 15, 2017, 14 pages.
Non-Final Rejection for U.S. Appl. No. 15/339,476 dated May 24, 2017, 8 pages.
Non-Final Rejection for U.S. Appl. No. 15/339,476 dated Oct. 25, 2017, 9 pages.
Notice of Allowance for U.S. Appl. No. 15/339,468 dated Dec. 27, 2017, 10 pages.
Notice of Allowance for U.S. Appl. No. 15/339,476 dated Dec. 18, 2017, 10 pages.
EP Search Report for Appl. No. 20851547.8, dated Jul. 12, 2023, 19 pages.
EP Search Report for Appl. No. 20851547.8, dated Oct. 13, 2023, 15 pages.

* cited by examiner

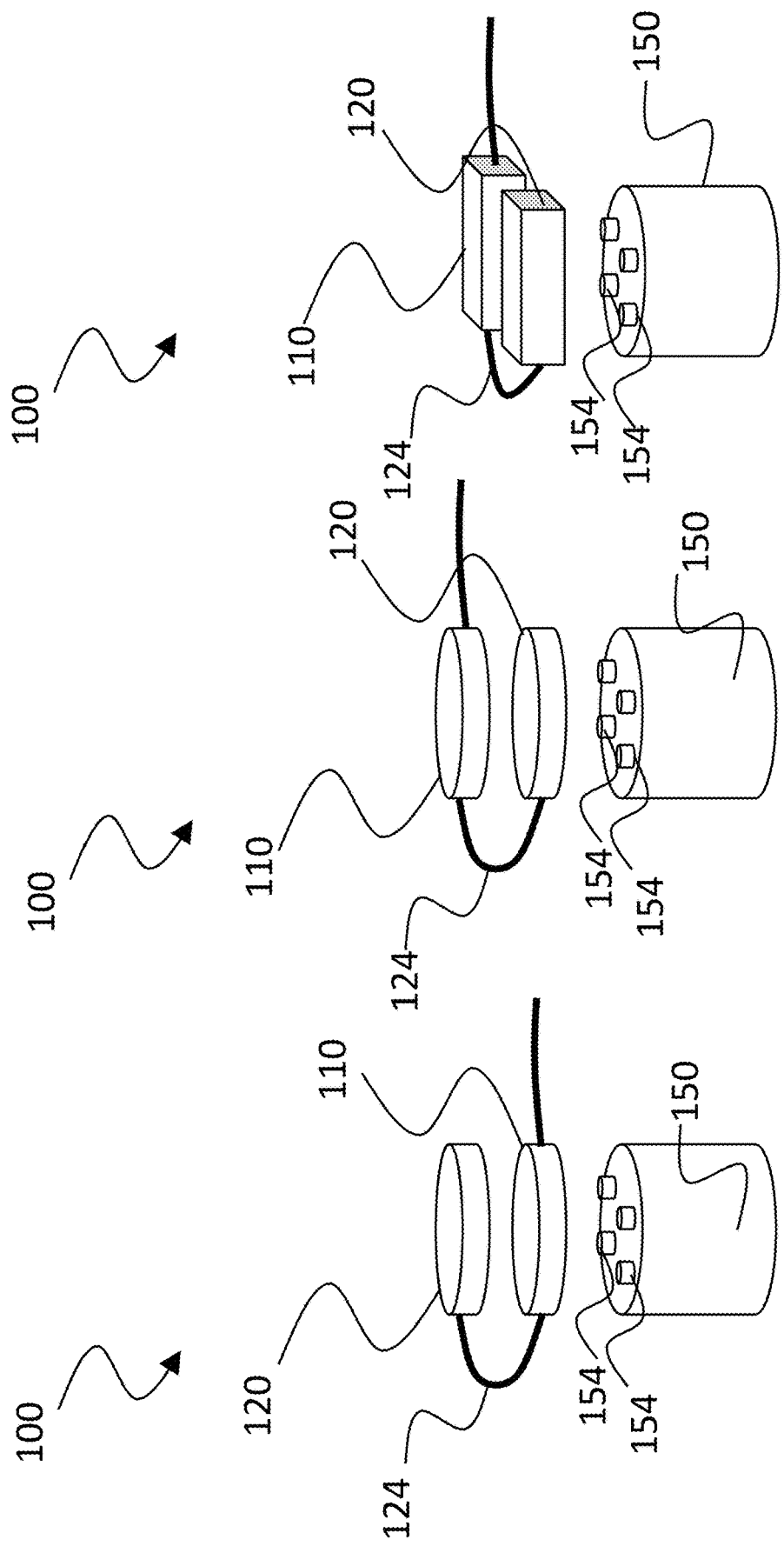

the robotic systems of FIGS. 1-10, such as the location of the instrument of FIGS. 16-18, in accordance to an example embodiment.
ROBOTIC MEDICAL SYSTEM HAVING MULTIPLE MEDICAL INSTRUMENTS

CROSS-REFERENCE TO RELATED APPLICATION(S)

This application claims the benefit of U.S. Provisional Application No. 62/887,569, filed Aug. 15, 2019, which is hereby incorporated by reference in its entirety.

TECHNICAL FIELD

The systems and methods disclosed herein are directed to medical instrument systems, and more particularly, to medical instruments that can be controllable manually or robotically.

BACKGROUND

Medical procedures, such as endoscopy, may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a thin, flexible tubular tool or instrument, known as an endoscope, is inserted into the patient through an orifice (such as a natural orifice) and advanced towards a tissue site identified for subsequent diagnosis and/or treatment. The medical instrument can be controllable and articulable to facilitate navigation through the anatomy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 21A-21E schematically show example medical instrument systems.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
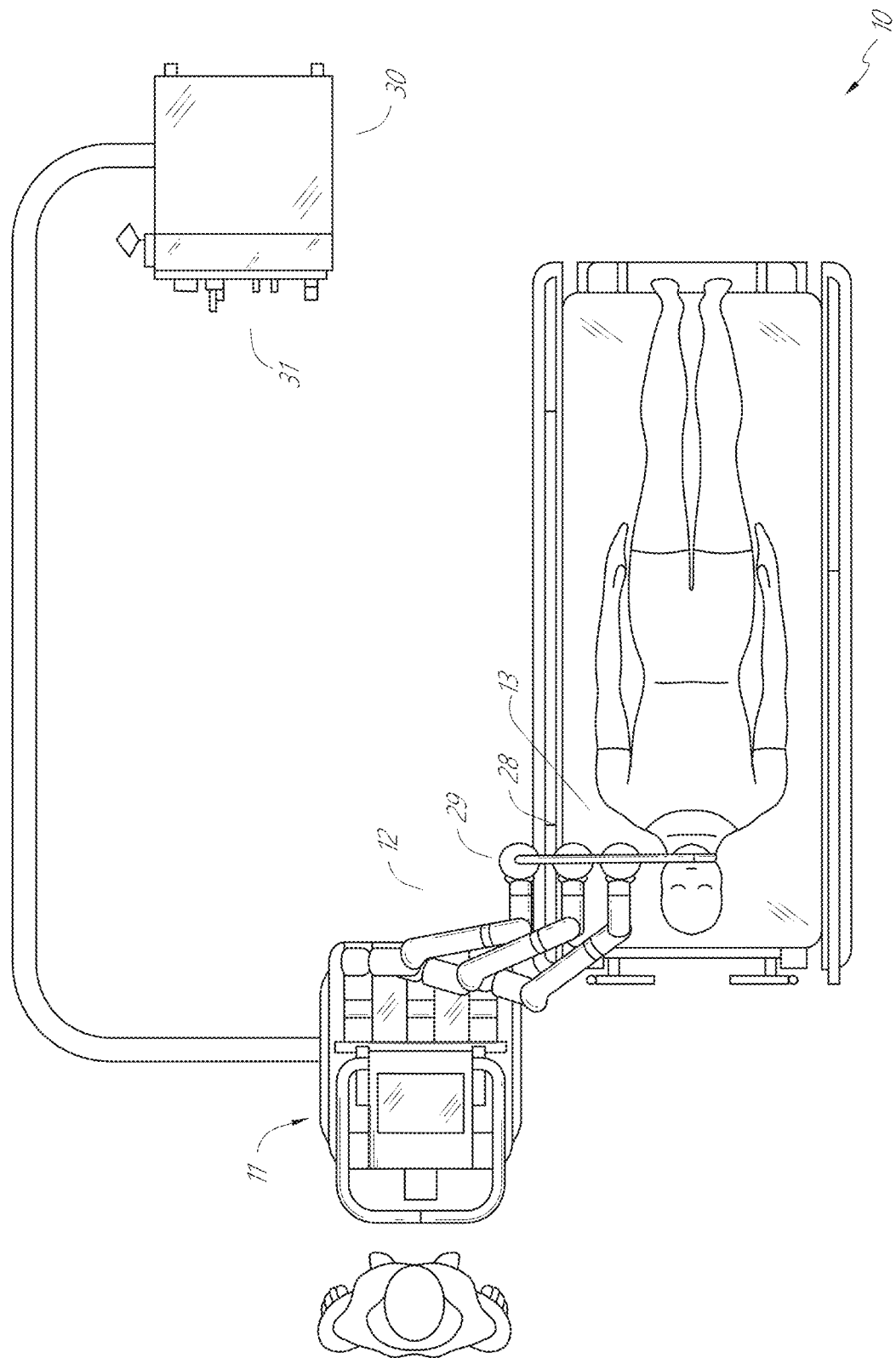
FIG. 1 illustrates an embodiment of a cart-based robotic system arranged for diagnostic and/or therapeutic bronchoscopy.
Figure 2:
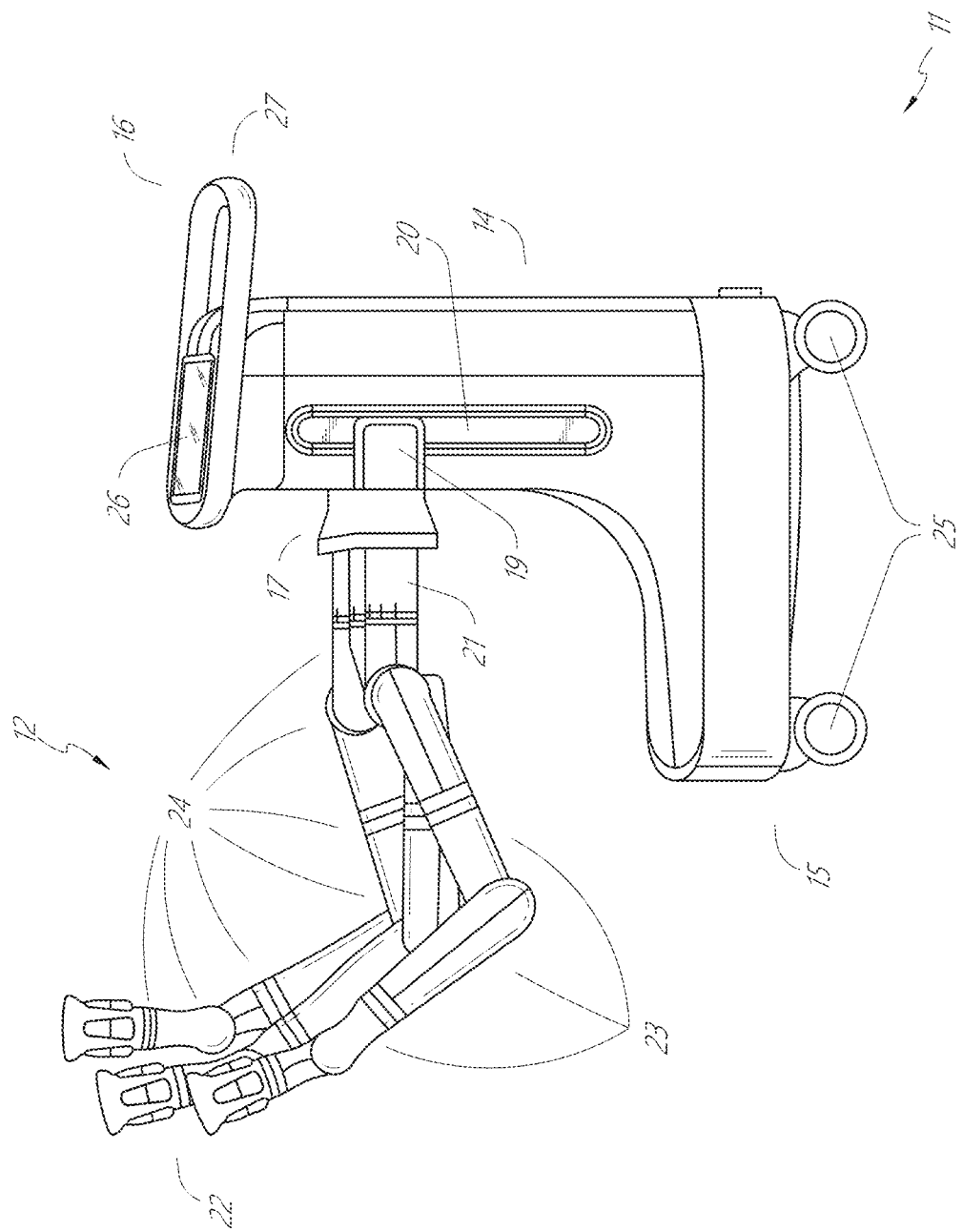
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
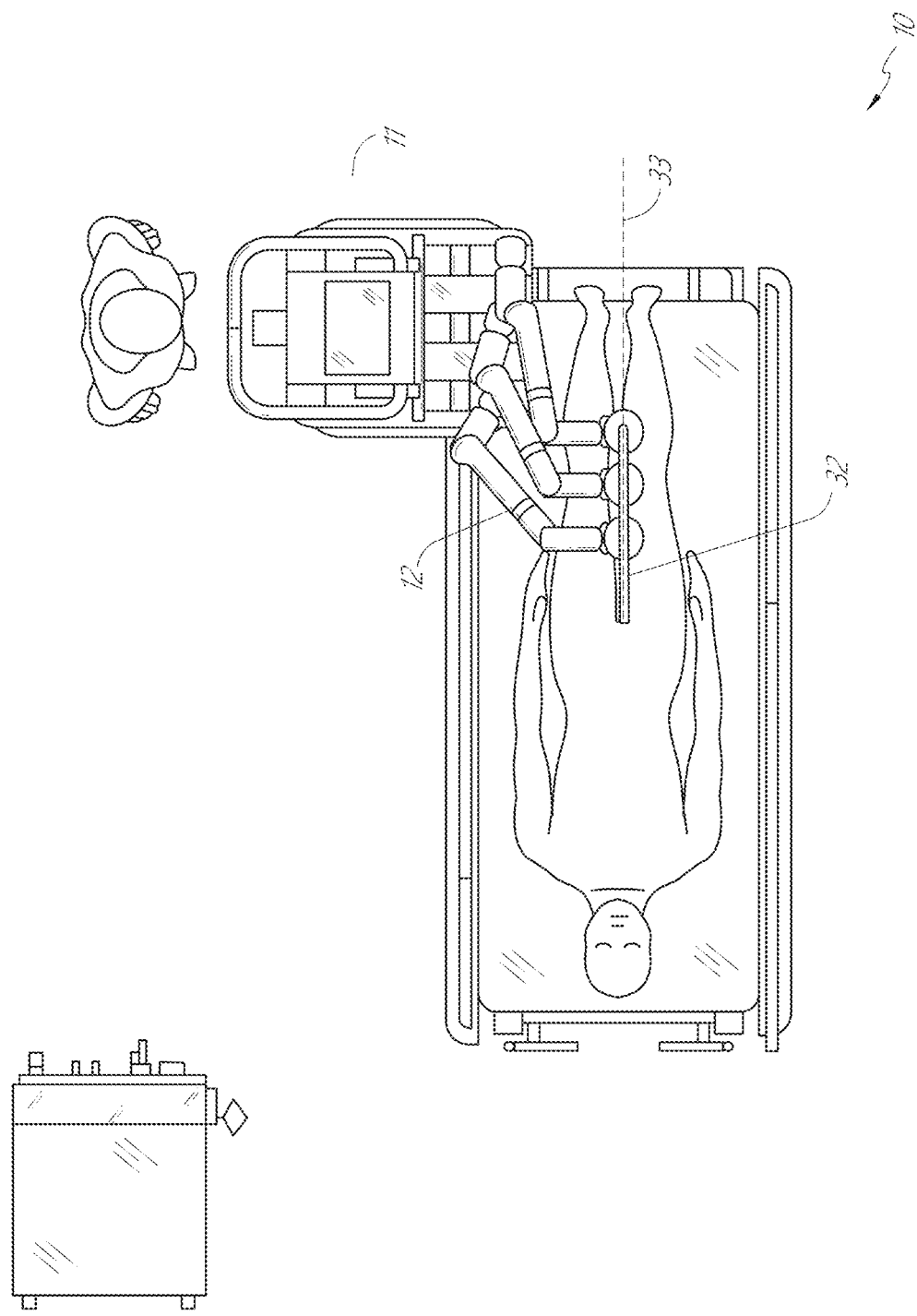
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
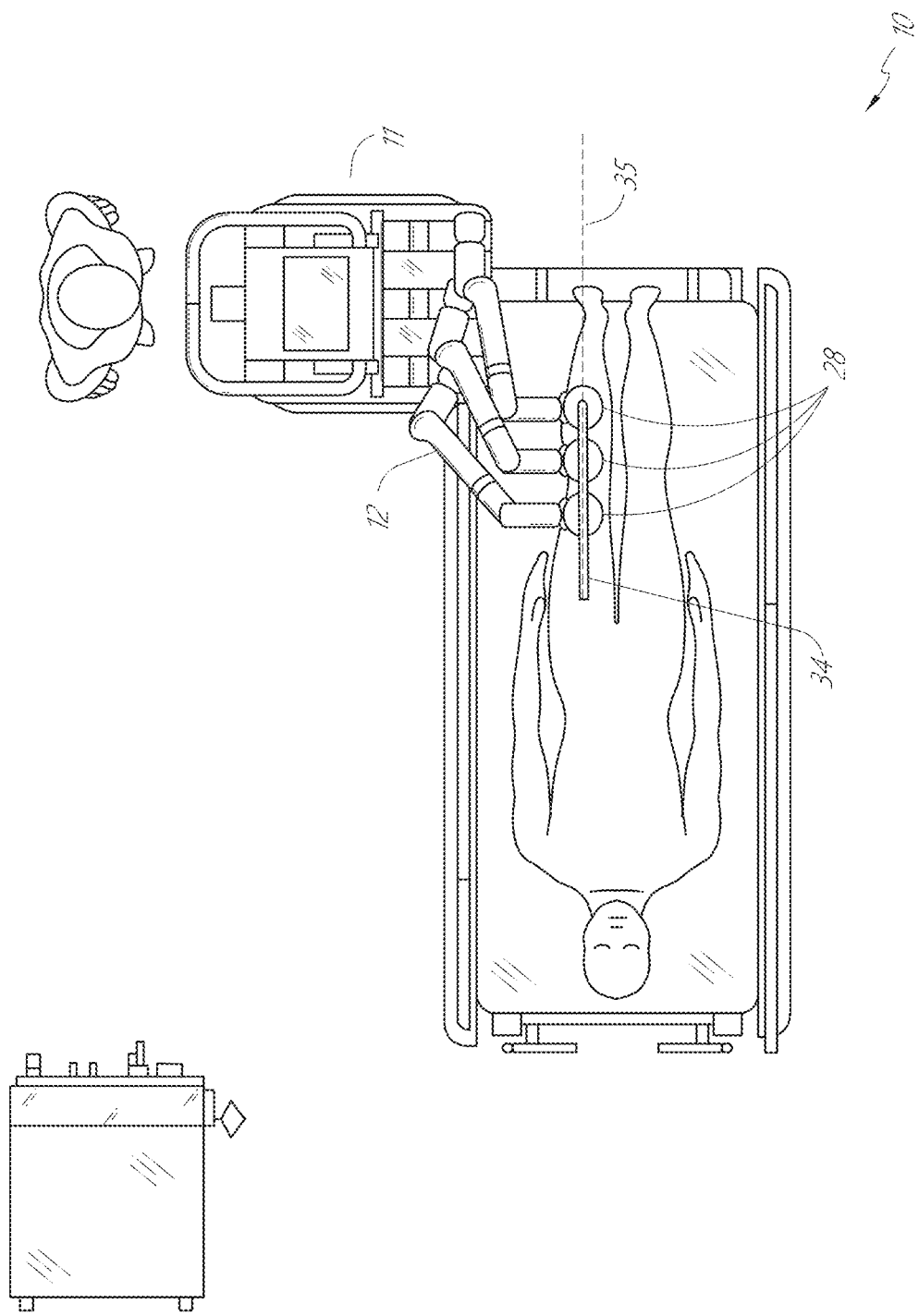
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
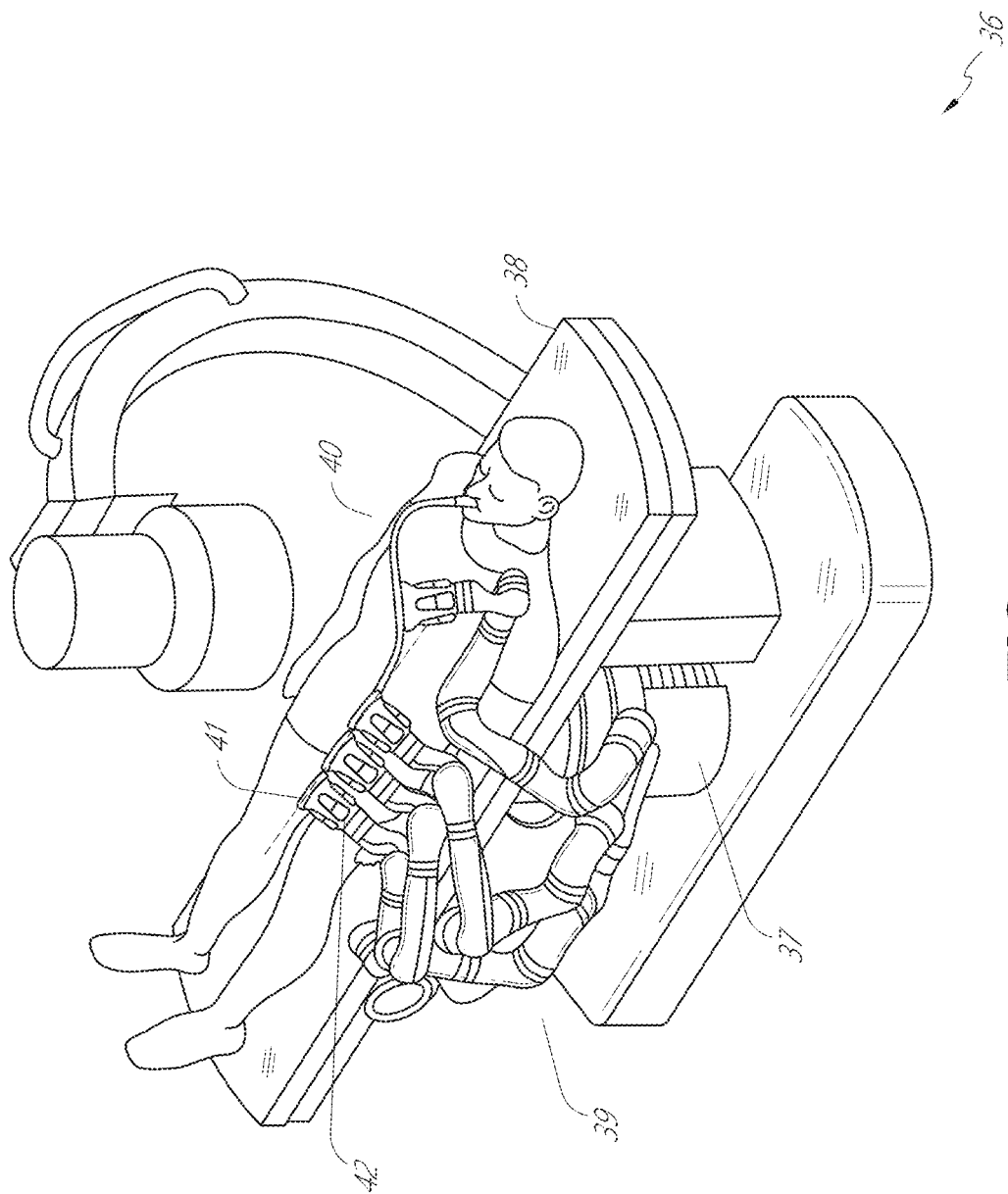
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
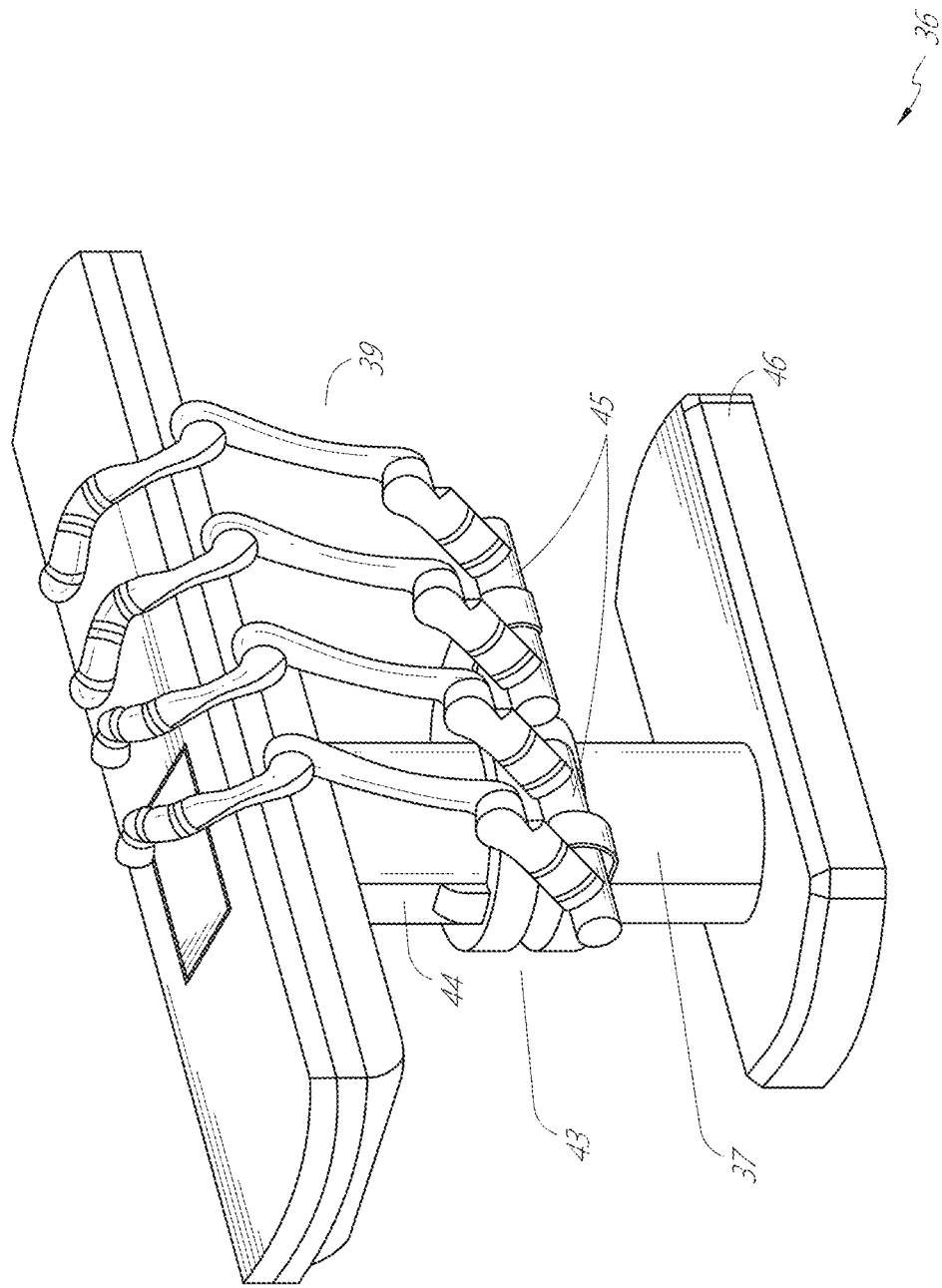
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
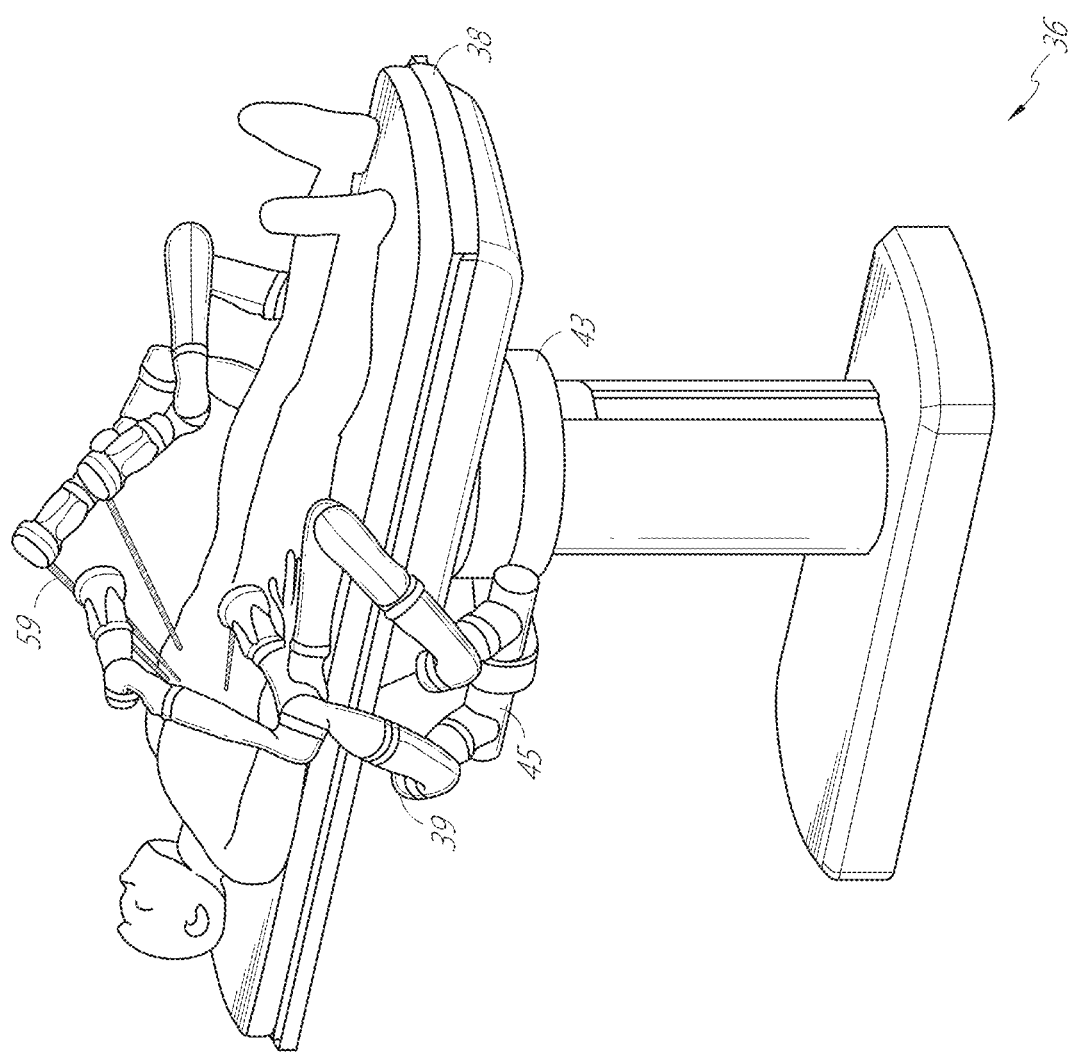
FIG. 9 illustrates an embodiment of a table-based robotic system configured for alaparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
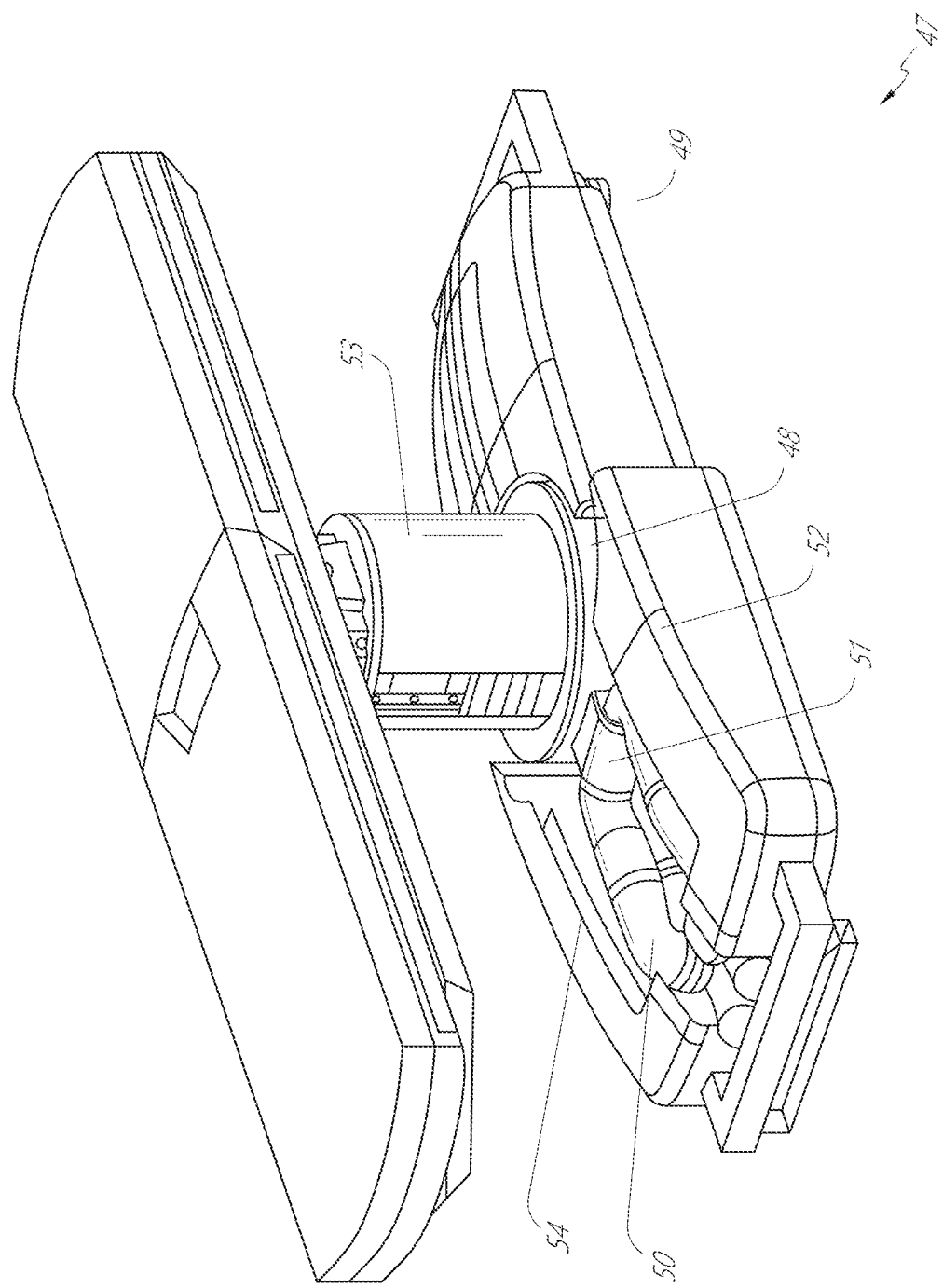
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
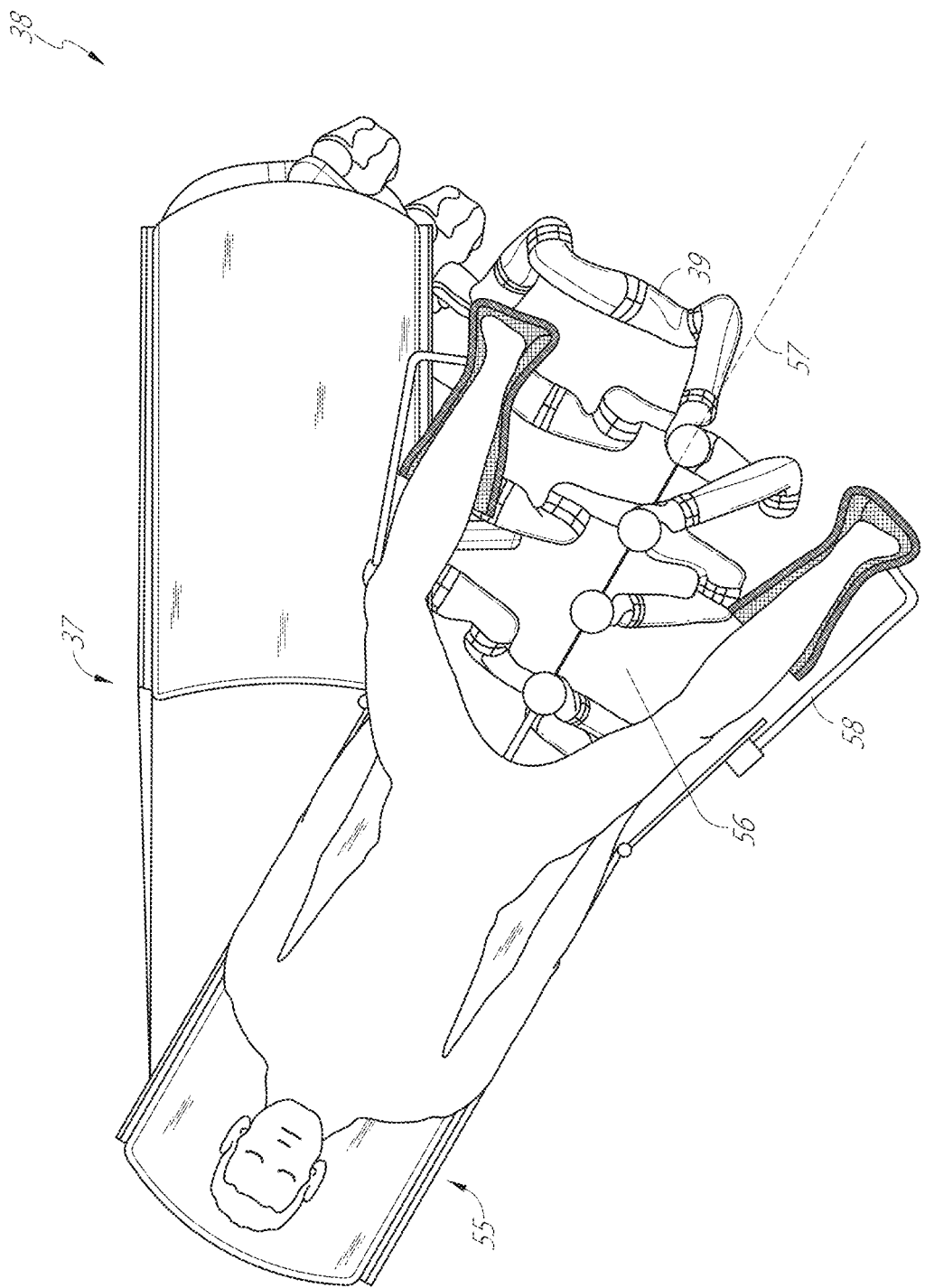
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
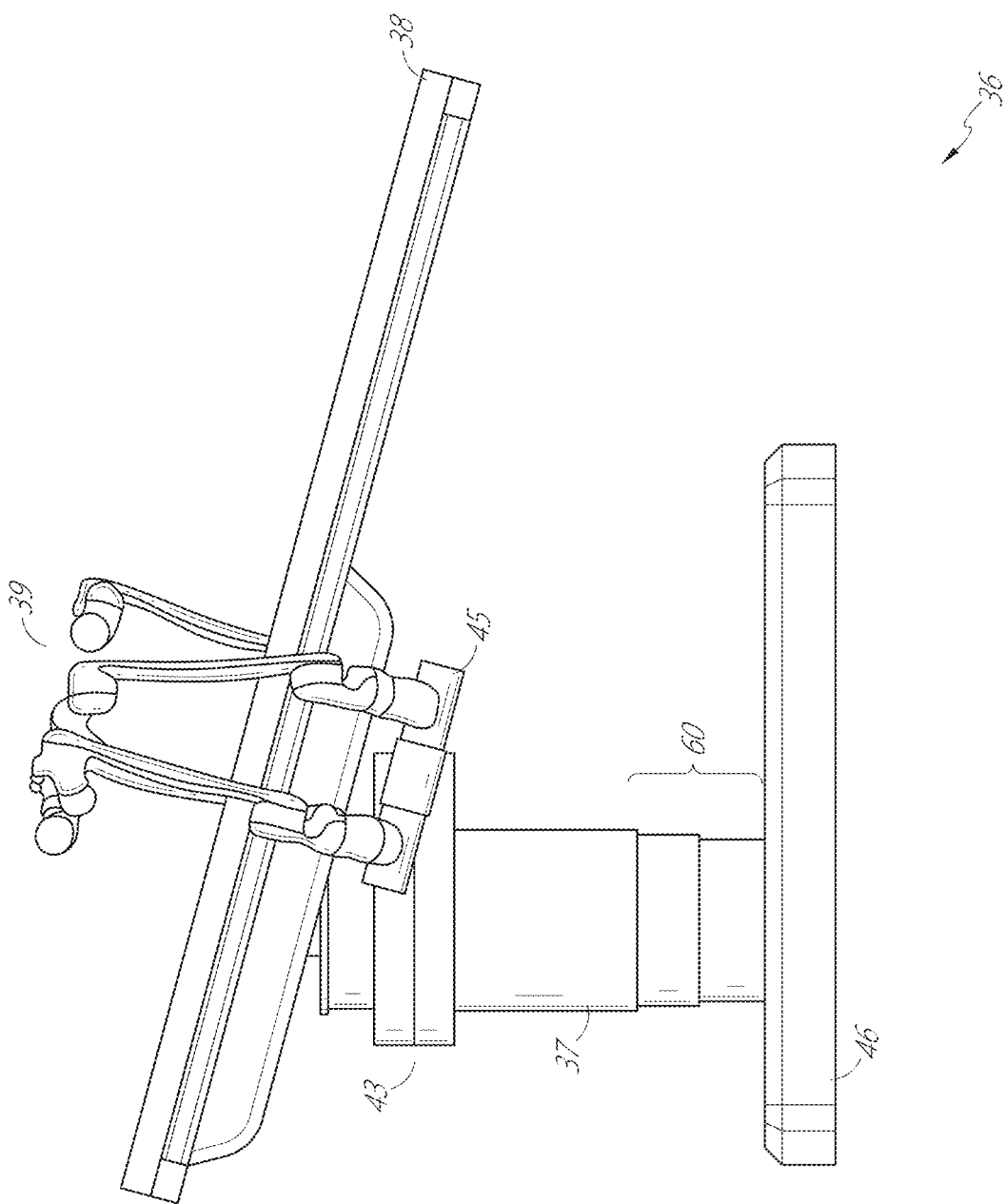
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
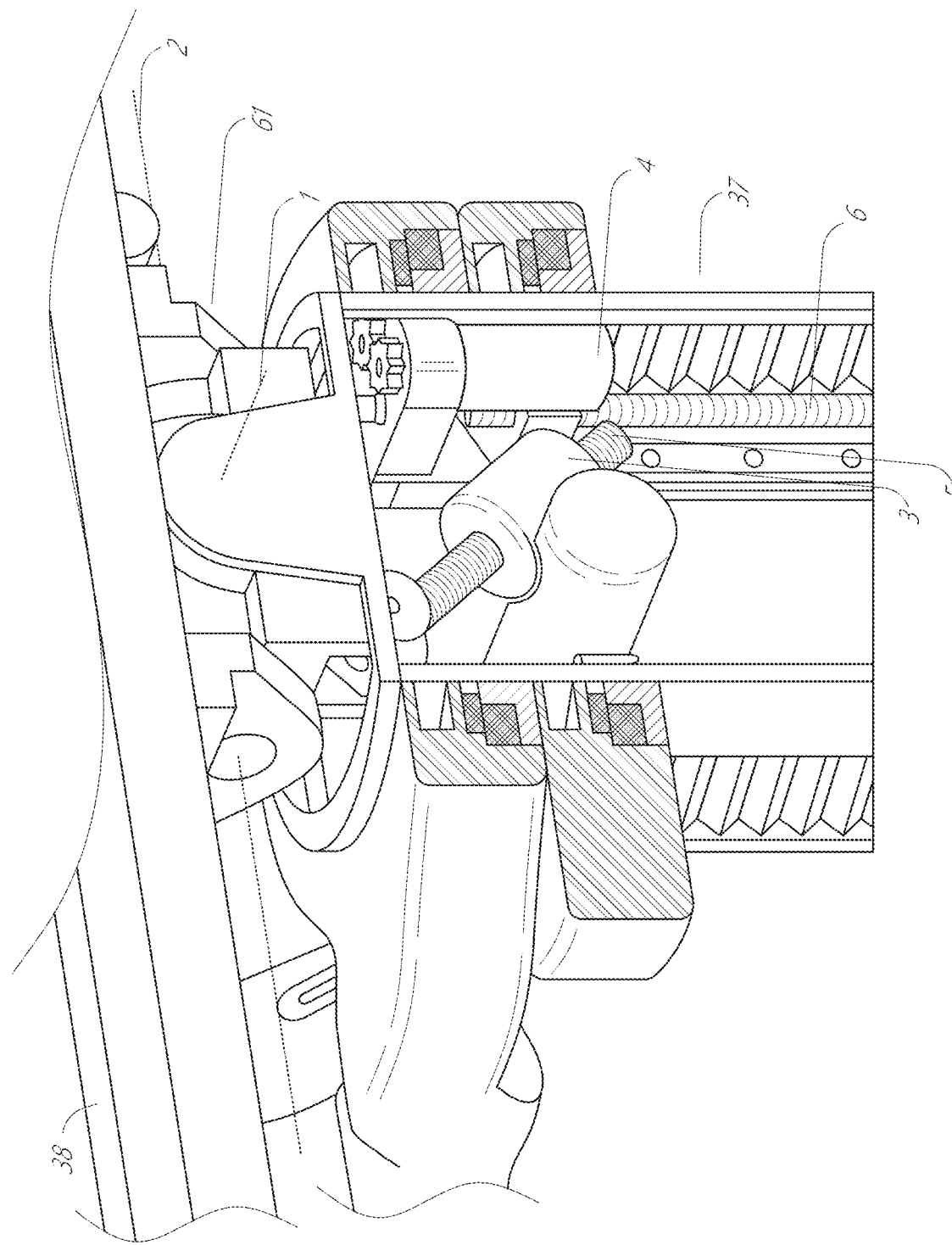
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
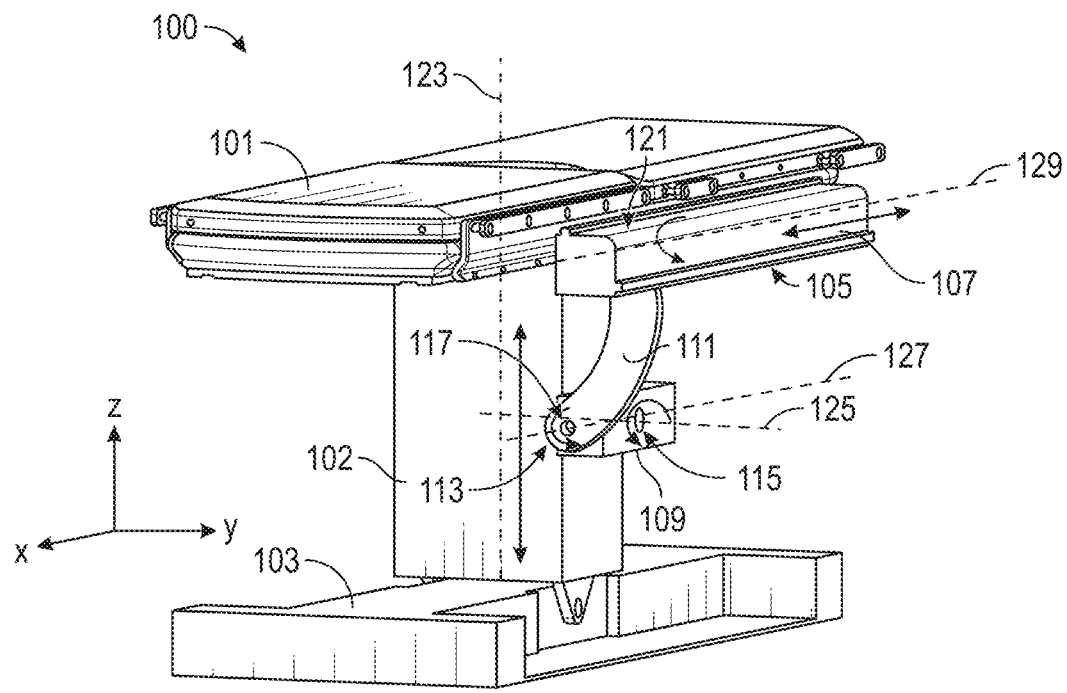
FIG. 12 illustrates an alternative embodiment of a table-based robotic system.
Figure 13:
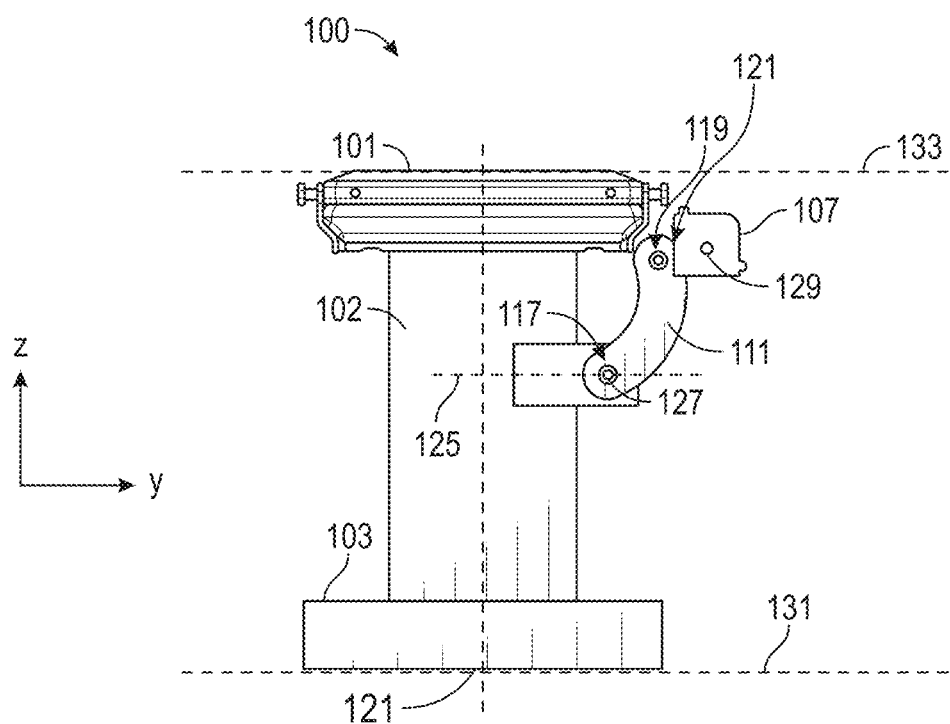
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
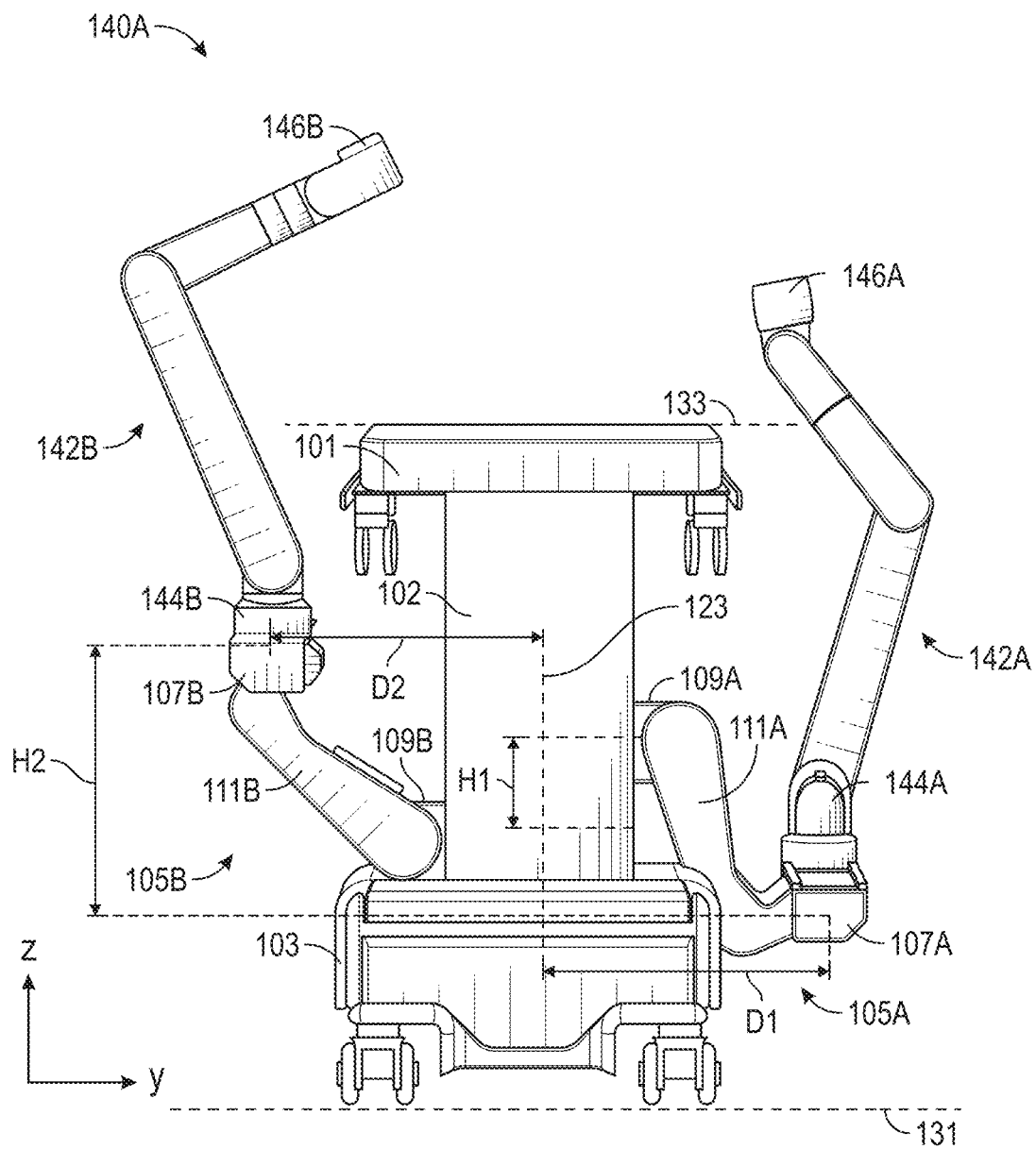
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
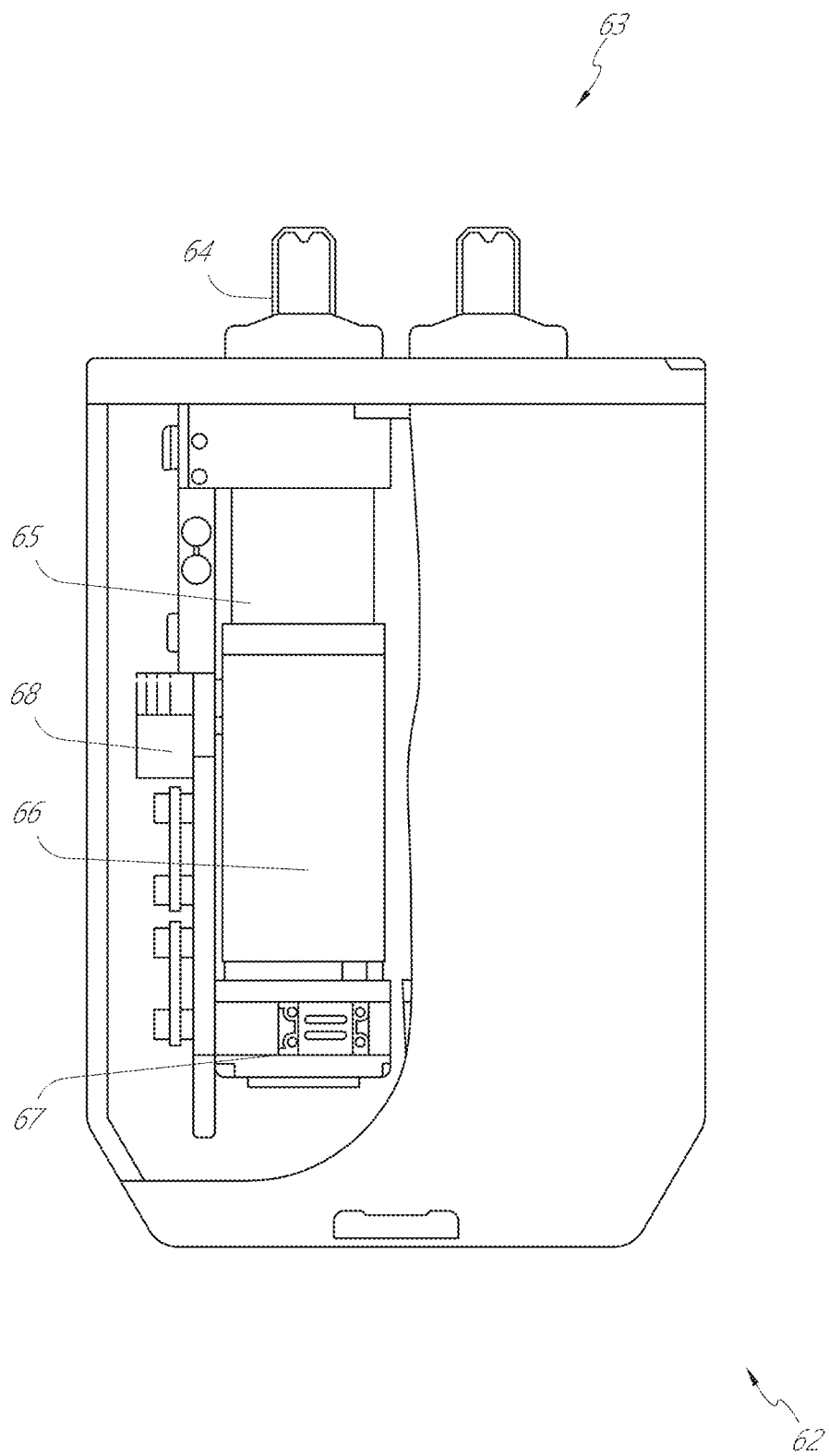
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
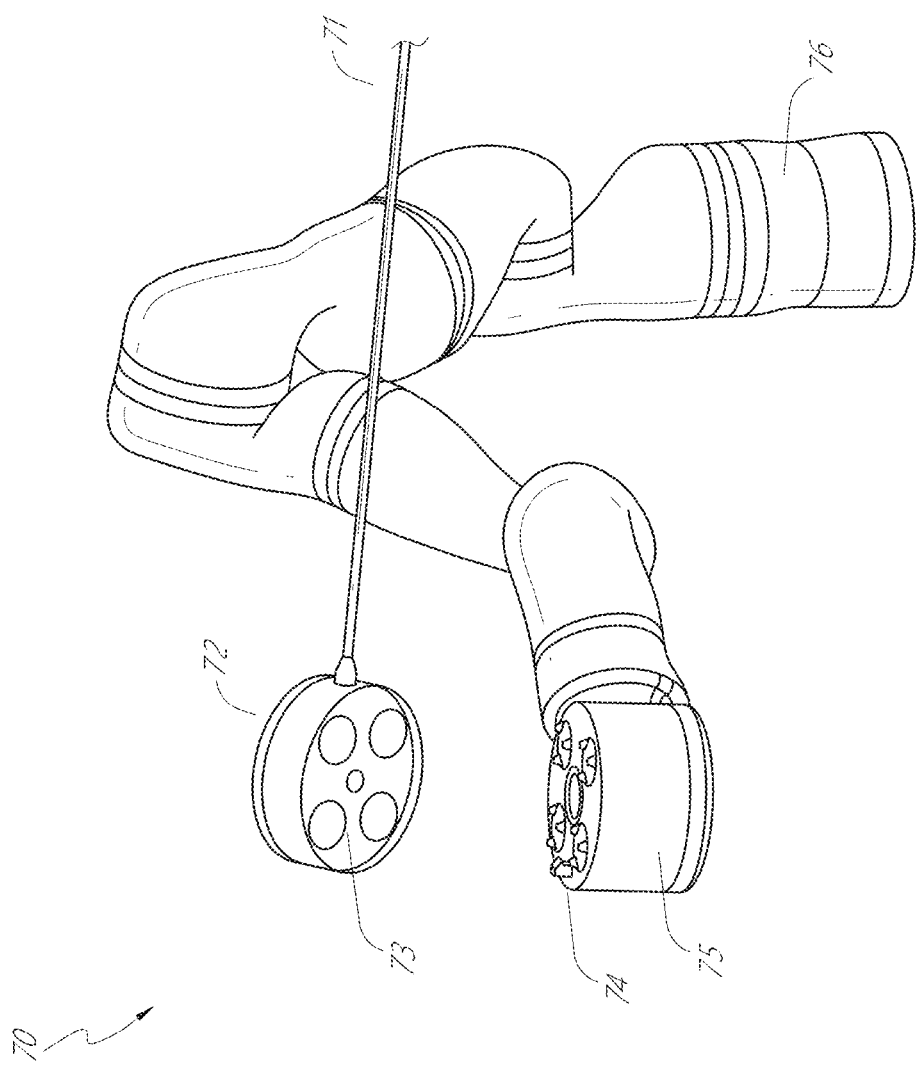
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
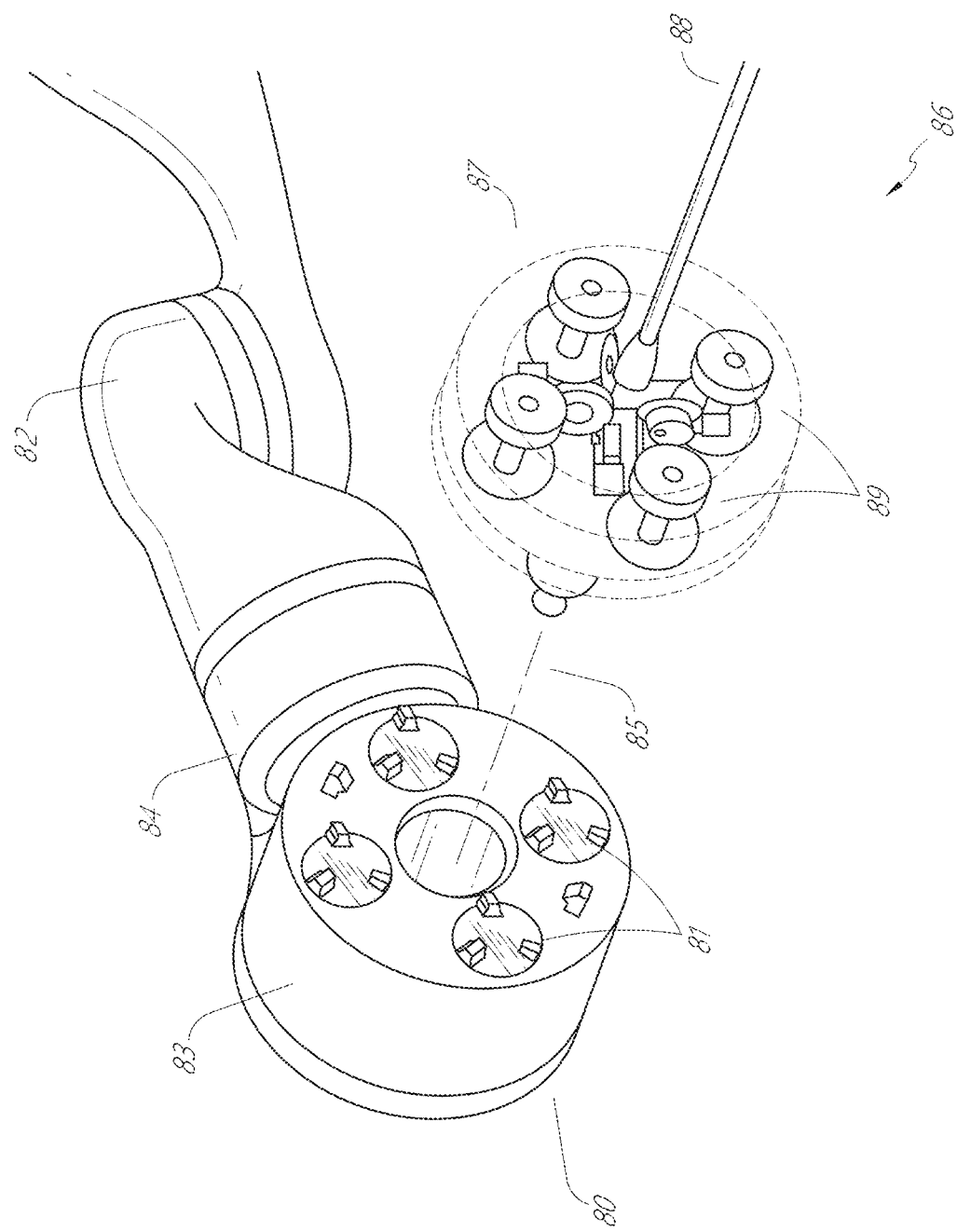
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
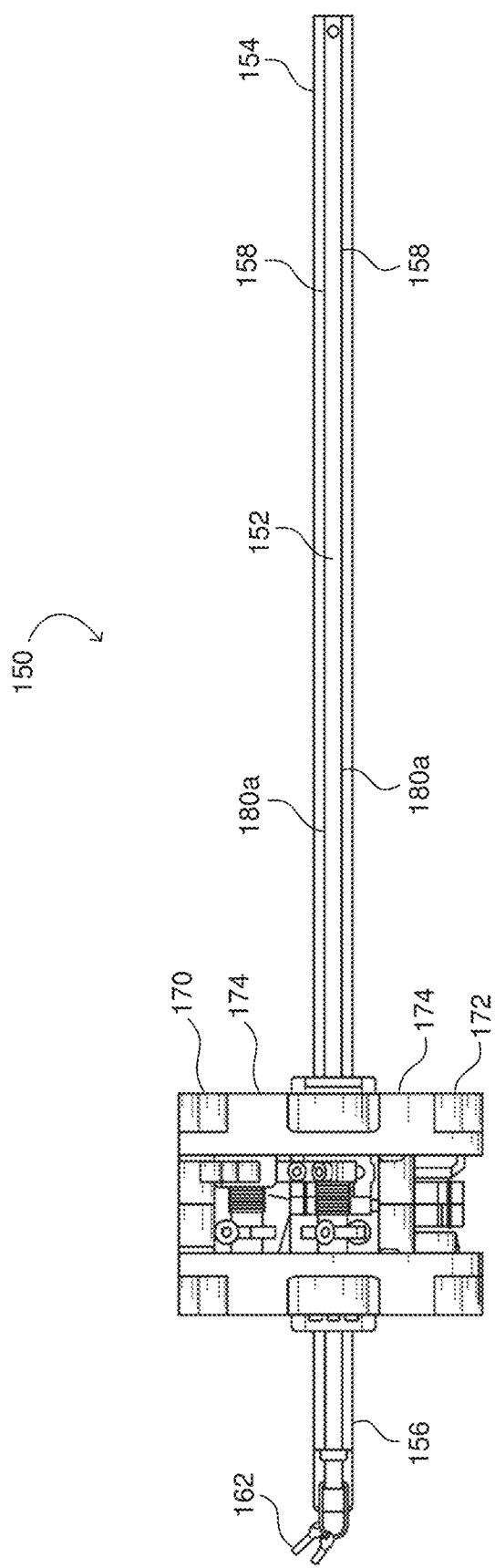
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
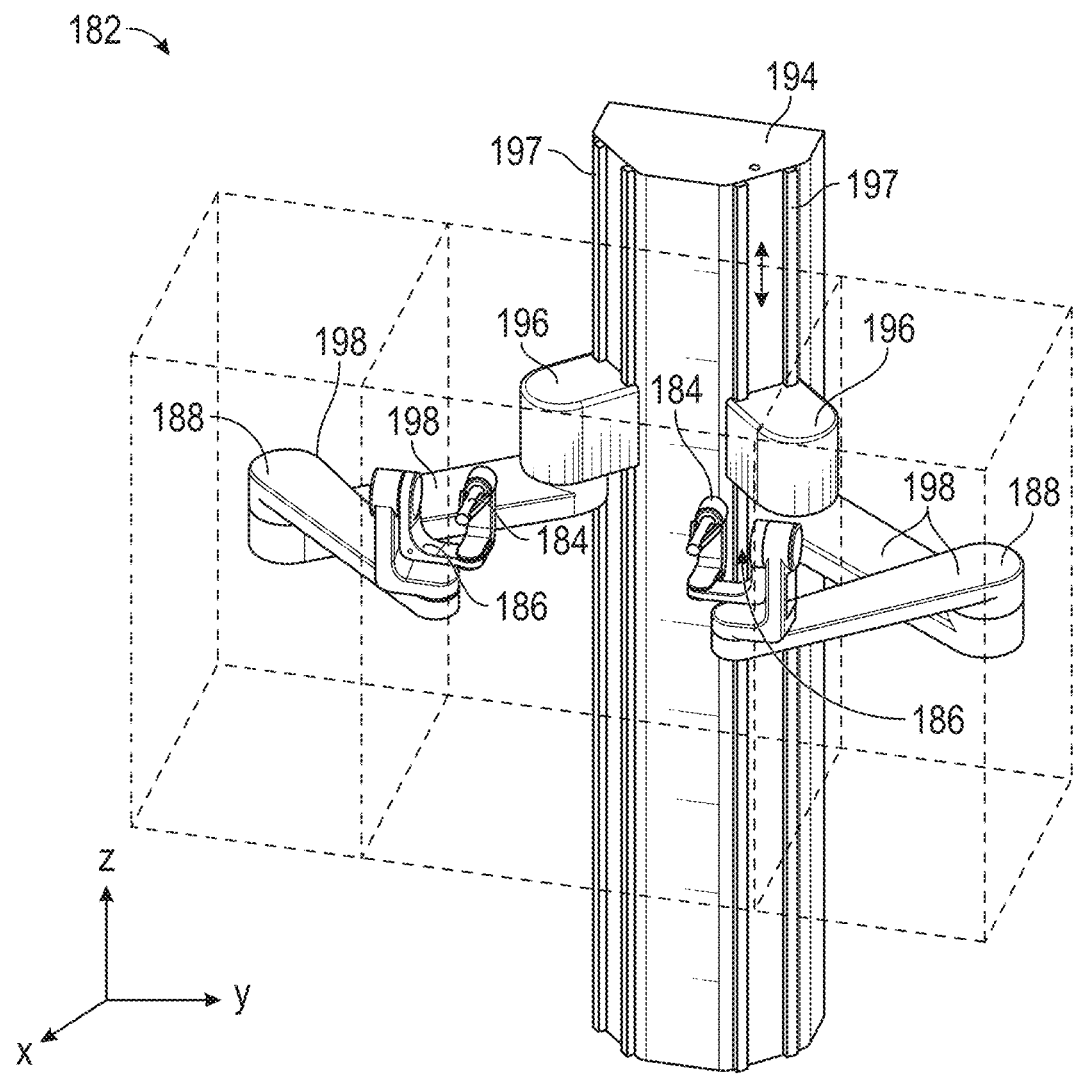
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
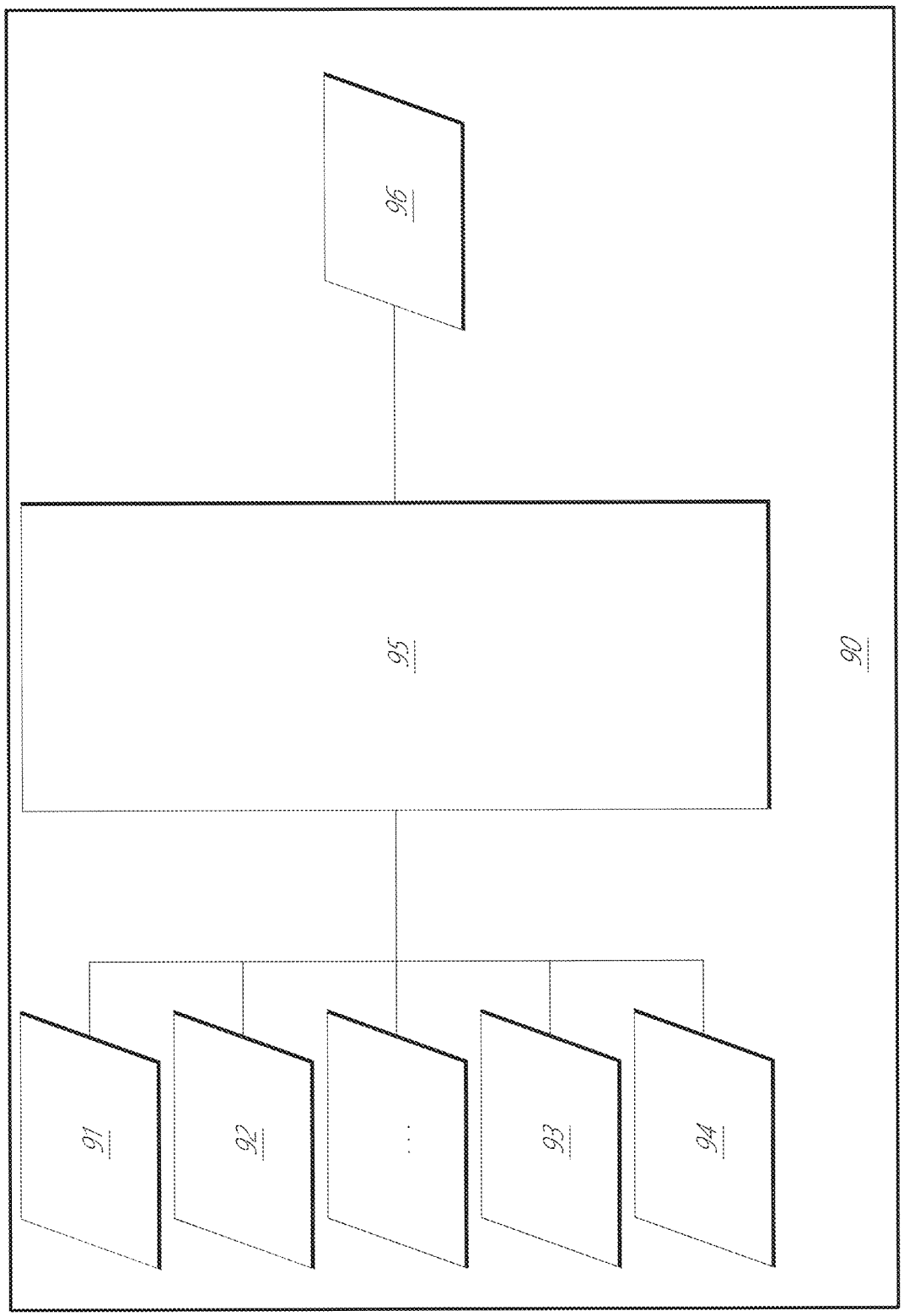
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Manually and Robotically Controllable Medical Instruments.

Embodiments of the disclosure relate to devices, systems, and techniques for manually and robotically controllable medical instruments. The manually and robotically controllable medical instruments can be used, in some embodiments, with robotically-enabled medical systems, such as those described above with reference to FIGS. 1-20. As discussed in detail below, the manually and robotically controllable medical instruments may be configured for manual control, robotic control, or both. Such medical instruments can be also considered hybrid medical instruments because they are configured for both manual and robotic control. Examples of medical instruments can include an endoscope, a camera (e.g., with an optical fiber), a basketing tool, a blade tool, a laser tool (e.g., with an optical fiber), and/or other instruments described herein.

In some embodiments, the medical instruments can be configured for endoscopic procedures. For example, the medical instruments can be configured for uroscopy, ureteroscopy, gastroscopy, bronchoscopy, or other endoscopic procedures. In some embodiments, the medical instruments can be configured for laparoscopic procedures or other types of medical procedures (e.g., open procedures).

A. Introduction to Manually and Robotically Controllable Medical Instruments.

In some embodiments, the manually and robotically controllable medical instruments can be operated in a first mode (a manual mode) by a physician or other operator that physically handles and manually manipulates the medical instrument, and can also be operated in a second mode (a robotic mode) by a robotically-enabled medical system. When operated in the manual mode, the physician can manually manipulate one or more manual drive inputs to control the medical instrument. When operated in the robotic mode, the medical instrument can be attached to an instrument drive mechanism that is positioned on the end of a robotic arm or other instrument positioning device. The instrument drive mechanism can include one or more robotic drive outputs that engage one or more robotic drive inputs to robotically control the medical instrument. The physician may use a controller (for example, as shown in FIG. 19) to control the robotically-enabled system.

The medical instruments can include an elongated shaft and an instrument handle (or instrument base). The elongated shaft can be configured for insertion into a patient's anatomy during a medical procedure. In some embodiments, the elongated shaft is inserted into the patient's anatomy through a natural orifice. In some embodiments, the elongated shaft is inserted into the patient's anatomy through an incision or other surgical opening. The elongated shaft can be flexible. The elongated shaft can be articulable and controllable. This can allow an operator, such as a physician, to control the articulation of the elongated shaft so as to navigate and steer the medical instrument through the patient's anatomy. Controlling the articulation of the elongated shaft can include deflecting or bending an articulable portion of the elongated shaft and in certain embodiments the roll or rotation of the elongated shaft about a longitudinal axis of the shaft. In some embodiments, the articulable portion can be a distal portion of the elongated shaft. The articulable portion may be articulable in one or more degrees of freedom. Degrees of freedom may be linear or rotational or include articulation along a plane. Actuation of the elongated shaft may be controlled at the instrument base.

As described above (for example, with reference to FIGS. 15-18), in some embodiments, the medical instrument can include one or more pull wires extending along (e.g., on or through) the elongated shaft. The pull wires can be attached to actuation mechanisms, such as pulleys and/or capstans, within the instrument handle. The actuation mechanism can, in turn, be connected to the manual and robotic drive inputs such that actuation of the manual and robotic drive inputs operates the actuation mechanisms to pull on the pull wires to cause articulation of the elongated shaft. In some embodiments, one or more of the manual drive inputs and one or more of the robotic drive inputs are each connected to the same actuation mechanism (e.g., pulley, capstan, and/or pulley assembly) within the instrument handle such that both the manual drive input and the robotic drive input can be used to actuate the same actuation mechanism. The manual drive inputs can be separate from the robotic drive inputs.

For example, the manual drive inputs can be configured and positioned so as to be hand operable, while the robotic drive inputs can be configured and positioned so as to engage with robotic drive outputs so as to be operable by a robotically-enabled medical system. In some embodiments, the manual drive inputs remain exposed or accessible even when the instrument handle is attached to the instrument drive mechanism.

The medical instruments configured for both robotic and/or manual control can, in some embodiments, provide one or more advantages. For example, in some embodiments, during a procedure, the medical instruments can first be inserted into the patient manually. A physician may first physically handle and manually insert the medical instrument into the patient using the manual drive inputs to control the articulation of the elongated shaft to guide the medical instrument through the patient's anatomy. A medical instrument that can provide a physician the ability to first perform manual insertion can, in some instances, be quicker and easier than robotic insertion. Manual insertion may provide a practitioner subtle feedback from the patient's internal anatomy, for instance. This can be the case, for example, in certain urological procedures, such as urologic endoscopy, cystoscopy, ureteroscopy, or nephrology, and gastrointestinal endoscopic procedures. After the initial manual insertion, the instrument handle can be attached to the instrument drive mechanism, such as an instrument drive mechanism positioned on the end of a robotic arm or other instrument positioning device or a robotically-enabled medical system. When attached to the robotically-enabled medical system, articulation and control of the elongated shaft of the medical instrument can then be controlled robotically. Robotic control can allow precise and accurate control of the medical instrument at the treatment site. Because certain aspects of medical procedures may be better suited for manual control and other aspects of medical procedures may be best suited for robotic control, the hybrid medical instruments described herein can advantageously be used in either manual or robotic control modes as desired depending on the particular circumstances or stage of the medical procedure. Such medical instruments provide great flexibility to physicians and facilitate performance of the medical procedure.

Additionally, some robotically-enabled medical systems can be limited in absolute insertion depth or stroke. It may be advantageous for a practitioner to manually insert the instrument to set an approximate or coarse location of instrument (e.g., instrument head), while the robotic features may provide more fine-tuning of the instrument location. Thus, it may be advantageous to first insert the medical instrument manually such that the finite insertion depth or stroke of the robotic system can be advantageously utilized in the area of diagnosis or treatment. The medical instruments described herein can allow the placement of the instrument manually over long distances that would be cumbersome to do robotically. In some embodiments, manual control of the instrument may be used to provide an initial gross positioning for the medical instrument. For example, manual control can be used to position the medical instrument at or near the treatment site within the patient's anatomy, and robotic control of the instrument can be used to provide fine position control during the procedure.

In some embodiments the physician may control the medical instrument manually by operating the manual drive inputs before the medical instrument is attached to the instrument drive mechanism. In some embodiments the physician may control the medical instrument manually by operating the manual drive inputs while the medical instrument is attached to the instrument drive mechanism.

As mentioned above, the medical instruments can include both manual and robotic drive inputs. In some embodiments, one of the manual drive inputs is configured to provide two-way deflection control for the elongated shaft of the medical instrument. Two-way deflection control can allow deflection of the elongated shaft in two directions. In some embodiments, the two directions can be opposite directions, such as up and down or left and right. This can also referred to as two-way deflection control in a single plane, such as an up-down plane or a left-right plane. Directional terms (e.g., up, down, left, right, etc.) in this application are used broadly to indicate different directions relative to an orientation of the medical instrument. Because the medical instrument can be constantly repositioned in a wide variety of orientations, the directional terms should not be interpreted as limiting. For example, the directions referred to as up, down, left, and right can change depending on the orientation of the instrument. The manual drive input configured for two-way deflection control can be, for example, a lever, a slider, a wheel, or other type of manually operable drive input. In some embodiments, manipulating the manual drive input in a first direction causes deflection of the elongated shaft in a first direction (e.g., up) and manipulating the manual drive input in a second direction causes deflection of the elongated shaft in a second direction (e.g., down).

The medical instrument can also include a manual drive input configured to allow roll control for the elongated shaft. This may be referred to as a manual roll input. For example, the medical instrument can include a manual drive input that allows the elongated shaft to be rotated about an axis of the elongated shaft relative to the instrument handle. This manual drive input can be configured to allow roll of the elongated shaft (where the shaft is rotated about the longitudinal axis of the shaft) with respect to the instrument handle. In some embodiments, manual roll control can permit rotation of the elongated shaft of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360 degrees, or greater, in both rotational directions. In some embodiments, the manual drive input configured for roll control can be omitted and the physician can physically roll the entire medical instrument (e.g., roll the handle and elongated shaft together) to manually control the roll of the elongated shaft.

Manually controlling the medical instrument using two-way deflection and roll control may be disposed to be intuitive and familiar to many physicians accustomed to working with medical instruments that are only configured for manual control.

In some embodiments, the medical instrument may include an additional drive input configured to allow an additional two-way deflection control. For example, the first manual drive input can allow two-way deflection control in up and down directions, and the second manual drive input can allow two-way deflection control in left and right directions. This would permit four-way deflection control for the elongated shaft using two manual drive inputs.

In some embodiments, the robotic drive inputs are configured to allow four-way deflection control. In some embodiments four-way deflection control allows articulation of the elongated shaft in four different directions. In some embodiments, the directions can be four orthogonal directions, such as up, down, left, and right. In some embodiments, the robotic drive inputs configured for four-way deflection control can include two robotic drive inputs. The two robotic drive inputs can be configured to engage to with two corresponding robotic drive outputs on the instrument drive mechanism. Each robotic drive input can be rotatable in two opposite directions, for example, clockwise and counterclockwise. Rotation of a first of the two robotic drive inputs in one direction (e.g., the clockwise direction) can allow articulation in one of the four direction (e.g., up). Rotation of the first of the two robotic drive inputs in the opposite direction (e.g., the counterclockwise direction) can allow articulation in another of the four directions (e.g., down). Rotation of a second of the two robotic drive inputs in one direction (e.g., the clockwise direction) can allow articulation in another of the four directions (e.g., right). And rotation of the second of the two robotic drive inputs in the opposite direction (e.g., the counterclockwise direction) can allow articulation in another of the four direction (e.g., left). Thus, four-way deflection control can be achieved using two robotic drive inputs. In some embodiments, the robotic drive inputs are configured to provide other numbers of directional deflection control, such as two-way deflection control, three-way deflection control, etc.

The medical instrument can include an additional robotic drive input configured to provide robotic roll control for the elongated shaft of the medical instrument. For example, the medical instrument can include a robotic drive input configured to engage with a corresponding robotic drive output on the instrument drive mechanism that allows the elongated shaft to be rotated about an axis of the elongated shaft relative to the instrument handle. This robotic drive input can be configured to allow reorientation of the elongated shaft radially with respect to the instrument handle. In some embodiments, rotation of this robotic instrument drive input in a first direction (e.g., clockwise) causes rotation of the elongated shaft in the clockwise direction and rotation of this robotic instrument drive input in a second direction (e.g., counterclockwise) causes rotation of the elongated shaft in the counterclockwise direction. In some embodiments, robotic roll control can permit rotation of the elongated shaft of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360 degrees, or greater, in both rotational directions.

In some instances, robotically controlling the medical instrument using four-way deflection control and roll control may be intuitive and familiar to many physicians accustomed to working with robotic instruments that are only configured for robotic control. For example, four way deflection control may be intuitive when operating a controller to control the medical instrument.

As mentioned above, in some embodiments, the medical instruments are configured for manual control that permits manual two-way deflection control and roll control (roll control can be manually achieved either with a manual drive input configured for rolling the elongated shaft relative to the instrument handle or by physically rolling the entire medical instrument) and robotic control that permits robotic four-way deflection control and roll control. Other types of manual and robotic control are also possible. For example, the medical instruments can be configured for manual control that permits manual four-way deflection control and roll control and robotic control that permits robotic four-way deflection control and roll control. As another example, the medical instruments can be configured for manual control that permits manual two-way deflection control and roll control and robotic control that permits robotic two-way deflection control and roll control.

In some configurations, a plurality (e.g., two, three, four, etc.) can be coupled together (e.g., removably coupled) for easier use by a doctor. For example, an endoscope can be coupled to another instrument. The other instrument can be any instrument described herein (e.g., a laser tool, a basketing tool, forceps, a blade, etc.). The other instrument may include an elongate shaft that couples to the endoscope via an inlet of the endoscope. In some configurations, the inlet can allow the elongate shaft of the other instrument to enter into a working channel of the endoscope. Thus, it can be possible to incorporate a shaft of the other instrument into the working channel of the endoscope. In this way, the endoscope and the other instrument can be coupled together in their working channel. In some embodiments, a base of the endoscope and a base of the other instrument can also be coupled together. This coupling of the bases can be achieved through a coupling mechanism (e.g., a clip, a snap, a magnet, a button, etc.).

In some embodiments, the plurality of instruments can be coupled together for use of full manual operation, full robotic operation, or a hybrid of manual and robotic operation. For example, a plurality of instruments may be coupled together (e.g., at their bases and/or via an inlet, etc.) to be held as a unit in the hand of a practitioner. In some embodiments, the unit may be configured to be coupled to the robotic instrument drive system as a unit. One or both of the instruments may later, for example, be decoupled from the robotic instrument drive system and/or from another instrument of the plurality of instruments. Thus, in some embodiments, great flexibility can be achieved in which instruments are used manually (if any), which are used robotically (if any), and which are used as a hybrid (if any). The one or more medical instruments may be controlled remotely. For example, robotic functionality described herein may be handled remote from the robotic instrument drive system.

B. Example Embodiments of Manually and Robotically Controllable Medical Instruments.

The above-noted and other features of the manually and robotically controllable medical instruments will now be described with reference to the embodiments illustrated in FIGS. 21A-31. These embodiments are provided byway of example and are intended to be illustrative of the principles of the disclosure without limiting the disclosure. Those of ordinary skill in the art will, upon consideration of this disclosure, appreciate that various modifications of the illustrated embodiments are possible. These modification are intended to be within the scope of this disclosure.

Figure 21A:
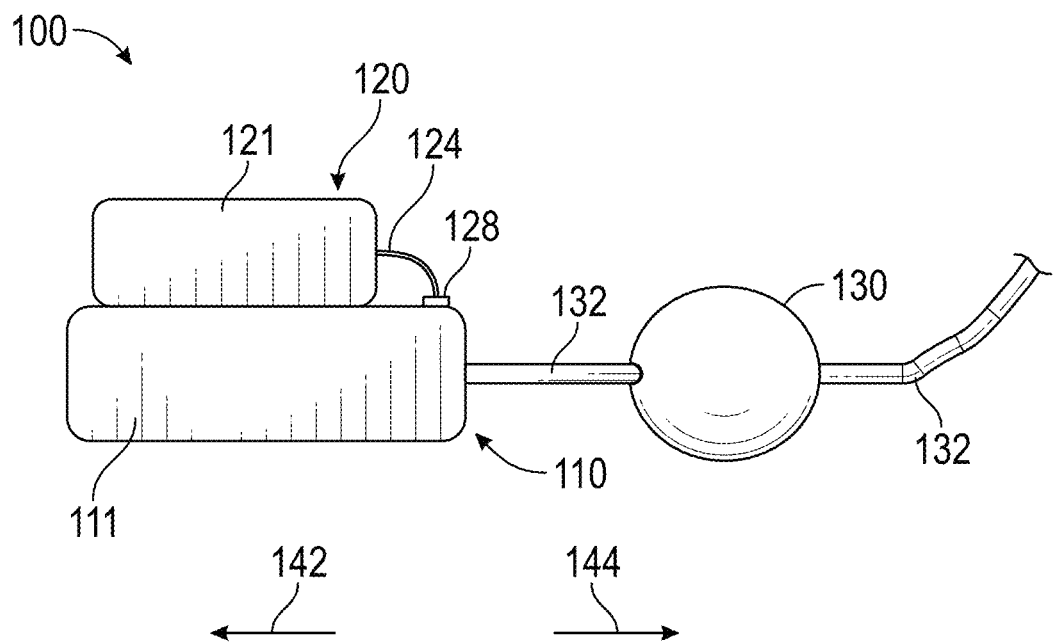

FIG. 21A illustrates a schematic of an example medical instrument system 100. A proximal direction 142 and a distal direction 144 are shown for reference. The medical instrument system 100 can include an endoscope 110, an instrument 120, and/or distal drive unit 130. As shown, the instrument 120 can include an instrument base 121 and an instrument shaft 124. The endoscope 110 can include an endoscope base 111 and an endoscope shaft 132. The instrument shaft 124 can be coupled to the instrument base 121 at a distal end of the instrument base 121. The instrument shaft 124 can be inserted into a working channel (not shown) of the endoscope shaft 132 through an instrument inlet 128. Accordingly, the instrument 120 is sometimes referred to herein as a working channel instrument, although features described herein with respect to the working channel instrument may be applied to other types of manual, robotic, and/or flexible instruments in other embodiments. The instrument inlet 128 can support the instrument shaft 124 to, for example, prevent inadvertent translation and/or rotation of the instrument shaft 124 at the point of insertion into the instrument inlet 128. The endoscope base 111 can be coupled to the instrument base 121, such as via a coupling mechanism.

The distal drive unit 130 can be used to control the movement of the endoscope shaft 132. For example, the distal drive unit 130 can translate the endoscope shaft 132 proximally and/or distally. The distal drive unit 130 can be robotically and/or remotely controlled. The distal drive unit 130 can include, for example, feed rollers, rack and pinion mechanisms, pinchers, grippers, or other mechanisms that are configured drive insertion or retraction of the endoscope shaft 130. Alternatively, the distal drive unit 130 can be replaced with a robotically controlled or steered sheath, or the distal drive unit 130 may be omitted.

Figure 21B:
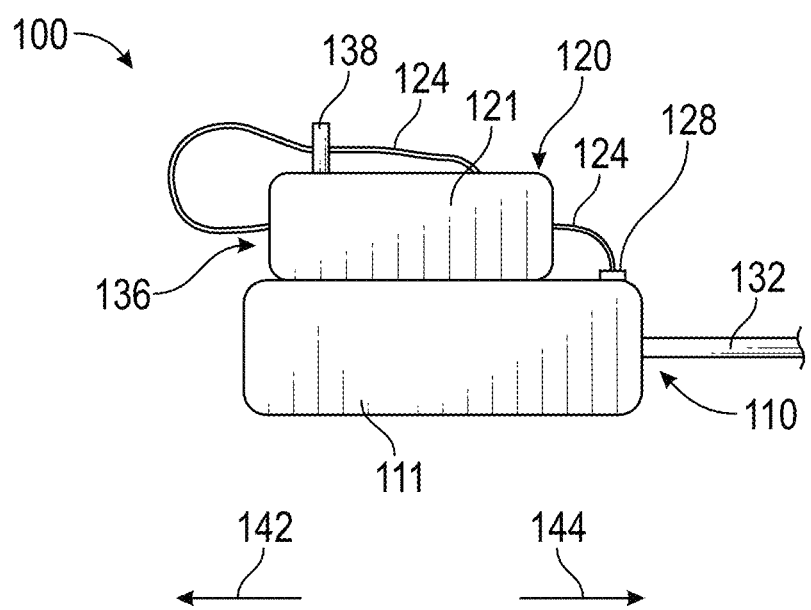

FIG. 21B illustrates a schematic of an medical instrument system 100 that can have features similar to the embodiment described above with reference to FIG. 21A where the instrument shaft 124 extends proximally from a proximal portion 136 of the instrument base 121. In some configurations it may be advantageous to form a partial loop in the instrument shaft 124 by having it extend proximally (instead of distally) from the instrument base 121. For example, this configuration can allow for easier manual manipulation of the instrument shaft 124. In some configurations, an instrument actuator 138 can be included to manually and/or robotically translate the instrument shaft 124 longitudinally (e.g., proximally, distally). The instrument actuator 138 can be a linear actuator. The instrument actuator 138 can be rigidly coupled to the instrument shaft 124 to prevent sliding and/or rotation of the instrument shaft 124 where the instrument shaft 124 is coupled to the instrument actuator 138. Thus, the instrument actuator 138 can control a longitudinal position of the instrument shaft 124 and therefore a distal portion of the instrument actuator 138 (e.g., a portion inserted in a patient). As shown, the instrument shaft 124 re-enters the instrument base 121 before entering endoscope shaft 132 through the inlet 128. However, in some configurations, the instrument shaft 124 may be directly (e.g., without re-entering the instrument base 121) coupled to the instrument inlet 128.

The partial loop formed by the instrument shaft 124 can form a curvature having a radius. The radius can be modified in response to a translation of the instrument actuator 138. The radius can be about 1 mm, about 2 mm, about 3 mm, about 5 mm, about 8 mm, about 10 mm, about 12 mm, about 15, mm about 20 mm, about 25 mm, about 30 mm, about 35 mm, about 40 mm, about 45 mm, about 50 mm, about 60 mm, about 70 mm, about 80 mm, about 90 mm, 100 mm, any distance there between, or fall within any range having endpoints therein.

FIGS. 21C-21E show embodiments of example medical instrument systems 100 that include vertical and/or horizontal orientations with a robotic instrument drive mechanism 150. As shown in FIG. 21C, the endoscope 110 can be disposed between the instrument 120 and the robotic instrument drive mechanism 150. As shown in FIG. 21D, in some embodiments the instrument 120 can be disposed between the endoscope 110 and the robotic instrument drive mechanism 150. A robotic arm can be coupled to the robotic instrument drive mechanism 150. Although some embodiments described herein include a robotic instrument drive mechanism 150 that is directly coupled to both the instrument 120 and the endoscope 110 in a side by side configuration, as shown in FIG. 21E for example, the robotic instrument drive mechanism 150 shown in FIGS. 21C-21D is directly coupled to either the endoscope 110 or the instrument 120 in a stacked configuration. In these examples, direct coupling includes coupling via a sterile adapter, in which case the robotic drive outputs 154 are the drive outputs of a sterile adapter that can be mounted to the robotic capital equipment. The robotic instrument drive mechanism 150 can include one or more robotic drive outputs 154 that can couple to corresponding robotic drive inputs (not shown) of the endoscope base 111 and/or the instrument base 121. In some embodiments, such as shown in FIG. 21C, the endoscope 110 can include robotic drive inputs (e.g., coupling to the drive outputs 154) that serve also as robotic drive outputs themselves that couple to corresponding robotic drive inputs of the instrument 120. Additionally or alternatively, the instrument 120 can include robotic drive inputs (e.g., coupling to the drive outputs 154) that serve as robotic drive outputs that couple to corresponding robotic drive inputs of the endoscope 110, such as in embodiments shown in FIG. 21D. Thus, in some embodiments, a drive input for one medical instrument (e.g., the endoscope 110) can also comprise a drive output for a different medical instrument (e.g., the instrument 120). In this way, the instrument 120 may be controlled indirectly by the robotic instrument drive mechanism 150 even if the instrument base 121 is not directly coupled to the robotic instrument drive mechanism 150.

In some configurations, the robotic instrument drive mechanism 150 can be directly coupled to the instrument 120 via, for example, robotic drive inputs that couple directly to corresponding robotic drive outputs (e.g., through the endoscope 110). For example, the robotic drive inputs of the instrument 120 may be elongate drive inputs (e.g., that extend through at least partially through the endoscope 110) that couple with corresponding robotic drive outputs of the robotic instrument drive mechanism 150. Additionally or alternatively, the robotic instrument drive mechanism 150 can include extended (e.g., elongate) robotic drive outputs that extend at least partially through the endoscope 110 to couple with robotic drive inputs of the instrument 120. Thus, various embodiments allow for direct coupling of robotic drive inputs/outputs between the robotic instrument drive mechanism 150 and the instrument 120 even in the vertical configurations shown in FIGS. 21C-D. Other variants are possible.

Figure 22A:
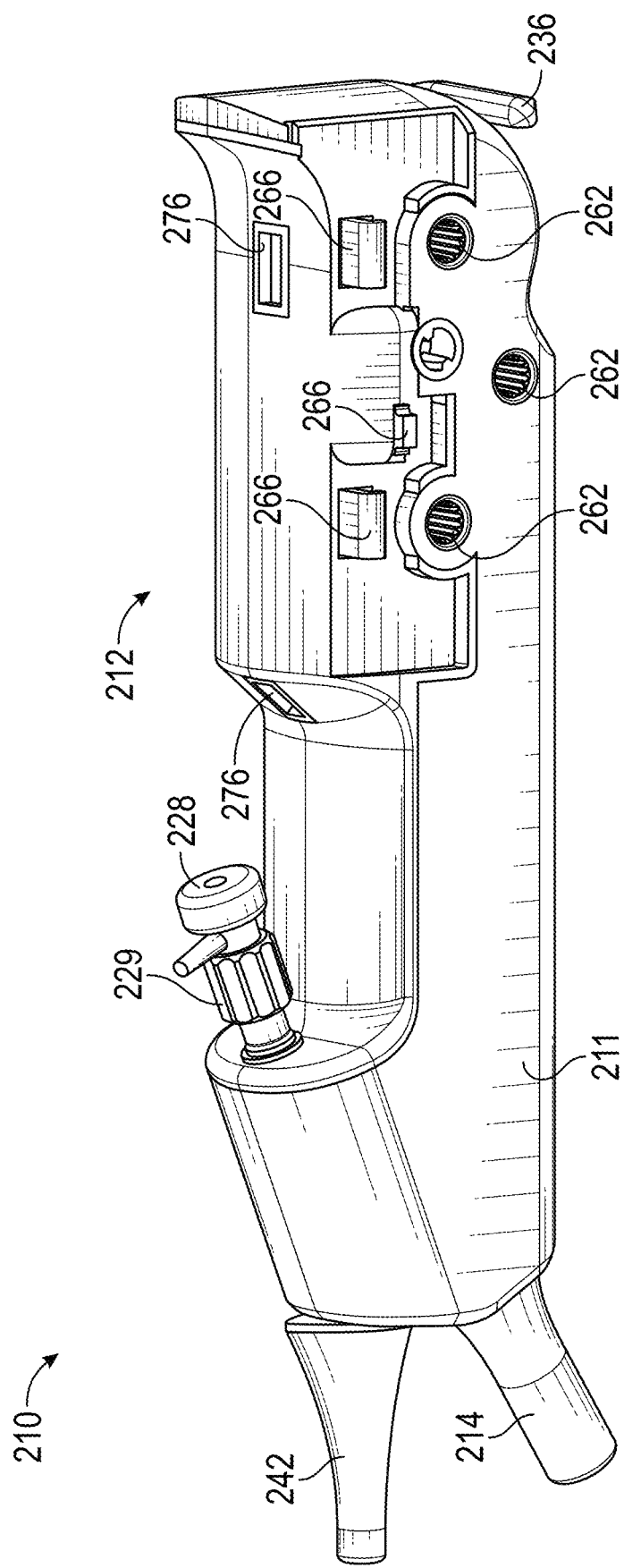
FIG. 22A illustrates a bottom view of an example endoscope according to one configuration.

FIG. 22A illustrates a bottom view of an example endoscope 210 according to one configuration, which can be coupled to and used with an instrument system 100 similar to the embodiments described above with reference to FIGS. 21A and 21B. As illustrated, the endoscope 210 includes an endoscope base 211 (or endoscope handle) and an elongated shaft (not shown). The elongate shaft may extend distally from an endoscope outlet 242. The elongate shaft is configured to be inserted into a patient during a medical procedure. The elongate shaft can be configured to be articulable and controllable, such that the elongate shaft can be navigated and steered through the patient's anatomy. For example, in some embodiments, the elongate shaft comprises a thin, flexible body configured to be inserted into and guided through patient lumens, such as the urethra, ureter, gastrointestinal tract, esophagus, airways of the lungs, etc. As described above, pull wires can be included in or on the elongate shaft to control articulation of the elongate shaft. The elongate shaft can extend between a distal end and a proximal end. The distal end can be configured to be inserted into the patient. The proximal end can be attached to the endoscope base 211 via the endoscope outlet 242. The elongate shaft can include a working channel (not illustrated) through which additional instruments or tools can pass for delivery to the distal end 205. The endoscope 210 can include a working channel entry port (not illustrated) configured to allow access to the working channel. An instrument shaft inlet 228 can allow coupling of an instrument shaft (described below) to be inserted therein and to be coupled into the working channel entry port and into the working channel.

The endoscope base 211 is configured to allow both manual control and robotic control of the endoscope 210. For example, the endoscope base 211 is configured to be physically held and manually manipulated to provide manual control, and to couple to an instrument drive mechanism (see below) to provide robotic control. In some embodiments, a sterile adapter can be positioned between the endoscope base 211 and the instrument drive mechanism to maintain a sterile field during a medical procedure.

As illustrated, the endoscope base 211 includes a housing 212. As illustrated, the housing 212 can also be shaped to include an instrument coupled thereto. The endoscope base 211 includes one or more endoscope receiving elements 276. The endoscope receiving elements 276 are configured to couple with corresponding elements of another instrument (e.g., the instrument 220 described below). The housing 212 of the endoscope base 211 can be shaped to provide an ergonomic fit for the instrument handle in a practitioner's hand and/or for coupling of another instrument. For example, the housing 212 shape can allow the endoscope base 211 to be more easily or comfortably held during manual control. Alternatively or additionally, the housing 212 shape can provide (or not block) access to one or more unused robotic drive outputs on the instrument drive mechanism as will be described below. The endoscope base 211 can include a power access 214 for connecting to a power unit to power the one or more instruments of a medical instrument system 200. The power access 214 can be configured to provide electrical and/or visual connections to the endoscope 210. In the illustrated embodiment, the power access 214 is illustrated as a strain relief for an umbilical cable that leads to a connector at a tower.

The endoscope base 211 can include an instrument shaft inlet 228 that allows insertion of an instrument (e.g., the instrument 220 described below) therein. The instrument shaft inlet 256 may include an instrument inlet actuator 229. The instrument inlet actuator 229 can allow manual control of the shaft of the instrument. In some embodiments, the instrument inlet actuator 229 can be tightened to improve a connection between the instrument shaft and the endoscope 210. The instrument inlet actuator 229 can include a Luer lock assembly. In some embodiments, the instrument inlet actuator 229 can prevent inadvertent slipping (e.g., translation, rotation) of the instrument shaft within the instrument shaft inlet 228. Additionally or alternatively, the instrument inlet actuator 229 can be configured to allow a practitioner to manually rotate the instrument shaft.

The endoscope base 211 can include a manual actuator 236. In the illustrated embodiment, the manual actuator 236 is configured as a lever, although other mechanical structures such as sliders or wheels are possible. As will be described in greater detail below, the manual actuator 236 is configured to provide manual two-way deflection control for the endoscope 210. In the illustrated embodiment, the manual actuator 236 is configured to be manipulated or rotated back and forth. Moving the manual actuator 236 in a first direction can cause articulation of the elongate shaft in a first articulation direction, and moving the manual actuator 236 in a second direction (opposite the first direction) can cause articulation of the elongate shaft in a second articulation direction. The first and second articulation directions can be substantially opposite (e.g., up and down), although this need not be the case in all embodiments.

The endoscope base 211 can also include a manual roll input controllable by the endoscope outlet 242. Though not shown, the proximal end of the elongate shaft of the endoscope 210 can be attached to the endoscope outlet 242. In some embodiments, the elongate shaft extends through the endoscope outlet 242 and into the housing 212 of the endoscope 210. The endoscope outlet 242 can be configured to allow the elongated shaft to rotate relative to the endoscope base 211. As illustrated, the endoscope outlet 242 can be a twister or rotatable handle or grip that can rotate relative to the housing 212. For example, the endoscope outlet 242 can rotate in a clockwise and/or counterclockwise motion. In some embodiments, the endoscope outlet 242 rotates in both the clockwise and counterclockwise directions. The elongate shaft can be rotationally fixed relative to the endoscope outlet 242 such that rotation of the endoscope outlet 242 causes rotation of the elongate shaft. Rotation of the elongate shaft can be in the same direction and equal to corresponding motion of the endoscope outlet 242, although this need not be the case in all embodiments. The elongated shaft may be permitted to rotate (e.g., roll) in both rotational directions of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, or at least 360 degrees. This roll control is optional and, in certain embodiments, the roll can be controlled manually by, for example, rotating the endoscope 210.

With continued reference to FIG. 22A, the endoscope 210 includes a plurality of robotic endoscope drive inputs 262. In the illustrated embodiment, the endoscope 210 includes three robotic endoscope drive inputs 262, although other numbers of robotic endoscope drive inputs 262 can be used in other embodiments. The robotic endoscope drive inputs 262 are configured to engage corresponding robotic drive outputs on an instrument drive mechanism when the endoscope base 211 is attached to the instrument drive mechanism. Example robotic drive outputs and instrument drive mechanisms are shown in FIGS. 15-17 (described above) and FIGS. 25 and 30 (described below). The robotic drive outputs of the instrument drive mechanism engage and transfer torque to or rotate the robotic endoscope drive inputs 262. In some embodiments, each of the robotic endoscope drive inputs 262 are rotatable in both the clockwise and counterclockwise directions. In the illustrated embodiment, the robotic endoscope drive inputs 262 are configured as grooved or keyed recesses and are configured to engage robotic drive outputs that are configured as protruding splines. The robotic drive outputs can be driven by motors to rotate in clockwise and counterclockwise directions. When the robotic drive outputs are engaged with the robotic endoscope drive inputs 262, the robotic drive inputs transfer rotational motion to the robotic endoscope drive inputs 262. In some embodiments, the robotic drive outputs drive the robotic endoscope drive inputs 262. In some embodiments, this arrangement can be reversed or other types and configurations of robotic drive inputs and outputs can be used.

The illustrated embodiment of the endoscope 210 is configured at least for robotic four-way deflection control and robotic roll control. In this embodiment, two of the robotic drive inputs 262 are configured for deflection control, and the other of the robotic drive inputs 262 is configured for roll control. Each of the two of the robotic drive inputs 262 configured for deflection control can permit two-way deflection control so that, together, four-way deflection control can be achieved.

As will be described in more detail below, in some embodiments, actuation of a first robotic drive input of one of the robotic endoscope drive inputs 262 can be configured to cause the same articulation of the elongate shaft as actuation of the manual drive input. For example, both the first robotic drive input and the manual actuator 236 can be configured to cause articulation of the elongate shaft in up and down directions. This can be because, as will be described below, both the first robotic drive input and the manual actuator 236 can be connected to the same articulation mechanism (e.g., a corresponding pulley) within the housing 212 of the endoscope base 211. In some embodiments, the two-way deflection control provided by the manual actuator 236 is the same as the two-way deflection control provided by the first robotic drive input.

Figure 22B:
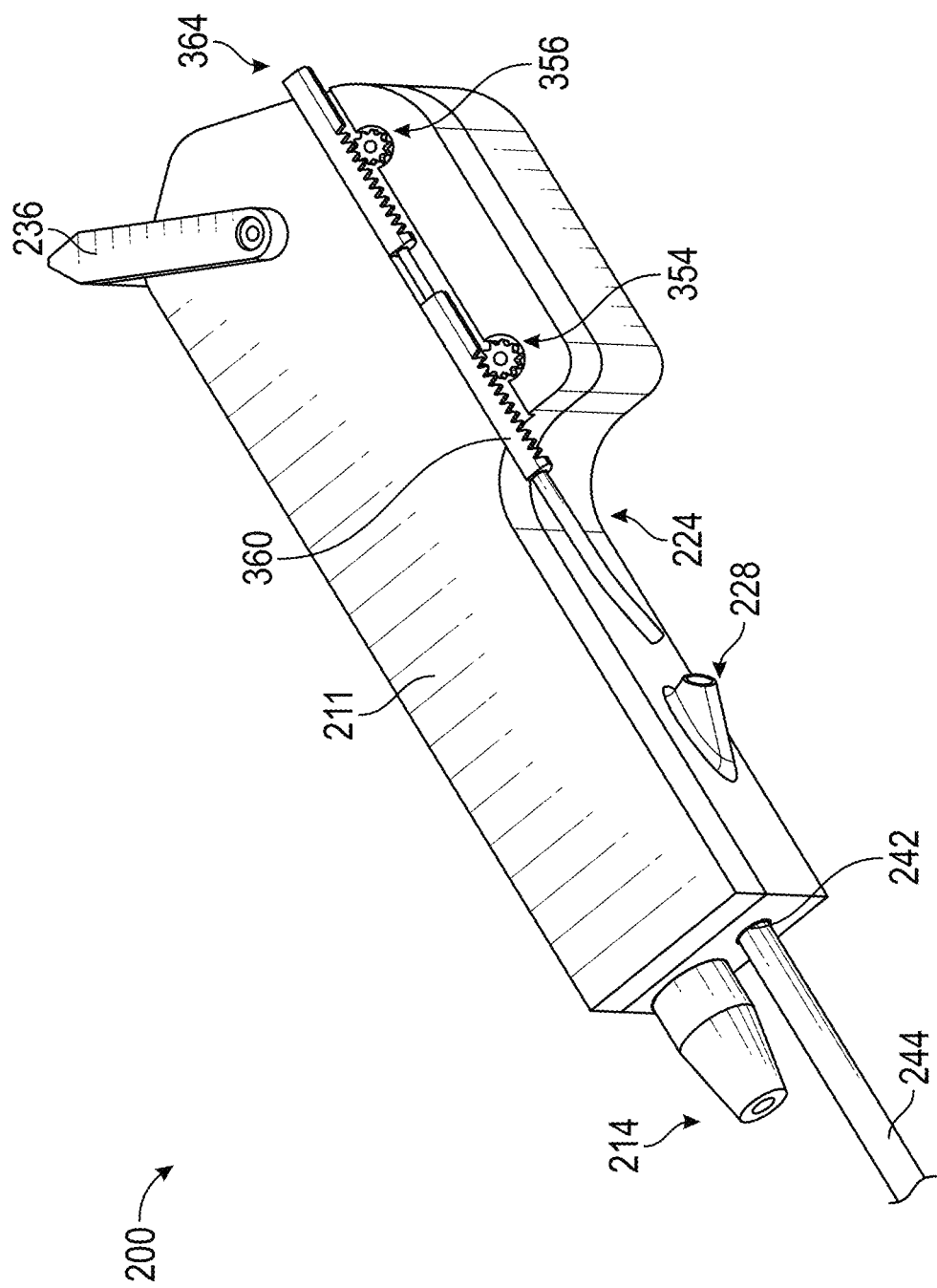
FIG. 22B illustrates a perspective view of an example medical instrument system that includes functionality of another medical instrument therein, according to one configuration.

FIG. 22B illustrates a perspective view of an example medical instrument system 200 that includes functionality of an endoscope and another medical instrument (e.g., a basketing tool) therein, according to one configuration. The medical instrument system 200 can include an endoscope base 211, an endoscope outlet 242, an endoscope shaft 244, a manual actuator 236, a first instrument drive member 354, and a second instrument drive member 356. The first and second instrument drive members 354, 356 may include rotating elements, such as circular gears. In some embodiments, the first and second instrument drive members 354, 356 are coupled to corresponding first and second first linear instrument actuators 360, 364. The first and second instrument drive members 354, 356 and first and second linear instrument actuators 360, 364 share functionality of corresponding elements described below with reference to FIG. 29. The endoscope base 211 may include rotating elements (not shown) for articulating the endoscope shaft 244 in a plurality of degrees of freedom. The rotating elements may share functionality of the pulleys 310 described below with reference to FIG. 23. The first and second first linear instrument actuators 360, 364 may be manually disengaged from the corresponding first and second instrument drive members 354, 356 in some embodiments. This can allow a practitioner to more easily couple the first and second first linear instrument actuators 360, 364 to the endoscope base 211 when needed and/or to decouple the first and second first linear instrument actuators 360, 364 therefrom for quick and easy manual manipulation. Thus, FIG. 22B shows some embodiments where functionality of both an endoscope and another medical instrument are combined into a single endoscope base 211. The manual actuator 236 may share functionality with the manual actuator 236 described in FIG. 23 below.

Figure 23:
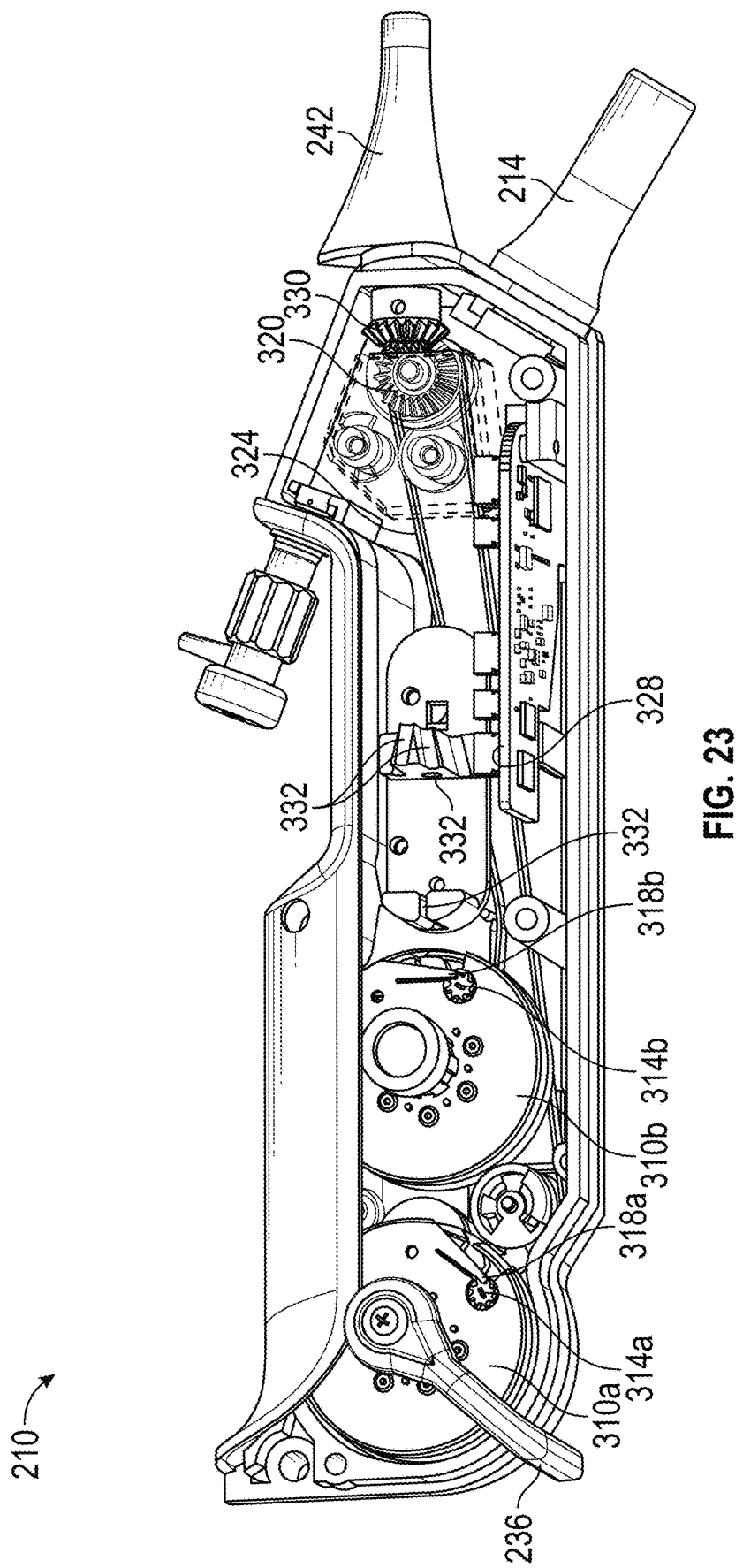
FIG. 23 illustrates some of the internal components of an example endoscope base.

FIG. 23 illustrates some of the internal components of the endoscope base 211. A first side view of the endoscope base 211 is shown with a portion of the housing 212 removed so as to view some of the internal components. As shown, two pulleys (or pulley assemblies), first pulley 310a and second pulley 310b, are positioned within the housing 212. In this embodiment, each of the first pulley 310a and the second pulley 310b is associated with two of four articulation directions of the elongated shaft. In some embodiments, each plane of articulation (e.g., up-down or left-right) can be linked to one pulley assembly. For example, up and down articulation of the elongate shaft can be associated with the first pulley 310a and left and right articulation of the elongate shaft can be associated with the second pulley 310b.

In the illustrated embodiment, the first pulley 310a is rotatably mounted to the instrument base and operatively coupled to a corresponding first robotic drive input. The second pulley 310b is rotatably mounted to the instrument base and operatively coupled to a corresponding second robotic drive input. Rotation of the first robotic drive input can thus cause corresponding rotation of the first pulley 310a, and rotation of the second robotic drive input can cause corresponding rotation of the second pulley 310b. As noted above, rotation of the first pulley 310a can cause articulation of the elongate shaft in the up and down directions, and rotation of the second pulley 310b can cause articulation of the elongate shaft in the left and right directions. Thus, for some embodiments, robotic four-way deflection control can be achieved with the first and second robotic drive inputs and the first and second pulley assemblies 310a, 310b. Alternatively, four separate pulleys could be used with four corresponding robotic drive inputs.

As noted above, the manual actuator 236 can also be rotatably mounted to the instrument base and operatively coupled to the first pulley 310a such that the manual actuator 236 can be used to rotate the first pulley 310a. Rotation of the first pulley 310a can cause articulation of the elongate shaft in the up and down directions. Thus, in the illustrated embodiment, both the manual actuator 236 and the first robotic drive input 227a are each coupled to the first pulley 310a, such that both can cause articulation of the elongate shaft in, for example, the up and down directions. In the illustrated embodiment, the manual actuator 236 is configured as a lever that is rigidly attached to the first pulley 310a. For example, an end 237 of the manual actuator 236 may be attached to a shaft of the first pulley 310a. Thus, any motion of the manual actuator 236 can be directly transferred to the first pulley 310a. Accordingly, the endoscope 210 is configured for manual two-way deflection control (with the manual actuator 236) and four-way deflection control (with the first and second robotic drive inputs).

In the illustrated embodiment, the second pulley 310b is only articulable with the second robotic drive input 227b. In some embodiments, a second manual actuator (not illustrated) can be coupled to the second pulley 310b to further allow manual control of the elongated shaft in, for example, the left and right directions.

Robotic shaft roll may be achieved by a first bevel gear 320 and a second bevel gear 330. The first bevel gear 320 can be attached or otherwise operatively coupled to the third robotic drive input, such that rotation of the third robotic drive input can cause rotation of the first bevel gear 320. The second bevel gear 330 can be attached to the proximal end of the elongate shaft of the endoscope 210 such that rotation of the second bevel gear 330 can cause rotation of the elongate shaft relative to the endoscope base 211. The first and second bevel gears 320, 330 can be engaged to transfer rotational movement of the third robotic drive input to the elongate shaft of the endoscope 210. For example, as shown, a drive belt 324 may be used to operatively couple the first bevel gear 320 to the third robotic drive input (not shown) from a distance. The third drive input may be proximal of the first bevel gear 320. The third drive input may be disposed between the first and second robotic drive inputs of the endoscope 210. Other methods and mechanisms for transferring rotational motion of the third robotic drive input to the elongate shaft of the endoscope 210 are also possible. In some embodiments, as the elongate shaft is rolled, the internal components (such as coil pipes, pull wires, electrical wires, and fiber optics) are allowed to twist as they may be fixed to both the proximal and distal ends of the elongate shaft of the endoscope 210. Twisting of the internal components can be achieved throughout much of the length of the elongate shaft, minimizing the resultant force/torque applied to the proximal and distal terminations.

The endoscope 210 can also include an electronic controller 328. The electronic controller 328 may be coupled to power via the power access 214. The electronic controller 328 can be configured to provide electronic control for one or more elements that is disposed inside the working channel of the elongate channel of the endoscope 210. For example, the endoscope 210 may include a camera, a light source, microphone, another sensor, and/or another tool for use during a medical procedure. The electronic controller 328 can provide power and/or signal for one or more of these tools. Additionally or alternatively, the electronic controller 328 may receive signal from one or more of these tools and pass that information to a computer (not shown). For example, the electronic controller 328 may pass video and/or audio signal to a remote display to aid a practitioner during a surgery.

The endoscope 210 may include one or more guide elements 332. The guide elements 332 can be positioned and sized to receive one or more pull wires therethrough and to promote their passage through the working channel of the elongate shaft of the endoscope 210. The guide elements 332 may advantageously reduce damaging effects of friction on the pull wires as they articulate the elongate shaft. The guide elements 332 can guide the pull wires between the first and/or second pulley assemblies 310a, 310b and the endoscope outlet 242. A first level of guide elements 332 may be configured to guide the pull wires from the first pulley 310a, and a second level of guide elements 332 can be configured to guide the pull wires from the second pulley 310b. The first and second levels may be spaced from each other (e.g., along an axis approximately parallel to an axis of rotation of one or more of the first and/or second pulley assemblies 310a, 310b).

One or each of the pulleys 310a, 310b can include corresponding pulley ratchets 314a, 314b and/or pulley lock mechanisms 318a, 318b, such as shown in FIG. 23. For clarity, reference will be made to the first pulley 310a, but the same functionality may apply to the second pulley 310b. The pulley ratchets 314a, 314b can be used to provide initial tension to the corresponding pulleys 310a, 310b, such as during manufacturing. Thus, once the pull wires are properly tensioned by rotating the pulley ratchets 314a, 314b, the pulley lock mechanisms 318a, 318b prevent the pulley ratchets 314a, 314b from rotating in the opposite direction.

Figure 24:
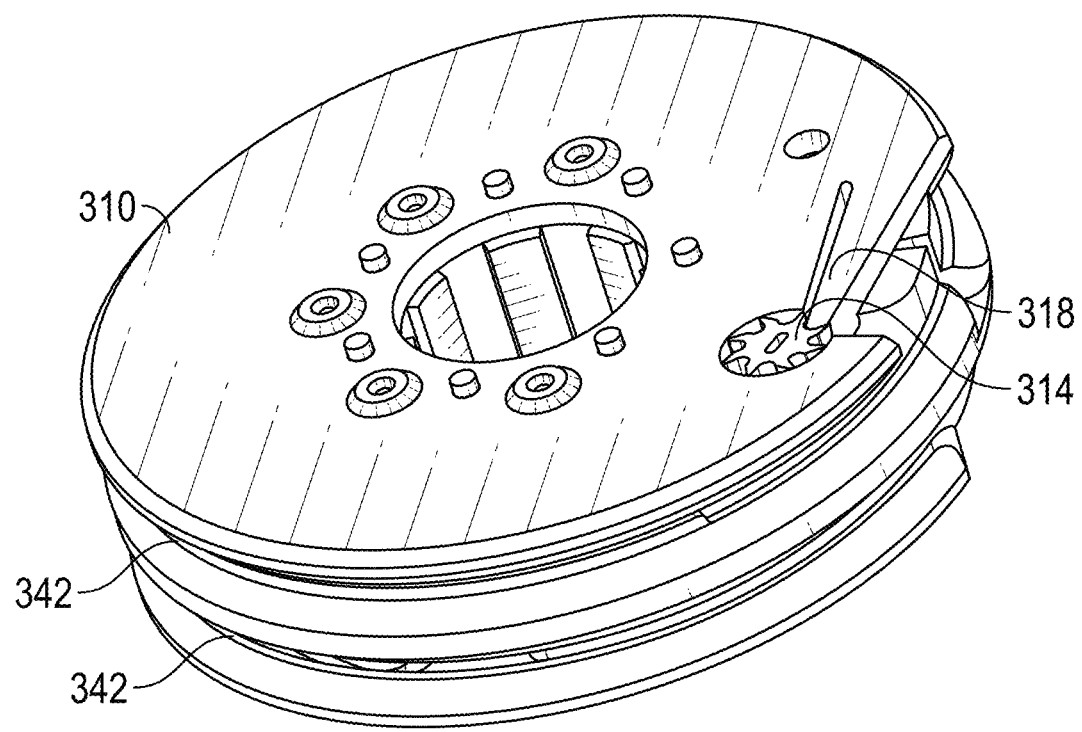
FIG. 24 shows a top perspective view of an example pulley.

An example pulley 310 is illustrated in FIG. 24. Such a pulley 310 may be used for one or both of the pulleys 310a, 310b discussed above. As illustrated, the pulley 310 includes two pull wire spool elements 342. Each pull wire spool element may be configured to spool a corresponding pull wire in a direction opposite the other. For example, a first pull wire spool element may spool a pull wire in a clockwise direction while a second pull wire spool element may spool a corresponding pull wire in a counterclockwise direction. Thus, each pulley 310 can rotate in a first direction, causing one of the pull wires to unspool (e.g., extend) while causing another of the pull wires to spool (e.g., retract). In some embodiments, a manual actuator (e.g., the manual actuator 236) can be coupled to the pulley 310 so that movement (e.g., rotation) of the manual actuator results in rotation of the pulley 310. Additionally or alternatively, rotation of the pulley 310 (e.g., robotically) may also cause movement of the manual actuator. The pulley ratchet 314 and the pulley lock mechanism 318 can operate together to allow for the pull wires of the pulley 310 to be tensioned before use. The pulley ratchet 314 can be used to provide initial tension to the pulley 310, such as during manufacturing. The pulley lock mechanism 318 prevents the pulley ratchet 314 from rotating in the opposite direction.

As mentioned above, the endoscope 210 may include pull wires for articulating the elongate shaft. In some embodiments, one pull wire can be associated with each direction of articulation of the elongate shaft. In some embodiments, the endoscope 210 includes four pull wires, such that four-way deflection control is possible. In such cases, for example, a first pull wire can be associated with deflection in an up direction, a second pull wire can be associated with deflection in a down direction, a third pull wire can be associated with deflection in a right direction, and a fourth pull wire can be associated with deflection in a left direction. The pull wires can extend between the first and second pulleys 310a, 310b and the distal end of the elongate shaft of the endoscope 210. At the distal end of the elongate shaft, the pull wires can be connected to thereto.

At the first and second pulleys 310a, 310b each of the pull wires can be wound, wrapped, or otherwise mounted on or connected to the one of the pulleys of the two pulley assemblies. For example, considering the pulley 310 of FIG. 24, the first pull wire (e.g., associated with upward deflection) can be wound within a first pull wire spool element and the second pull wire (e.g., associated with downward deflection) can be wound within a second pull wire spool element. The opposite spooling of the two pull wires can allow rotation of the pulley 310 to pull on either the first pull wire (e.g., to cause upward deflection) or the second pull wire (e.g., to cause downward deflection) depending on the direction that the pulley 310 is rotated. The third and fourth pull wires can similarly be wound on the a second pulley (e.g., the second pulley 310b) for, for example, left and right deflection control. In some embodiments, a spring can additionally or alternatively be used to apply tension to one or more pull wires.

Figure 25:
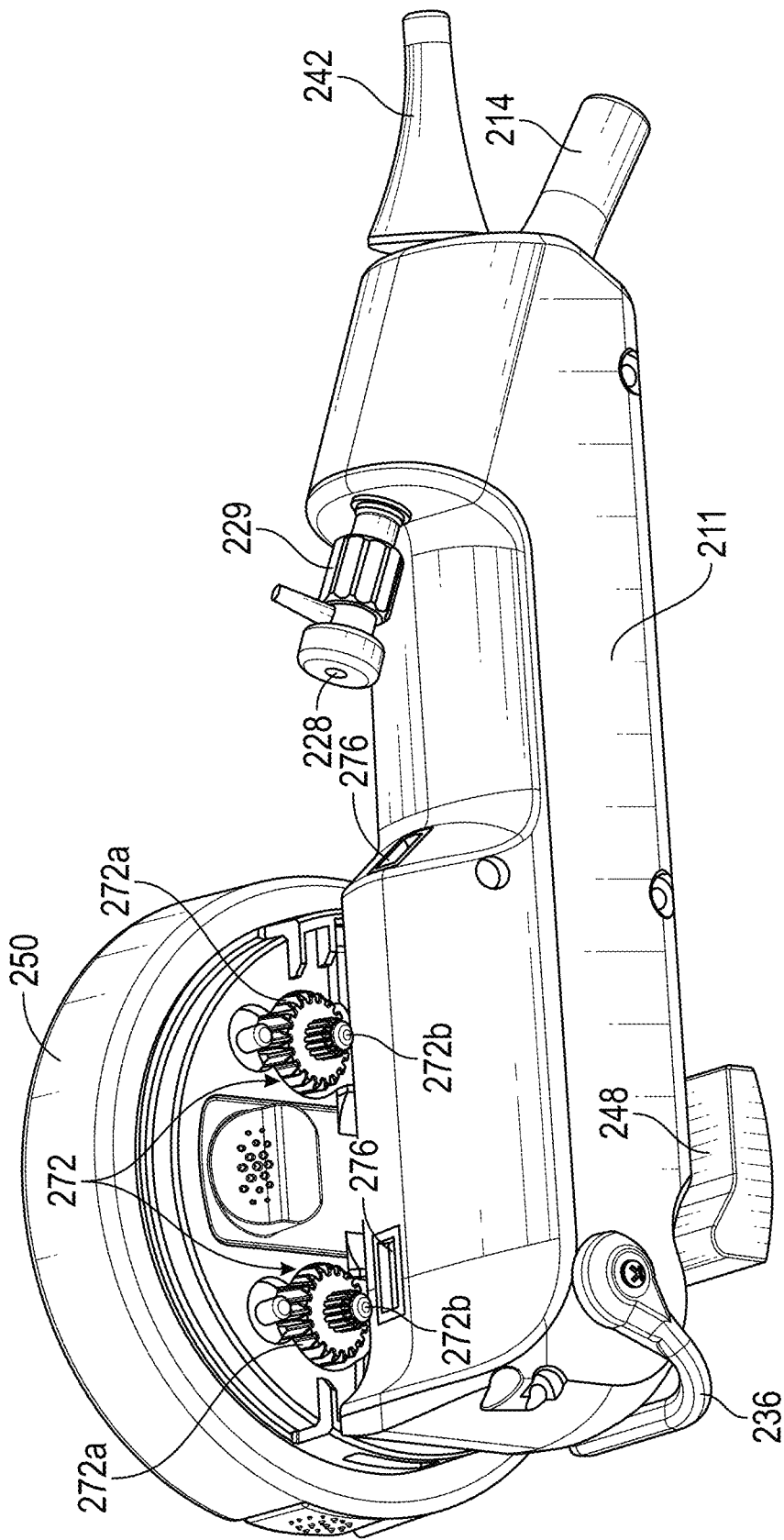
FIG. 25 illustrates views of an example endoscope base of the medical instrument system 200 attached to an embodiment of a robotic instrument drive adapter.

FIG. 25 illustrates views of the endoscope base 211 of the medical instrument system 200 attached to an embodiment of a robotic instrument drive adapter 250. The medical instrument system 200 can include an elongate shaft (not shown). The robotic instrument drive adapter 250 can include a coupling face to which the endoscope base 211 can be attached. In some embodiments, the robotic instrument drive adapter 250 can be configured as a sterile adapter. In some embodiments, a separate adapter (such as sterile adapter) can be positioned between the endoscope base 211 and the robotic instrument drive adapter 250. The sterile adapter can provide a sterile boundary between the endoscope base 211 and the robotic instrument driver. The coupling face can include robotic drive outputs positioned thereon, such as instrument drive outputs 272 (or the endoscope drive outputs 274, described below). One or more of the robotic drive outputs can engage corresponding robotic drive inputs of the endoscope base 211 and/or of the instrument base 221. The robotic instrument driver can include one or more motors for driving the robotic drive outputs. The robotic drive outputs may be configured as gears, protruding splines, and/or the like. The robotic instrument drive adapter 250 can be configured to attach to a robotic arm or other instrument positioning device as shown, for example, in FIGS. 16 and 17.

In some embodiments, when the endoscope base 211 is attached to the robotic instrument drive adapter 250, the manual actuator 236 and/or other actuators can remain exposed and accessible. In some embodiments, the instrument 200 can be configured such that connection of the endoscope base 211 to the robotic instrument drive adapter 250 causes disengagement of the manual actuator 236.

The shape of the endoscope base 211 can leave one or more of the instrument drive outputs 272 exposed. The exposed instrument drive outputs 272 can thus remain accessible to be connected to other tools (e.g., a basketing tool, a laser tool, etc.). In some embodiments, prior to connecting the endoscope base 211 to the robotic instrument drive adapter 250, the manual actuator 236 is operably connected to the pulley assembly 229 such that the manual actuator 236 can be actuated to cause articulation of the instrument 200 as described above. In some embodiments, after the endoscope base 211 is connected to the robotic instrument drive adapter 250, the manual actuator 236 is disengaged from the pulley assembly 229 such that the manual actuator 236 is not useable to articulate the instrument 200 while the endoscope base 211 is connected to the robotic instrument drive adapter 250.

In some embodiments, connection of the endoscope base 211 to the robotic instrument drive adapter 250 causes disengagement of the manual drive mechanism. Disengagement may be automatic. For example, inserting instrument drive outputs 272 of the robotic instrument drive adapter 250 into corresponding inputs of an instrument (e.g., the instrument 220 discussed below), can cause disengagement by, for example, disengaging the manual actuator 236 from the first pulley 310a. In some embodiments, the manual actuator 236 can be reengaged when one or more instruments of the medical instrument system 200 is removed from the robotic instrument drive adapter 250.

Certain drive outputs of the robotic instrument drive adapter 250 can provide tiered gearings. Such tiered gearings may allow for greater versatility in the compatibility of medical instruments with the robotic instrument drive adapter 250. For example, each of the instrument drive outputs 272 can include first geared section 272a and a second geared section 272b. The first geared section 272a can be configured to couple with a particular tool element while the second geared section 272b can be configured to couple with a different tool element. The first geared section 272a can have gears about a greater radius than that of the second geared section 272b. Thus, for certain implementations, the first geared section 272a can be used to impart a greater torque on a corresponding drive input (compared to the second geared section 272b) while the second geared section 272b can impart a relatively greater rotational velocity to a corresponding drive input (compared to the first geared section 272a). Even within the same instrument, a first drive input of the instrument may be configured for a gear radius of the first geared section 272a while a second drive input may be configured for the second geared section 272b.

The robotic instrument drive adapter 250 may include a shoulder 248. The shoulder 248 can provide additional support for the endoscope 210 to promote a better fit of the couplings described herein and to reduce loose fittings. Additionally or alternatively, in some embodiments, the robotic instrument drive adapter 250 may include a corresponding shoulder for another instrument. In some embodiments, the shoulder 248 is omitted.

Figure 26:
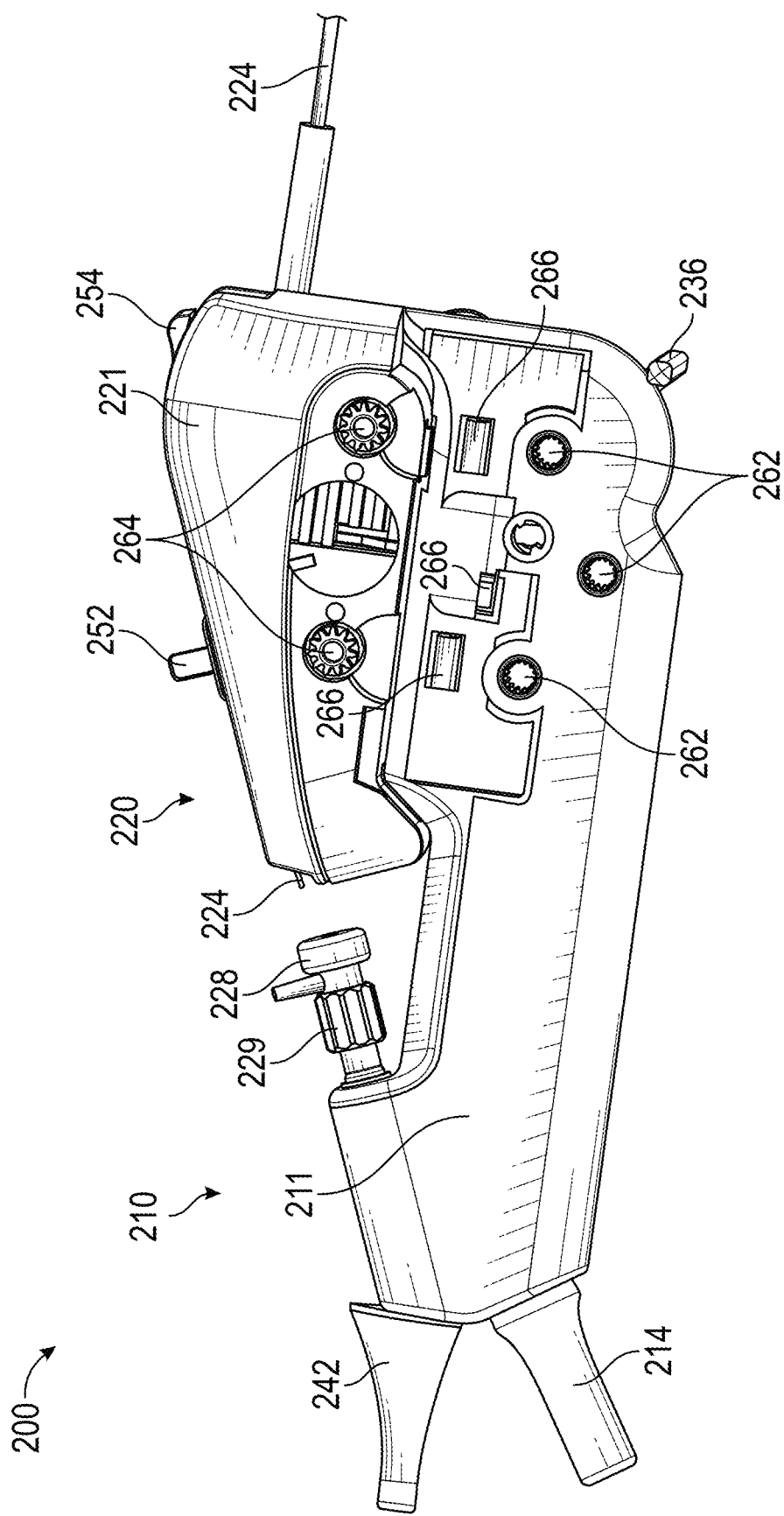
FIG. 26 illustrates a bottom view of an example medical instrument system according to one configuration.

FIG. 26 illustrates a bottom view of an example medical instrument system 200 according to one configuration. As illustrated, the medical instrument system 200 includes the endoscope 210 and an instrument 220. The instrument 220 includes an instrument base 221 and an elongate shaft 224. The elongate shaft 224 may extend proximally from a proximal portion of the instrument base 221. In some embodiments, however, the elongate shaft 224 may extend distally from an instrument base 221 The elongate shaft 224 may be configured to couple into the instrument shaft inlet 228 of the endoscope 210. In this way, the elongate shaft 224 can be received into the working channel (not shown) of the elongate shaft of the endoscope 210.

The instrument 220 can include one or more robotic instrument drive inputs 264. One or more of the robotic instrument drive inputs 264 may be configured to couple with corresponding drive outputs (e.g., the instrument drive outputs 272) of a robotic instrument drive mechanism (e.g., the robotic instrument drive adapter 250). The elongate shaft 224 is configured to be inserted into a patient during a medical procedure. The elongate shaft 224 can be configured to be articulable and/or controllable, such that the elongate shaft can be navigated and steered through the patient's anatomy. Additionally or alternatively, certain instruments 220 may be configured to have additional functionality. For example, a basketing tool may be configured to deploy and to retract in order to collect material (e.g., calcified stones) from within the patient. Such functionality may be robotically controlled by one or more of the robotic drive inputs.

In some configurations, the instrument 220 may be controlled manually additionally or alternatively to the robotic control. As shown in FIG. 26, the instrument 220 can include a first instrument actuator 252 and a second instrument actuator 254. The first instrument actuator 252 may be configured to control a first degree of motion (e.g., proximal or distal movement). The second instrument actuator 254 may be configured to control a second degree of motion (e.g., deployment/retraction or open/close of the tool). Because the elongate shaft 224 can be coupled into the elongate shaft of the endoscope 210 (e.g., via the instrument shaft inlet 228), additional articulation of the elongate shaft 224 may be possible by controlling the elongate shaft of the endoscope 210 directly, as described above. Thus, in some embodiments, the elongate shaft 224 may be configured to be controlled in five degrees of freedom: left-right, up-down, rotation (e.g., roll), proximal-distal movement, and deploy-retract (e.g., basket deployment). These degrees of freedom may be shared between the endoscope 210 and the instrument 220. However, because the endoscope 210 and the instrument 220 can be coupled together as shown, the ergonomic shape of the medical instrument system 200 can allow a practitioner to readily control the elongate shaft 224 robotically and/or manually as needed.

As shown, in some embodiments, the elongate shaft 224 can extend proximally from a proximal portion of the instrument 220. For example, a laser tool may include a fiber that advantageously includes a service loop. A "service loop" can include an extra length of an elongate and flexible shaft that provides a degree of freedom for translation along the shaft axis and/or axial motion of the flexible shaft (e.g., extension, retraction). The service loop can include an extra length of the elongate shaft 224 to allow, for example, for easier manual accessibility and/or freedom of movement. A service loop does not necessarily need to form a circular or 360 degree loop but can be any bent extra length of the flexible shaft. In some embodiments, the service loop can be formed by looping the flexible shaft with a broad radius external to a medical instrument base. The radius of the service loop can be formed near a proximal portion of the instrument base and/or proximally from the inlet of the endoscope base. In some embodiments, the service loop may be formed proximally from a proximal portion of the elongate shaft of the instrument, the endoscope, or both. A service loop does not necessarily require a particular length. Nor does the service loop need to extend a minimum arc length. For example, the service loop may extend about 5 degrees, about 10 degrees, about 20 degrees, about 30 degrees, about 45 degrees, about 60 degrees, about 75 degrees, about 100 degrees, about 120 degrees, about 140 degrees, about 160 degrees, about 180 degrees, about 200 degrees, about 225 degrees, about 250 degrees, about 275 degrees, about 300 degrees, about 315 degrees, about 330 degrees, about 350 degrees, about 360 degrees, any number of degrees there between, or fall within any range having endpoints therein. As noted above, the basket is deployed by a movement in a first direction of the basket relative to a sheath (e.g., a relative advancement of the basket) and/or retracted by a movement in an opposite direction relative to the sheath (e.g., a relative retreat of the basket). With regard to a laser tool, the laser tool may include a laser fiber and a protective sheath. Other examples and tools are possible with the instrument 220. The elongate shaft 224 may loop around as described with reference to FIG. 21B and as described below.

Figure 27:
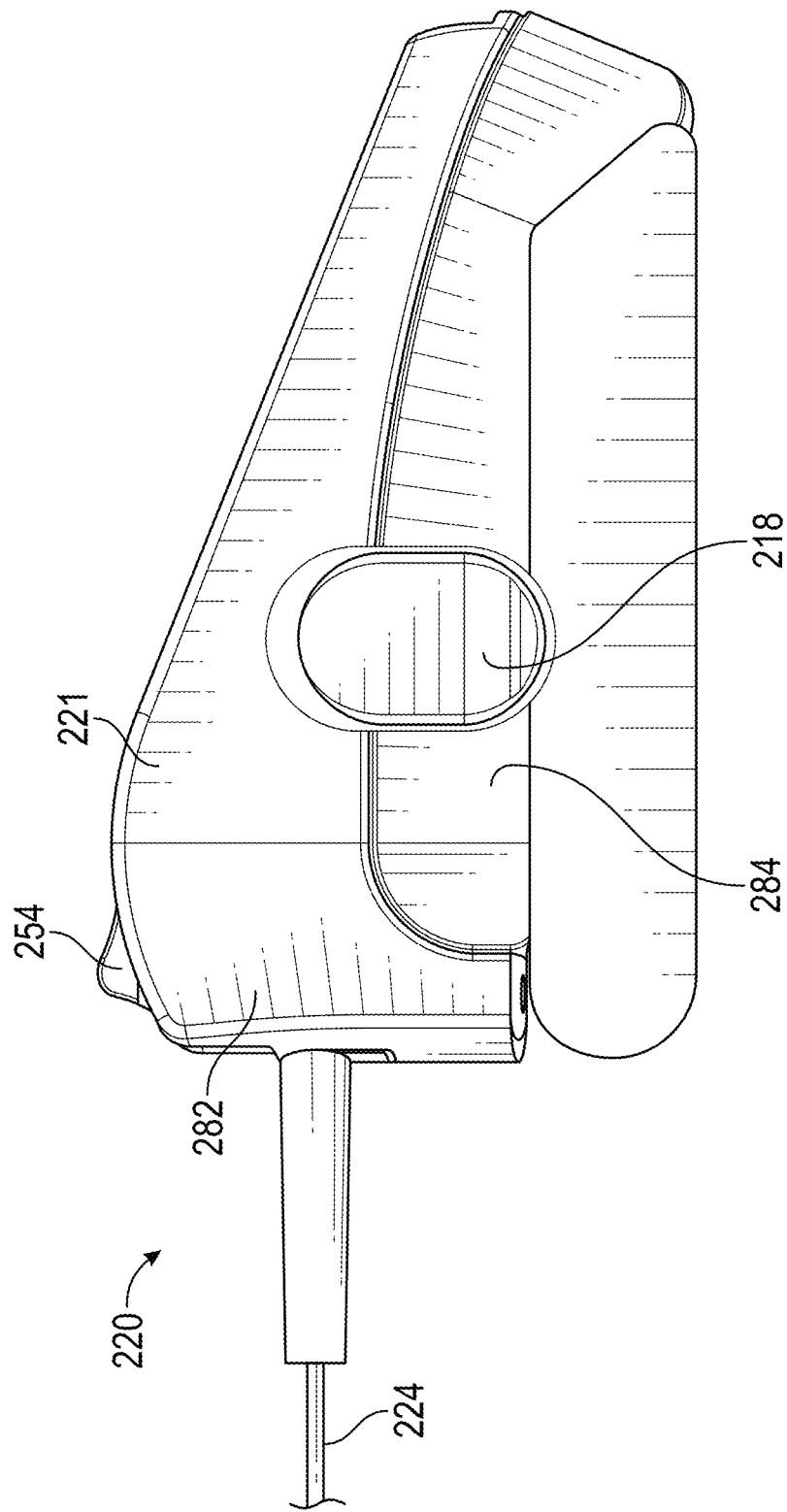
FIG. 27 shows a top view of an example instrument, according to an embodiment.

FIG. 27 shows a top view of an example instrument 220, according to an embodiment. The instrument base 221 can include in some embodiments a first housing element 282 and a second housing element 284. The first and second housing elements 282, 284 may be joined together to form the housing of the instrument base 221. The second housing element 284 may include coupling elements for coupling with the endoscope 210. The instrument button 218 may be actuated to decouple the instrument 220 from the endoscope 210. Unless actuated, the instrument button 218 can be biased to maintain the instrument 220 coupled to the endoscope 210. The instrument button 218 can be manipulated to decouple the instrument 220 from the endoscope 210. For example, in some embodiments a user may slide the instrument button 218 to disengage the instrument 220 from the endoscope 210. In some embodiments, the instrument button 218 may disposed instead on the endoscope 210 to allow a user to decouple the endoscope 210 from the instrument 220 via the endoscope 210.

Figure 28:
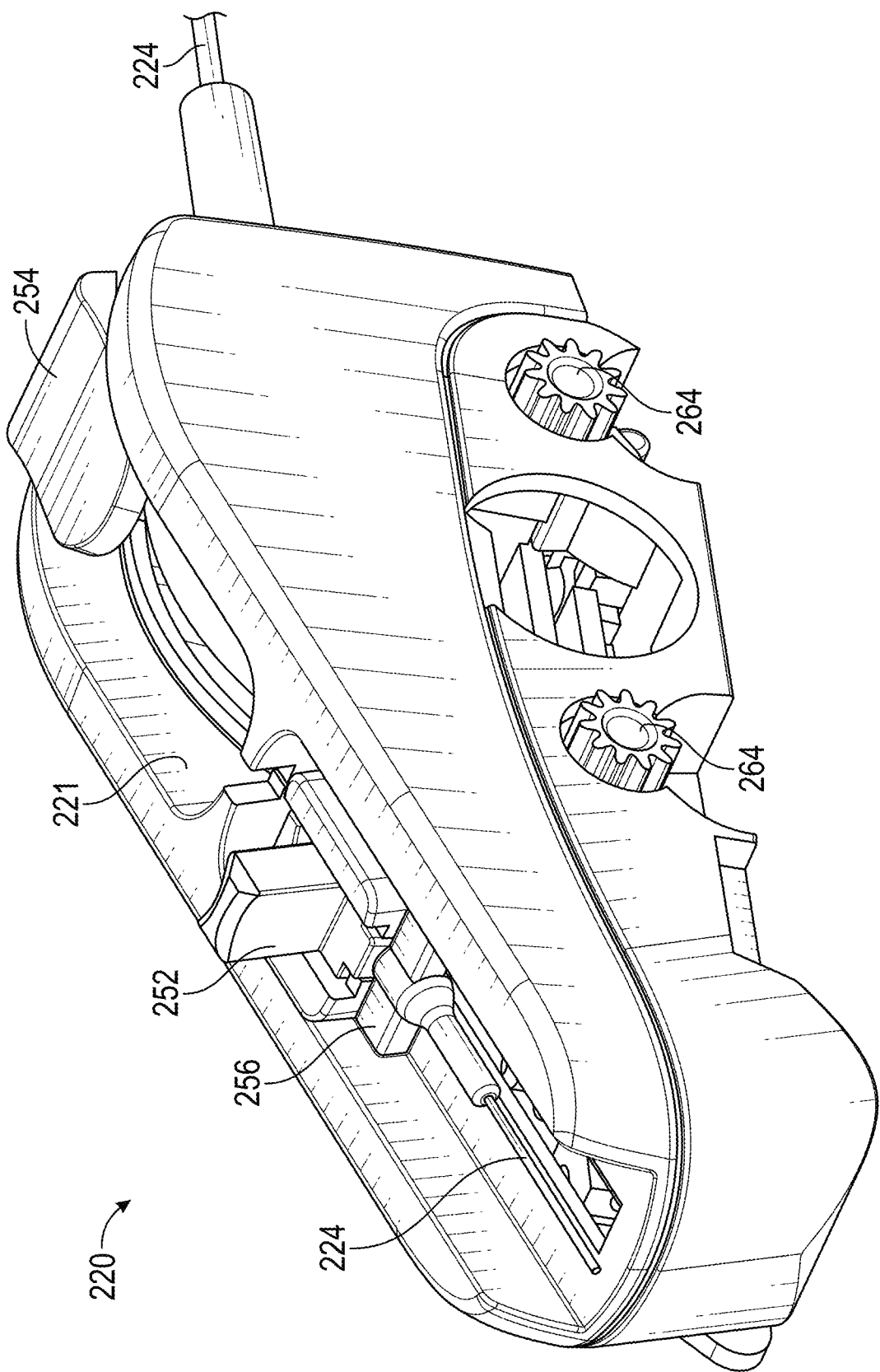
FIG. 28 shows a perspective bottom view of the instrument of FIG. 27, according to an embodiment.

FIG. 28 shows a perspective bottom view of the instrument 220 of FIG. 27, according to an embodiment. The instrument 220 can include an instrument shaft coupler 256. The instrument shaft coupler 256 can be fixedly coupled to the elongate shaft 224 to prevent relative rotation and/or translation of the elongate shaft 224. In some designs, the instrument shaft coupler 256 comprises an overmolded portion of the elongate instrument 224. The instrument shaft coupler 256 can be decoupled from the first instrument actuator 252 to allow a practitioner to manually manipulate the elongate shaft 224 without controlling the instrument base 221. Once finished with its use, a practitioner can re-couple the instrument shaft coupler 256 to the first instrument actuator 252. The instrument shaft coupler 256 can include an insertion element that is received by a receiving element of the first instrument actuator 252. Additionally or alternatively, the first instrument actuator 252 can include an insertion element that is received by a receiving element of the instrument shaft coupler 256. The first instrument actuator 252 can allow a practitioner to manually control the longitudinal position (e.g., proximal/distal) of the elongate shaft 224. The second instrument actuator 254 can allow the practitioner to deploy and/or retract the elongate shaft 224. Each of the first and second instrument actuators 252, 254 are shown as linear actuators. However, other types of actuators (e.g., wheels, levers, buttons, etc.) may be used.

Figure 29:
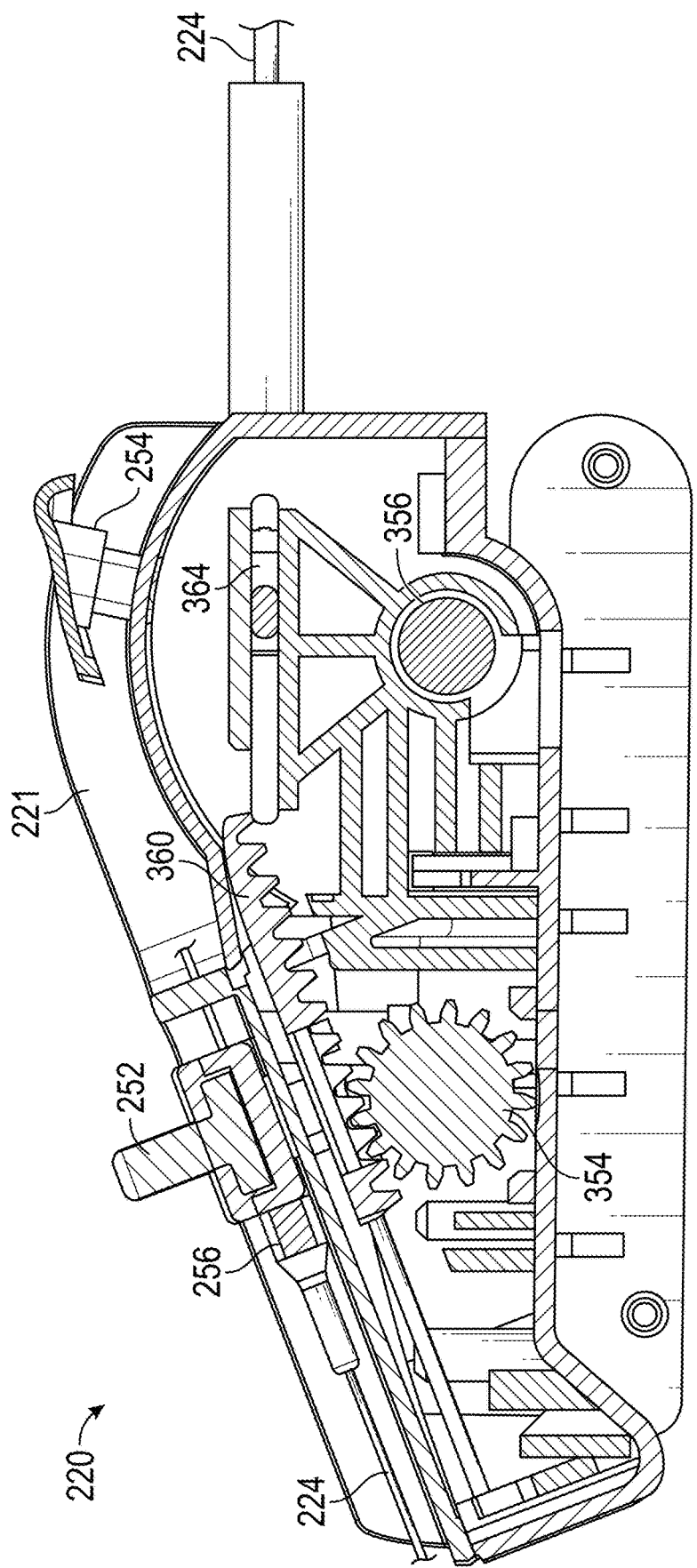
FIG. 29 shows a cross section of a bottom view of the instrument of FIG. 28.

FIG. 29 shows a cross section of a bottom view of the instrument 220 of FIG. 28. As shown, the instrument 220 can include a first instrument drive member 354 and a second instrument drive member 356. The first and second instrument drive members 354, 356 are coupled to the corresponding robotic instrument drive inputs 264 (shown in FIG. 28). The first and second instrument drive members 354, 356 may be fixedly coupled to the corresponding robotic instrument drive inputs 264. The first and second instrument drive members 354, 356 can be coupled to corresponding first and second instrument actuators 252, 254. For example, as shown, the first instrument drive member 354 is a circular gear and is coupled to the first linear instrument actuator 360, which is shown as a linear gear. Other options are possible. Thus, as the first instrument drive member 354 rotates, the first linear instrument actuator 360 translates (e.g., longitudinally). As shown, the translation of the first linear instrument actuator 360 also drives the first instrument actuator 252. Additionally or alternatively, the first instrument actuator 252 may be able to drive a translation of the first linear instrument actuator 360, which then drives a rotation of the first instrument drive member 354.

The second instrument drive member 356 is shown as being a keyed element. The second instrument drive member 356 is coupled to a second linear instrument actuator 364. As the second instrument drive member 356 rotates, the second linear instrument actuator 364 translates. This translation may cause deployment of the instrument in certain embodiments. As the second linear instrument actuator 364 translates, the second instrument actuator 254 may also be caused to translate, even when the second linear instrument actuator 364 is being driven robotically. Additionally or alternatively, when the second linear instrument actuator 364 is being driven manually (e.g., via the second instrument actuator 254), then this actuation may drive a rotation of the second instrument drive member 356. The manual and robotic actuation may be used together or alone. In some designs, a portion of the elongate shaft 224 terminates at a coupling with the second linear instrument actuator 364 inside the instrument base 221.

Although the first and second linear instrument actuators 360, 364 have been discussed above as controlling certain degrees of freedom, other options are possible. For example, the first linear instrument actuator 360 may be configured to control a translation of the elongate shaft 224 while the second linear instrument actuator 364 may be configured to control a translation of a portion of the elongate shaft 224 (e.g., an outer sheath thereof). Thus, a translation of the elongate shaft 224 (without deployment) may be achieved through the simultaneous translation of both the first and second linear instrument actuators 360, 364. A deployment or retraction of the elongate shaft 224 can then be achieved by a corresponding advancement or retreat of the elongate shaft 224 relative to the outer portion of the instrument. Which of the first and second linear instrument actuators 360, 364 controls which degree of freedom may be reversed as desired. Thus, various configurations of control may be achieved by modifying which degree of freedom is controlled by each of the first and second linear instrument actuators 360, 364.

Figure 30A:
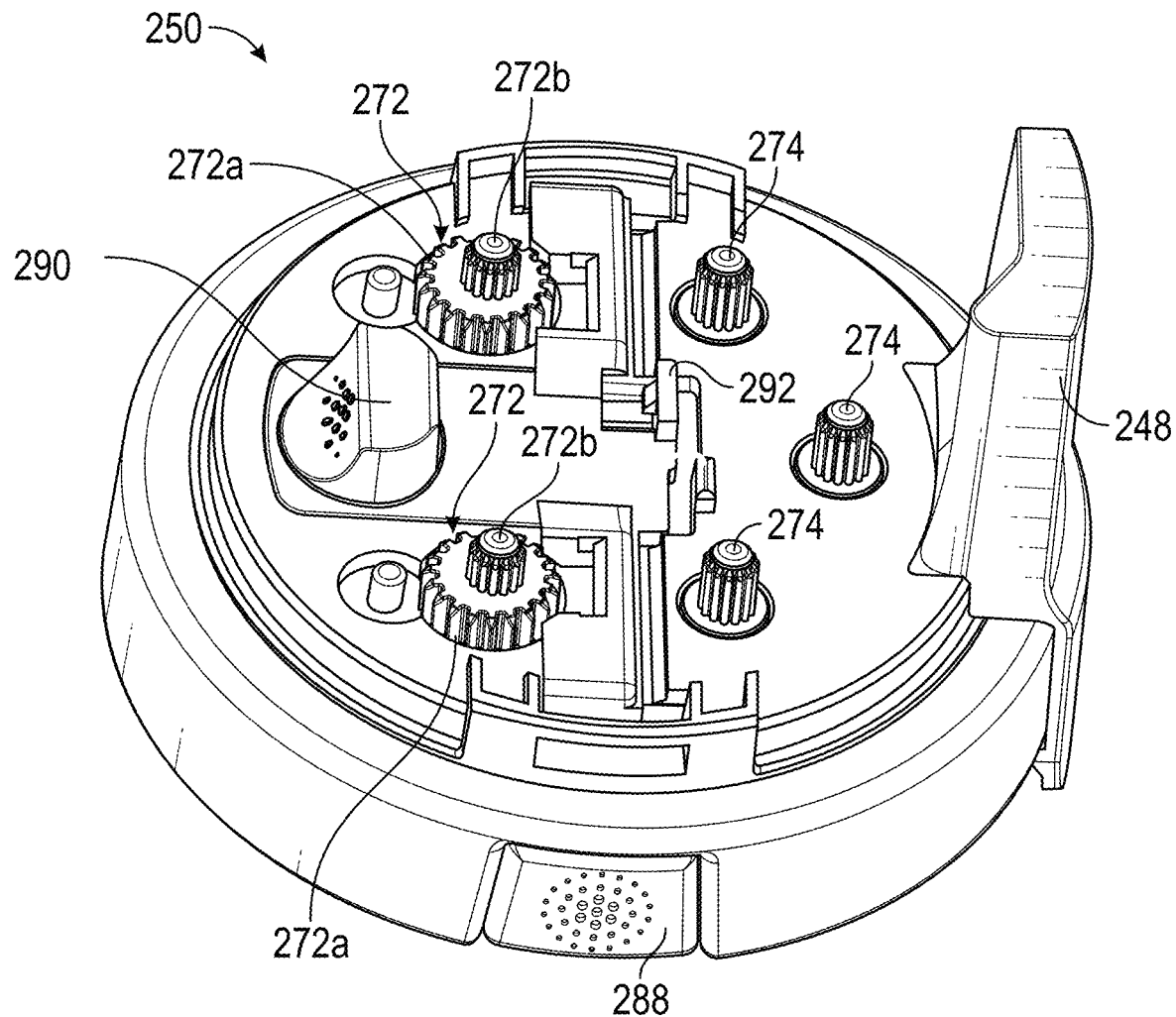
FIG. 30A-B show perspective views of an example robotic instrument drive adapter.

FIG. 30A shows a top perspective view of an example robotic instrument drive adapter 250. The robotic instrument drive adapter 250 can include one or more instrument drive outputs 272 and/or one or more endoscope drive outputs 274. As shown, the robotic instrument drive adapter 250 includes two instrument drive outputs 272 for coupling with the instrument 220 and endoscope drive outputs 274 for coupling with the endoscope 210. The robotic instrument drive adapter 250 can include one or more drive mechanism coupling elements 292. As shown, the robotic instrument drive adapter 250 includes a drive mechanism coupling element 292. The one or more drive mechanism coupling element 292 can be adapted to couple with one or more corresponding coupling elements of the endoscope 210 (e.g., the endoscope coupling elements 266) and/or of the instrument 220. In some embodiments, the drive mechanism coupling elements 292 are configured only to couple with either the endoscope 210 or the instrument 220, but not both. However, in some embodiments, the robotic instrument drive adapter 250 includes drive mechanism coupling elements 292 that are configured to couple with both the endoscope 210 and the instrument 220. Other configurations are possible. The shoulder 248, which can promote better coupling with the endoscope 210, is also shown. A release member 288 may be included in the robotic instrument drive adapter 250. The release member 288 can be depressed to allow, for example, for decoupling of the robotic instrument drive adapter 250 from the instrument drive mechanism on the robotic arm. In some embodiments, the release member 288 decouples the endoscope coupling elements 266 from corresponding drive mechanism coupling elements 292.

The robotic instrument drive adapter 250 may include an endoscope release actuator 290 that is configured to allow a user to decouple the endoscope 210 from the robotic instrument drive adapter 250. In some embodiments, the endoscope release actuator 290 is coupled to the drive mechanism coupling element 292 such that when the endoscope release actuator 290 is depressed, the drive mechanism coupling element 292 experiences a corresponding actuation (e.g., depression or translation). Thus, in some embodiments a user can disengage the endoscope 210 from the robotic instrument drive adapter 250 by depressing the endoscope release actuator 290. The endoscope release actuator 290 may be biased in a closed position. In some embodiments, the endoscope release actuator 290 may be disposed on the endoscope 210 so that a user may decouple the endoscope 210 from the robotic instrument drive adapter 250 via the endoscope 210. According to some embodiments, the latching scheme for the instrument 220 and endoscope 210 can provide improved usability and/or safety. In the embodiment shown, the release actuator 290 on the robotic instrument drive adapter 250 cannot be operated until the working channel tool is first detached from the endoscope 210, providing a safety constraint. In other embodiments, the release actuator 290 can be operated while the working channel tool is still attached to the endoscope, for example, by providing a cutout or recessed in the working channel tool that allows a user to access the release actuator 290 with their finger.

The robotic instrument drive adapter 250 can have inputs and/or outputs (e.g., the adapter drive inputs 296 shown in FIG. 30B) to couple to an instrument drive mechanism (e.g., the instrument driver 62 of FIG. 15, the instrument driver 75 of FIG. 16, the instrument drive mechanisms 146A, 146B of FIG. 14). The robotic instrument drive adapter 250 can include or be connected to a sterile liner (e.g., sterile drape) to allow for use in sterile procedures. The robotic instrument drive adapter 250 may be referred to as a sterile adapter. The sterile liner can promote a sterile environment during certain procedures (e.g., surgeries).

Figure 30B:
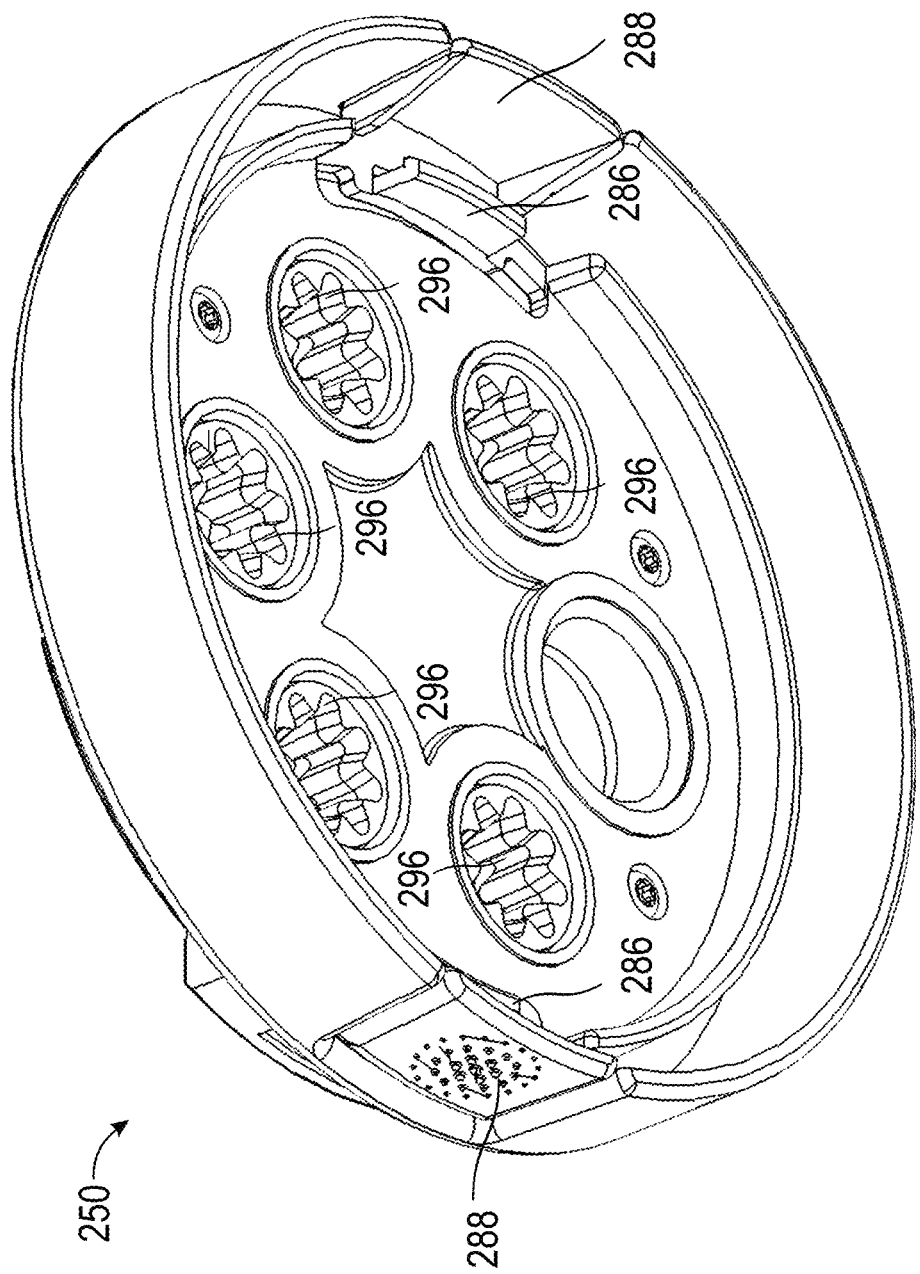

FIG. 30B shows a bottom perspective view of the robotic instrument drive adapter 250 shown in FIG. 30A. As noted above, the robotic instrument drive adapter 250 can include one or more adapter drive inputs 296 that drive corresponding instrument drive outputs 272 and/or endoscope drive outputs 274. The adapter drive inputs 296 are configured to couple to an instrument drive mechanism (e.g., the instrument driver 62 of FIG. 15, the instrument driver 75 of FIG. 16, the instrument drive mechanisms 146A, 146B of FIG. 14). The adapter drive inputs 296 can include receiving elements that couple to protrusions of corresponding drive outputs of the instrument drive mechanism (not shown in FIG. 30B). In some embodiments, the adapter drive inputs 296 may include protrusions that couple to corresponding receiving elements of the drive outputs of the instrument drive mechanism. As shown, the robotic instrument drive adapter 250 can include one or more release members 288 that can be manipulated (e.g., depressed or squeezed) by a user to decouple the robotic instrument drive adapter 250 from the instrument drive mechanism. One or more adapter coupling elements 286 of the robotic instrument drive adapter 250 can couple to the instrument drive mechanism, such as by a snap fit, screw fit, or some other mechanical coupling arrangement. Operation of the release members 288 can decouple the adapter coupling elements 286 from the instrument drive mechanism.

Figure 31:
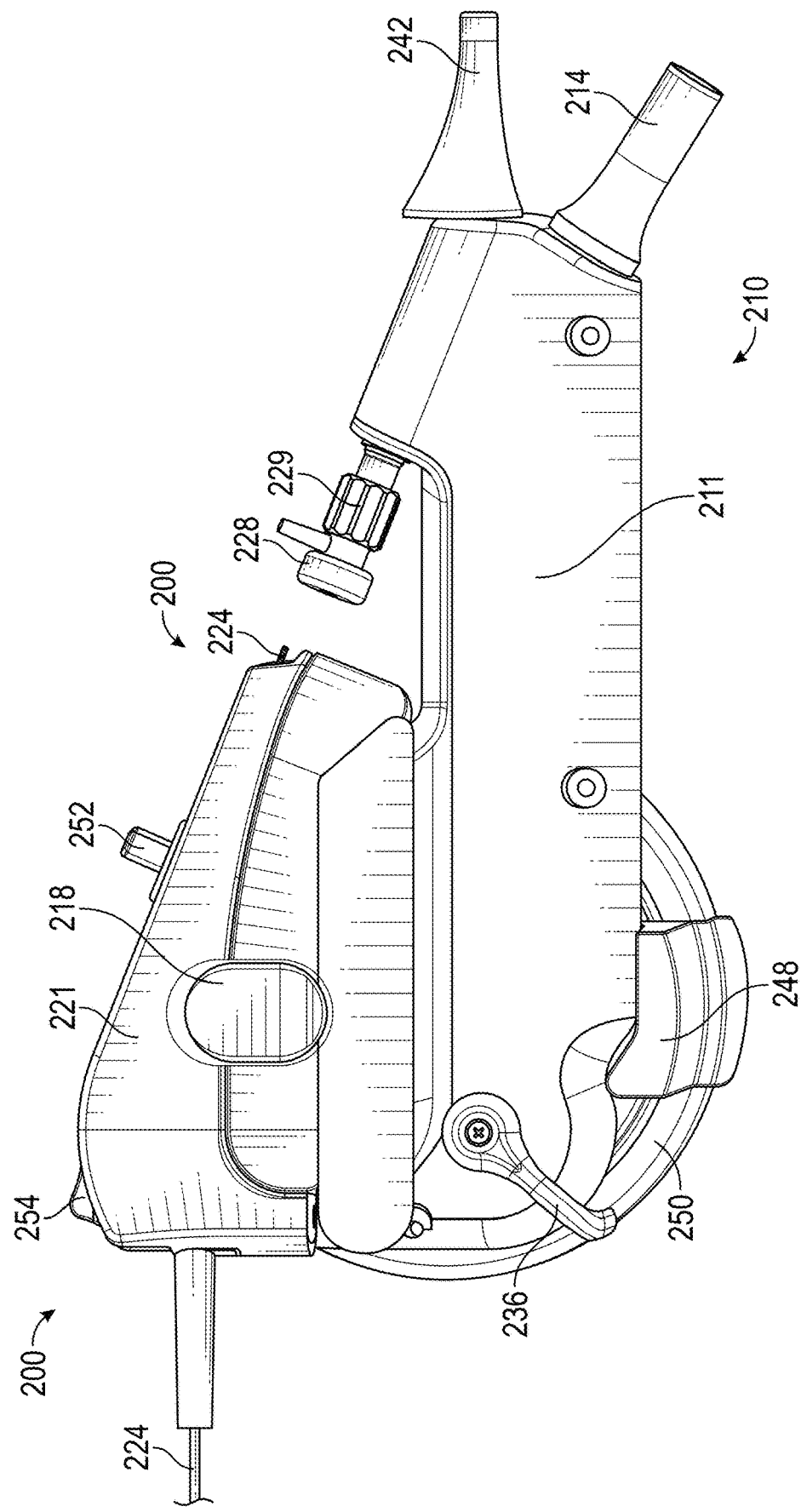
FIG. 31 shows an example medical instrument system with both the endoscope and the instrument coupled to the robotic instrument drive adapter.

FIG. 31 shows an example medical instrument system 200 with both the endoscope 210 and the instrument 220 coupled to the robotic instrument drive adapter 250. One or both of the endoscope 210 and/or instrument 220 may be decoupled (e.g., temporarily) from the robotic instrument drive adapter 250 to be used manually.

Figure 32:
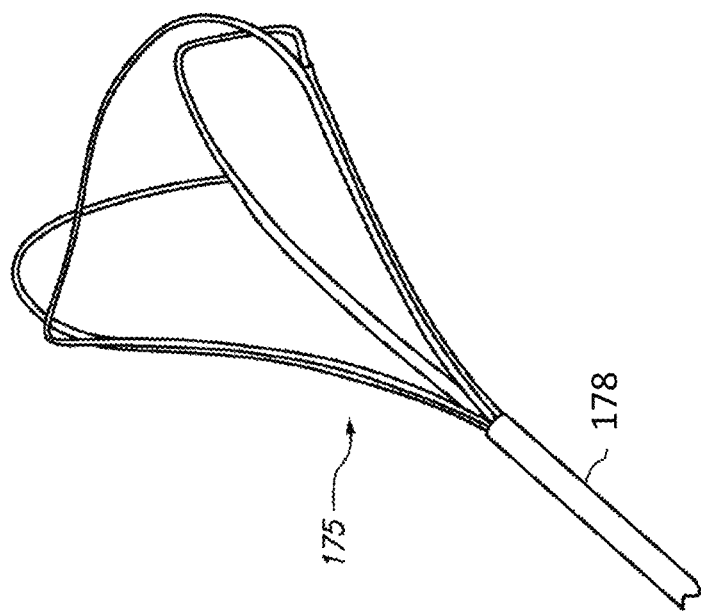
FIG. 32 shows a close up view of the distally located basket tool.

Various medical instruments may be controlled by the medical instruments (e.g., the instrument 220). For example, FIG. 32 shows a close up view of the distally located basket head 175. The basket head 175 may be advanced within the instrument shaft 178 to capture a stone. The instrument shaft 178 may be an outer shaft of any elongate instrument described above (e.g., the elongate shaft 224). Such advancing may be conducted by manual contact with the basket tool through the working channel described above, or via operable coupling with an insertion/retraction and/or actuation means, such as the robotic-based systems described above. Such actuation activates the distal portion or distal end of the shaft, which in this example can involve expanding or contracting the basket head 175 by deploying or withdrawing the basket head relative to an outer sheath or instrument shaft 178. Another medical instrument may include a laser tool (not shown), which can be utilized to incrementally destroy the stone via controlled emission of laser-based energy into the stone. The laser tool can include a laser fiber having a proximal coupling element configured to interface with the instrument base 221 and a distal tip configured to emit laser-based energy to destroy items such as kidney stones. A stone may be attacked with the laser tip in a pattern, to incrementally break the stone into smaller pieces of sub-critical geometry. For example, a "painting" pattern may be utilized wherein the laser tip addresses the stone at multiple points.

3. Implementing Systems and Terminology.

Some nonlimiting examples of the systems described herein are described below.

In a 1st example, a robotic medical instrument system comprises: a first medical instrument comprising an instrument base and an elongate shaft extending from the instrument base, the instrument base including a robotic drive input and a first rotating element coupled to the robotic drive input, wherein the robotic drive input of the first medical instrument is configured to articulate the distal end of the elongate shaft of the first medical instrument, the first medical instrument further comprising an instrument inlet in communication with a working channel extending through the first medical instrument; a second medical instrument comprising an instrument base and an elongate shaft configured to extend through the instrument inlet and partially within the elongate shaft of the first instrument, the second medical instrument including a robotic drive input; and a robotic arm comprising first and second robotic drive outputs, the first robotic drive output configured to drive the robotic drive input of the first medical instrument, and the second robotic drive output configured to drive the robotic drive input of the second medical instrument.

In a 2nd example, the robotic system of example 1, wherein the first rotating element comprises a tensioning ratchet configured to allow for initial tensioning of a pull wire coupled to the first rotating element.

In a 3rd example, the robotic system of any of examples 1-2, wherein the elongate shaft of the second medical instrument extends from a proximal portion of the instrument base of the second medical instrument.

In a 4th example, the robotic system of example 3, wherein the second medical instrument comprises a coupling element, the coupling element operatively coupling the elongate shaft of the second medical instrument to the robotic drive input of the second medical instrument, wherein the robotic drive input of the second medical instrument is operatively coupled to the elongate shaft of the second medical instrument at a point distal to the proximal portion of the instrument base.

In a 5th example, the robotic system of example 4, wherein the second medical instrument further comprises a linear actuator coupled to the coupling element, the linear actuator configured to manipulate the elongate shaft of the second medical instrument longitudinally.

In a 6th example, the robotic system of any of examples 1-5, wherein the second medical instrument comprises a laser tool or a basketing tool.

In a 7th example, the robotic system of any of examples 1-6, wherein a first actuator controls a longitudinal position of at least a portion of the elongate shaft of the second medical instrument.

In a 8th example, the robotic system of example 7, wherein a second actuator controls an activation of a distal portion of the elongate shaft of the second medical instrument.

In a 9th example, the robotic system of any of examples 1-8, wherein the robotic drive input of the second medical instrument is coupled to a sheath of the elongate shaft of the second medical instrument.

In a 10th example, the robotic system of any of examples 1-9, wherein the second medical instrument further comprises a second robotic drive input, wherein the second robotic drive input is coupled to an inner portion of the elongate shaft of the second medical instrument.

In a 11th example, the robotic system of any of examples 1-10, wherein the elongate shaft of the second medical instrument forms a service loop.

In a 12th example, the robotic system of example 11, wherein the service loop extends at least 45 degrees between the instrument inlet of the first medical instrument and the instrument base of the second medical instrument.

In a 13th example, a medical system comprises: an endoscope base having an elongate shaft extending therefrom, the endoscope base having a first robotic drive input and a first manual actuator; and a working channel instrument having an elongate shaft configured to extend within the elongate shaft of the endoscope, the working channel instrument having a second robotic drive input and a second manual actuator, wherein the first and second robotic drive inputs are configured to couple to corresponding first and second robotic drive outputs of a robotic arm, and wherein the first and second manual actuators are configured to be manually actuated when the first and second robotic drive inputs are decoupled from the first and second robotic drive outputs of the robotic arm.

In a 14th example, the medical system of example 13, wherein the working channel instrument comprises an instrument base having a coupling element configured to allow removable coupling of the instrument base to the endoscope base.

In a 15th example, the medical system of any of examples 13-14, wherein the endoscope further comprises a first rotating element that is configured to articulate the distal end of the elongate shaft of the endoscope in a first degree of freedom, and wherein the first manual actuator is configured to allow manual rotation of the first rotating element.

In a 16th example, the medical system of any of examples 13-15, wherein the working channel instrument further comprises an instrument base coupled to the elongate shaft of the working channel instrument, the elongate shaft of the working channel instrument extending from a proximal portion of the instrument base.

In a 17th example, the medical system of any of examples 13-16, wherein the working channel instrument comprises a coupling element operatively coupling the elongate shaft of the working channel instrument to the second robotic drive input, wherein the second robotic drive input of the working channel instrument is operatively coupled to the elongate shaft of the working channel instrument at a point distal to the proximal portion of the instrument base.

In a 18th example, the medical system of example 17, wherein the working channel instrument further comprises a linear actuator coupled to the coupling element, the linear actuator configured to manipulate the elongate shaft of the working channel instrument longitudinally.

In a 19th example, the medical system of any of examples 13-18, wherein the working channel instrument comprises a laser tool or a basketing tool.

In a 20th example, the medical system of any of examples 13-19, wherein the second robotic drive input controls a longitudinal position of at least a portion of the elongate shaft of the working channel instrument.

In a 21st example, the medical system of any of examples 13-20, wherein the second manual actuator controls an activation of a distal portion of the elongate shaft of the working channel instrument.

In a 22nd example, the medical system of any of examples 13-21, wherein the second robotic drive input is coupled to a sheath of the elongate shaft of the working channel instrument.

In a 23rd example, the medical system of any of examples 13-22, wherein the elongate shaft of the instrument forms a service loop between an inlet of the endoscope and an instrument base of the working channel instrument.

In a 24th example, a medical instrument comprises: an instrument base, the instrument base including a robotic drive input and a linear actuator coupled to the robotic drive input, the robotic drive input configured to couple to a corresponding robotic drive output of a robotic arm; and an elongate shaft extending from a proximal portion of the instrument base, wherein the linear actuator couples to a portion of the elongate shaft at a point distal to the proximal portion of the instrument base.

In a 25th example, the robotic system of example 24, wherein the linear actuator comprises a linear gear configured to manipulate a longitudinal position of the elongate shaft.

In a 26th example, the medical instrument of any of examples 24-25, wherein the instrument further comprises a second robotic drive input, the second robotic drive input configured to actuate a distal end of the instrument.

In a 27th example, the medical instrument of example 26, further comprising a manual actuator, the manual actuator further controlling actuation of the distal end of the instrument.

In a 28th example, the medical instrument of any of examples 26-27, wherein the second robotic drive input is configured to expand or retract the distal end of the instrument.

In a 29th example, the medical instrument of any of examples 24-28, wherein the instrument comprises a laser tool or a basketing tool.

In a 30th example, the medical instrument of any of examples 24-29, wherein the elongate shaft forms a service loop extending from the proximal portion of the instrument base to the point distal to the proximal portion.

Implementations disclosed herein provide systems, methods and apparatus related to manually and robotically controllable medical instruments. As discussed above, the medical instruments can be controlled by manual and robotic drive inputs allowing the devices to be used both manually and robotically.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system, comprising:
   a first medical instrument comprising a first instrument base and a first elongate shaft extending from the first instrument base, the first instrument base including a first robotic drive input and a first rotating element coupled to the first robotic drive input, wherein the first robotic drive input is configured to articulate a distal end of the first elongate shaft, the first medical instrument further comprising an instrument inlet providing access to a working channel of the first medical instrument, wherein the first rotating element comprises a tensioning ratchet configured to allow for tensioning of a pull wire coupled to the first rotating element;
   a second medical instrument comprising a second instrument base and a second elongate shaft configured to extend through the instrument inlet and at least partially within the first elongate shaft of the first medical instrument, the second medical instrument including a second robotic drive input; and
   a robotic end effector comprising first and second robotic drive outputs, the first robotic drive output configured to drive the first robotic drive input of the first medical instrument, and the second robotic drive output configured to drive the second robotic drive input of the second medical instrument.

2. The robotic system of claim 1, wherein the second elongate shaft extends from a proximal portion of the second instrument base of the second medical instrument.

3. A robotic system comprising:
   a first medical instrument comprising a first instrument base and a first elongate shaft extending from the first instrument base, the first instrument base including a first robotic drive input and a first rotating element coupled to the first robotic drive input, wherein the first robotic drive input is configured to articulate a distal end of the first elongate shaft, the first medical instrument further comprising an instrument inlet providing access to a working channel of the first medical instrument, wherein the first rotating element comprises a tensioning ratchet configured to allow for tensioning of a pull wire coupled to the first rotating element;
   a second medical instrument comprising a second instrument base and a second elongate shaft configured to extend through the instrument inlet and at least partially within the first elongate shaft of the first medical instrument, the second medical instrument including a second robotic drive input; and
   a robotic end effector comprising first and second robotic drive outputs, the first robotic drive output configured to drive the first robotic drive input of the first medical instrument, and the second robotic drive output configured to drive the second robotic drive input of the second medical instrument;
   wherein:
      the second elongate shaft extends from a proximal portion of the second instrument base of the second medical instrument; and
      the second medical instrument comprises a coupling element operatively coupling the second elongate shaft to the second robotic drive input, wherein the second robotic drive input is operatively coupled to the second elongate shaft at a point distal to the proximal portion of the second instrument base.

4. The robotic system of claim 3, wherein the second medical instrument further comprises a linear actuator associated with the coupling element, the linear actuator being configured to manipulate the second elongate shaft longitudinally.

5. The robotic system of claim 1, wherein the second medical instrument comprises at least one of a laser tool or a basketing tool.

6. The robotic system of claim 1, wherein a first actuator of the second instrument base controls a longitudinal position of at least a portion of the second elongate shaft.

7. The robotic system of claim 6, wherein a second actuator of the second instrument base controls an activation of a distal portion of the second elongate shaft.

8. The robotic system of claim 1, wherein the second robotic drive input is coupled to a sheath of the second elongate shaft of the second medical instrument.

9. The robotic system of claim 1, wherein the second medical instrument further comprises a third robotic drive input, wherein the third robotic drive input is coupled to an inner portion of the second elongate shaft of the second medical instrument.

10. The robotic system of claim 1, wherein the second elongate shaft forms a service loop.

11. The robotic system of claim 10, wherein the service loop extends at least 45 degrees between the instrument inlet of the first medical instrument and the second instrument base of the second medical instrument.

12. A medical system, comprising:
   an endoscope comprising an endoscope base having an elongate shaft extending from the endoscope base, the endoscope base including a first robotic drive input and a first manual actuator; and a working channel instrument having an instrument shaft configured to extend within the elongate shaft of the endoscope, the working channel instrument including a second robotic drive input and a second manual actuators;

wherein:
the first and second robotic drive inputs are configured to couple to corresponding first and second robotic drive outputs of a robotic end effector;
the first manual actuators is configured to be manually actuated to cause articulation of the elongate shaft of the endoscope when the first robotic drive inputs is decoupled from the first robotic drive output of the robotic end effector; and
the second manual actuator is configured to be manually actuated to cause movement of one or more components of the working channel instrument when the second robotic drive input is decoupled from the second robotic drive output.

13. The medical system of claim 12, wherein the working channel instrument comprises an instrument base including a coupling element configured to allow removable coupling of the instrument base to the endoscope base.

14. The medical system of claim 12, wherein:
the endoscope further comprises a first rotating element that is configured to articulate a distal end of the elongate shaft of the endoscope in a first dimension; and
the first manual actuator is configured to cause manual rotation of the first rotating element.

15. The medical system of claim 12, wherein the working channel instrument further comprises an instrument base coupled to the instrument shaft, the instrument shaft extending from a proximal portion of the instrument base.

16. A medical system comprising:
an endoscope comprising an endoscope base having an elongate shaft extending from the endoscope base, the endoscope base including a first robotic drive input and a first manual actuator; and
a working channel instrument having an instrument base and an instrument shaft configured to extend within the elongate shaft of the endoscope, the instrument base including a second robotic drive input and a second manual actuator;

wherein:
the first and second robotic drive inputs are configured to couple to corresponding first and second robotic drive outputs of a robotic end effector,
the first and second manual actuators are configured to be manually actuated when the first and second robotic drive inputs are decoupled from the first and second robotic drive outputs, respectively; and
the working channel instrument comprises a coupling element configured to couple the instrument shaft to the second robotic drive input, wherein the second robotic drive input of the working channel instrument is operatively coupled to the instrument shaft of the working channel instrument at a point distal to a proximal portion of the instrument base.

17. The medical system of claim 16, wherein the working channel instrument further comprises a linear actuator to associated with the coupling element, the linear actuator configured to move the instrument shaft of the working channel instrument longitudinally.

18. The medical system of claim 12, wherein the working channel instrument comprises at least one of a laser tool or a basketing tool.

19. The medical system of claim 12, wherein the second robotic drive input controls a longitudinal position of at least a portion of the instrument shaft.

20. The medical system of claim 12, wherein the second manual actuator controls articulation of a distal portion of the instrument shaft.

21. The medical system of claim 12, wherein the second robotic drive input is coupled to a sheath of the instrument shaft.

22. The medical system of claim 12, wherein the instrument shaft forms a service loop between an inlet of the endoscope base and an instrument base of the working channel instrument.

23. The medical system of claim 12, wherein the working channel instrument comprises a coupling element configured to couple the instrument shaft to the second robotic drive input.

24. The medical system of claim 23, wherein the working channel instrument further comprises a linear actuator associated with the coupling element, the linear actuator being configured to move the instrument shaft of the working channel instrument longitudinally.

25. The medical system of claim 12, wherein the second robotic drive input of the working channel instrument is operatively coupled to the instrument shaft at a point distal to a proximal portion of a base of the working channel instrument.

26. The medical system of claim 25, wherein the second robotic drive input is operatively coupled to the instrument shaft at a point distal to a proximal portion of the instrument base.

27. The medical system of claim 12, wherein the second manual actuator is a linear actuator.

28. The medical system of claim 12, wherein the second manual actuator is associated with a base of the working channel instrument.

29. The medical system of claim 28, further comprising a third manual actuator associated with the base of the working channel instrument and configured to be manually actuated to cause movement of a component of the working channel instrument, the third manual actuator being independently movable relative to the second manual actuator.

* * * * *